(12) United States Patent
Conte et al.

(10) Patent No.: US 7,572,801 B2
(45) Date of Patent: Aug. 11, 2009

(54) PYRIDOPYRIMIDINONE DERIVATIVES WHICH ARE HM74A AGONISTS

(75) Inventors: Aurelia Conte, Basel (CH); Henrietta Dehmlow, Grenzach-Wyhlen (DE); Uwe Grether, Efringen-Kirchen (DE); Nicole A. Kratochwil, Sool (CH); Holger Kuehne, Grenzach-Wyhlen (DE); Robert Narquizian, St. Louis (FR); Constantinos Panousis, Bottmingen (CH); Jens-Uwe Peters, Grenzach-Wyhlen (DE); Fabienne Ricklin, Hombourg (FR); Stephan Roever, Inzlingen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/801,863

(22) Filed: May 11, 2007

(65) Prior Publication Data
US 2007/0275987 A1    Nov. 29, 2007

(51) Int. Cl.
A61K 31/519    (2006.01)
C07D 471/04    (2006.01)
A61P 9/10      (2006.01)
A61P 3/00      (2006.01)
A61P 3/10      (2006.01)

(52) U.S. Cl. .............. 514/264.1; 514/264.11; 544/279; 546/316

(58) Field of Classification Search .......... 514/264.1, 514/264.11; 544/279
See application file for complete search history.

(56) References Cited

U.S. PATENT DOCUMENTS 3,950,160 A    4/1976    Abu El-Haj et al.

FOREIGN PATENT DOCUMENTS

WO    WO 03/063874 A1    8/2003
WO    WO 2005105760    *    4/2005
WO    WO 2005/077950 A2    8/2005

OTHER PUBLICATIONS

Jin et al. Arterioscler. Thromb. Vasc. Biol., 17, pp. 2020-2028 (1997).
Carlson et al., J. Intern. Med., 226, pp. 271-276 (1989).
Grundy et al., Arch. Intern. Med., 162, pp. 1568-1576 (2002).
Wise et al., J. Biol. Chem., 278 (11), pp. 9869-9874 (2003).
Soga et al., Biochem. Biophys. Res. Commun., 303, pp. 364-369 (2003).
Tunaru et al., Nature Medicine, 9, pp. 352-355 (2003).
Abarca et al., Tetrahedron, 45, pp. 7041-7048 (1989).
Sanmartin et al., Bioorg. Med. Chem., 13, pp. 2031-2044 (2005).
Taylor et al., J. Org. Chem., 19(10), pp. 1633-1640 (1954).
Robins et al., J. Am. Chem. Soc., 80, pp. 3449-3457 (1958).

* cited by examiner

*Primary Examiner*—Mark L Berch
*Assistant Examiner*—Cecilia M Jaisle
(74) *Attorney, Agent, or Firm*—George W. Johnston; Dennis P. Tramaloni; Brian C. Remy

(57) ABSTRACT

The invention is concerned with novel pyridopyrimidinone derivatives of formula (I):

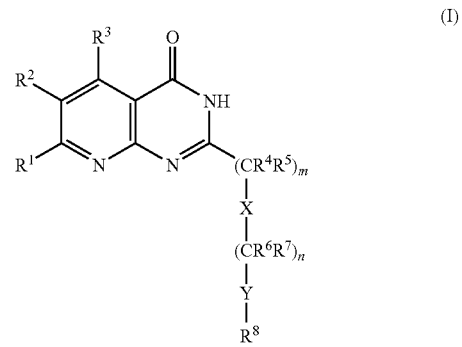

wherein $R^1$ to $R^8$, X, Y, m and n are as defined in the description and in the claims. The compounds of the present invention are HM74A agonists with improved properties compared to niacin and can be used for the treatment and/or prevention of diseases such as dyslipidemia, atherosclerosis, diabetes, metabolic syndrome, and other related diseases associated with HM74A.

39 Claims, No Drawings

PYRIDOPYRIMIDINONE DERIVATIVES WHICH ARE HM74A AGONISTS

PRIORITY TO RELATED APPLICATION(S)

This application claims the benefit of European Patent Application No. 06114438.2, filed May 23, 2006, which is hereby incorporated by reference in its entirety.

BACKGROUND OF THE INVENTION

Coronary heart disease (CHD) remains the leading cause of death in Western countries. In the United States 13.2 million or 4.85% of the population is affected, with 1.2 million new or recurrent attacks and around 500 thousand deaths per year (American Heart Association, Statistics for 2001). The disease is influenced by several well-established risk factors, such as age, sex, blood lipids, blood pressure, smoking, diabetes, and body mass index (BMI) as an indicator of overweight and obesity. The National Cholesterol Education Program (NCEP) Adult Treatment Panel III defines elevated plasma levels of low density lipoprotein (LDL) cholesterol (LDL-C$\geq$160 mg/dL), and low levels of high density lipoprotein (HDL) cholesterol (HDL-C$\leq$40 mg/dL) as independent risk factors for CHD. Many prospective epidemiological studies have indicated that a decreased HDL-C level is a significant independent risk factor for heart disease, while increased HDL-C levels$\geq$60 mg/dL ($\geq$1.55 mmol) have a protective role against CHD. Nicotinic acid (Niacin), a vitamin of the B complex, is used for almost 40 years as a lipid-lowering drug with a favorable profile for all lipoprotein classes. Numerous clinical studies have shown the beneficial effects of niacin, demonstrating a reduction of coronary artery disease and overall mortality. Niacin is the most potent agent currently available to raise HDL. It has been proposed that niacin's main mode of action is through inhibition of lipolysis in the adipose tissue having as a result the reduction of free fatty acids (FFA) in plasma and liver and consequently the decreased production of very low density lipoproteins (VLDL), accounting for the reduction of total cholesterol (TC), triglycerides (TGs), and LDL-C. Due to the decreased TG rich lipoproteins levels, less modification of HDL particles occurs upon the action of cholesteryl ester transfer protein (CETP), resulting in a decreased catabolism of HDL. A direct inhibition of lipoprotein AI-HDL (LPAI-HDL) particle uptake by the liver has been also proposed, accounting for the overall HDL raising properties of niacin (Jin et al. Arterioscler. Thromb. Vasc. Biol. 1997, 17, 2020-2028).

Niacin also has anti-diabetic, anti-thrombotic and anti-inflammatory properties that contribute to the overall cardioprotective effects. Through a variety of mechanisms niacin reduces thrombosis, such as the reduction of lipoprotein (a) (Lp(a)) which is a potent inhibitor of fibrinolytic activity, and it is the only currently approved drug that effectively reduces the serum levels of Lp(a) (Carlson et al. J. Intern. Med. 1989, 226, 271-6). Inflammation is a critical component of atherosclerosis, leading to recruitment of macrophages which both promote plaque development and decrease plaque stability thus increasing cardiovascular risk. Niacin has been suggested to have anti-inflammatory properties, such as the reduction of C-reactive protein (CRP) levels (Grundy et al. Arch. Intern. Med. 2002, 162, 1568-76). Several prospective studies have established a strong and direct correlation between cardiovascular risk and CRP levels, a measure of vascular inflammation. Extensive use of niacin has been hampered due to side effects, mainly intense cutaneous flushing.

HM74A/HM74, a G-protein coupled receptor (GPCR), was identified as a receptor for niacin and proposed as the mediator of the niacin effects (Wise et al. J. Biol. Chem. 2003, 278 (11) 9869-9874 and Soga et al Biochem Biophys Res Commun 2003 303 (1) 364-369). In support, deletion of the PUMA-G (HM74A orthologue) in mice abrogated the niacin effects on reduction of plasma free fatty acids and triglycerides (Tunaru et al. Nature Medicine 2003, (3) 352-255).

The novel compounds of the present invention exceed the compounds known in the art, inasmuch as they bind to and activate HM74A. The compounds of the present invention are selective for HM74A by which is meant that they show greater affinity for HM74A than for HM74. The compounds of the present invention are expected to have an enhanced therapeutic potential and exhibit reduced side effects compared to nicotinic acid. The compounds of the present invention can be used as pharmaceutical compositions for the treatment and/or prevention of diseases which are modulated by HM74A agonists. Examples of such diseases are increased lipid and cholesterol levels, particularly dyslipidemia, low HDL-cholesterol, atherosclerotic diseases, hypertriglyceridemia, thrombosis, angina pectoris, peripheral vascular disease, stroke, diabetes, particularly non-insulin dependent diabetes mellitus, metabolic syndrome, Alzheimer's disease, Parkinson's disease, schizophrenia, sepsis, inflammatory diseases (such as e.g. asthma, arthritis, colitis, pancreatitis, cholestasis/fibrosis of the liver, and diseases that have an inflammatory component such as e.g. Alzheimer's disease or impaired/improvable cognitive function).

SUMMARY OF THE INVENTION

The present invention relates to the compounds of the formula (I) including all pharmaceutically acceptable salts and esters thereof wherein formula I is:

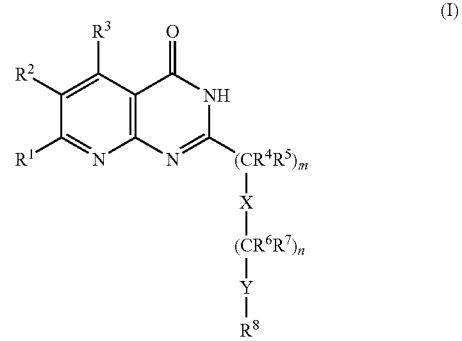

wherein $R^1$ to $R^8$, X, Y, m and n are as defined in the detailed description and in the claims. The compounds of the present invention are HM74A agonists with improved properties compared to niacin and can be used for the treatment and/or prevention of diseases such as dyslipidemia, atherosclerosis, diabetes, and other related diseases associated with the HM74A receptor. In addition, the invention is concerned with a process for the manufacture of the above compounds, pharmaceutical compositions which contain such compounds as well as the use of said compounds.

DETAILED DESCRIPTION OF THE INVENTION

Unless otherwise indicated, the following definitions are set forth to illustrate and define the meaning and scope of the various terms used to describe the invention herein.

In this specification the term "lower" is used to mean a group having one to seven carbon atoms. In preferred embodiments such "lower" groups will have one to four carbon atoms.

The term "halogen" refers to fluorine, chlorine, bromine or iodine. In preferred embodiments, the halogen will be either fluorine, chlorine or bromine.

The term "alkyl", alone or in combination with other groups, refers to a branched or straight-chain monovalent saturated aliphatic hydrocarbon radical of one to twenty carbon atoms. In certain preferred embodiments, the alkyl is one to sixteen carbon atoms, and more preferably one to ten carbon atoms. In more preferred embodiments, the alkyl is a lower-alkyl as described below.

The term "lower-alkyl," alone or in combination with other groups, refers to a branched or straight-chain monovalent alkyl radical of one to seven carbon atoms. In preferred embodiments, the lower alkyl has one to four carbon atoms. This term is further exemplified by such radicals as methyl, ethyl, n-propyl, isopropyl, n-butyl, s-butyl, t-butyl and the like.

The term "fluoro-lower-alkyl" refers to lower-alkyl groups which are mono- or multiply substituted with fluorine. Examples of fluoro-lower-alkyl groups are e.g. $CFH_2$, $CF_2H$, $CF_3$, $CF_3CH_2$, $CF_3(CH_2)_2$, $(CF_3)_2CH$ and $CF_2H—CF_2$.

The term "alkenyl", alone or in combination with other groups, stands for a straight-chain or branched hydrocarbon residue comprising an olefinic bond and up to 20 carbon atoms. In preferred embodiments, the alkenyl has up to 16 carbon atoms. The term "lower-alkenyl" refers to a straight-chain or branched hydrocarbon residue comprising an olefinic bond and up to 7 carbon atoms. In preferred embodiments, the lower-alkenyl has up to 4 carbon atoms, such as e.g. 2-propenyl.

The term "alkinyl", alone or in combination with other groups, stands for a straight-chain or branched hydrocarbon residue comprising a triple bond and up to 20 carbon atoms. In preferred embodiments, the alkinyl has up to 16 carbon atoms. The term "lower-alkinyl" refers to a straight-chain or branched hydrocarbon residue comprising a triple bond and up to 7 carbon atoms. In preferred embodiments, the lower-alkinyl has up to 4 carbon atoms, such as e.g. 2-propinyl.

The term "amino," alone or in combination, signifies a primary, secondary or tertiary amino group bonded via the nitrogen atom. A secondary amino group carries an alkyl or cycloalkyl substituent and the tertiary amino group carries two similar or different alkyl or cycloalkyl substituents (which can optionally form a ring with the nitrogen atom to which they are attached). Examples of amino groups are —$NH_2$, methylamino, ethylamino, dimethylamino, diethylamino, methyl-ethylamino, pyrrolidin-1-yl or piperidino etc. In certain preferred embodiments the amino is a primary amino, dimethylamino or diethylamino and, more preferably, a dimethylamino.

The term "cycloalkyl" refers to a monovalent carbocyclic radical of 3 to 10 carbon atoms. In preferred embodiments, the cydoalkyl has 3 to 7 carbon atoms, and more preferably 3 to 6 carbon atoms, such as cyclopropyl, cyclobutyl, cyclopentyl, or cyclohexyl.

The term "fluoro-cycloalkyl" refers to a cydoalkyl group as defined above, which is mono- or multiply substituted with fluorine (preferably with 1 to 4 fluorine atoms). Examples of fluoro-cycloalkyl are 2-fluorocyclopropyl, 2,2-difluorocydopropyl, 2,2,3,3-tetrafluorocyclopropyl, 3-fluorocyclobutyl, 3,3-difluorocyclobutyl, and 3,3-difluorocyclopentyl.

The term "alkoxy" refers to the group R'—O—, wherein R' is an alkyl. The term "lower-alkoxy" refers to the group R'—O—, wherein R' is a lower-alkyl.

The term "fluoro-lower-alkoxy" refers to the group R"—O—, wherein R" is fluoro-lower-alkyl. Examples of fluoro-lower-alkoxy groups are $CFH_2$—O, $CF_2H$—O, $CF_3$—O, $CF_3CH_2$—O, $CF_3(CH_2)_2$—O, $(CF_3)_2CH$—O, and $CF_2H$—$CF_2$—O.

The term "aryl", alone or in combination, relates to the phenyl or naphthyl group which can optionally be substituted by 1 to 5 (preferably 1 to 3) substituents independently selected from the group consisting of halogen, lower-alkyl, hydroxy-lower-alkyl, lower-alkoxy, fluoro-lower-alkoxy, carboxy, carboxy-lower-alkyl, lower-alkoxy-carbonyl, lower-alkoxy-carbonyl-lower-alkyl, $H_2NC(O)$, (H,lower-alkyl)NC(O), (lower-alkyl)$_2$NC(O), $H_2NC(O)$-lower-alkyl, (H,lower-alkyl)NC(O)-lower-alkyl, (lower-alkyl)$_2$NC(O)-lower-alkyl, fluoro-lower-alkyl, $H_2N$-lower-alkyl, (H,lower-alkyl)N-lower-alkyl, (lower-alkyl)$_2$N-lower-alkyl, lower-alkyl-$SO_2$, lower-alkyl-$SO_2O$, lower-alkyl-$SO_2$—NH, lower-alkyl-$SO_2$—N(lower-alkyl), $H_2NSO_2$, (H,lower-alkyl)$NSO_2$, (lower-alkyl)$_2NSO_2$, cyano, cycloalkyl, lower-alkoxy-lower-alkyl, lower-alkenyl, lower-alkinyl, fluoro-lower-alkoxy-lower-alkyl, cyano-lower-alkyl, optionally substituted phenyl and optionally substituted heteroaryl. Other possible substituents for the aryl are selected from the group consisting of hydroxy, amino, $NO_2$, dioxo-lower-alkylene (forming for example a benzodioxyl group), lower-alkylcarbonyl, lower-alkylcarbonyloxy, lower-alkylcarbonyl-NH, cydoalkyl, phenyl and phenyloxy. Preferred substituents for the aryl are selected from the group consisting of halogen, lower-alkyl, cycloalkyl and optionally substituted phenyl. Furthermore, aryl groups can be substituted as described in the description and claims below.

The term "heteroaryl" refers to an aromatic 5 to 6 membered monocyclic ring or a 9 to 10 membered bicyclic ring which can comprise 1, 2 or 3 hetero-atoms selected from nitrogen, oxygen and/or sulphur. Examples of heteroaryl include furyl, pyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzoimidazolyl, indolyl, indazolyl, benzoisothiazolyl, benzoxazolyl, benzoisoxazolyl and quinolinyl. Preferred heteroaryl groups are pyridinyl, oxazolyl and triazolyl, particularly pyridinyl. A heteroaryl group may optionally have a substitution pattern as described earlier in connection with the term "aryl". Furthermore, heteroaryl groups can be substituted as described in the description and claims below.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 1 mg to about 5,000 mg, preferably from about 1 mg to about 1,000 mg, and more preferably from about 1 to 300 mg, should be appropriate, although the upper limit may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The methyl and ethyl esters are especially preferred. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

The compounds of formula (I) can form pharmaceutically acceptable acid addition salts. Examples of such pharmaceutically acceptable salts are salts of the compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) can further form salts with bases. Examples of such salts are alkaline, earth-alkaline and ammonium salts such as e.g. Na—, K—, Ca— and trimethylammoniumsalt. The term "pharmaceutically acceptable salts" also refers to such salts. Salts obtained by the addition of an acid are preferred.

In detail, the present invention relates to the compounds of formula (I) including all pharmaceutically acceptable salts or esters thereof wherein formula I is:

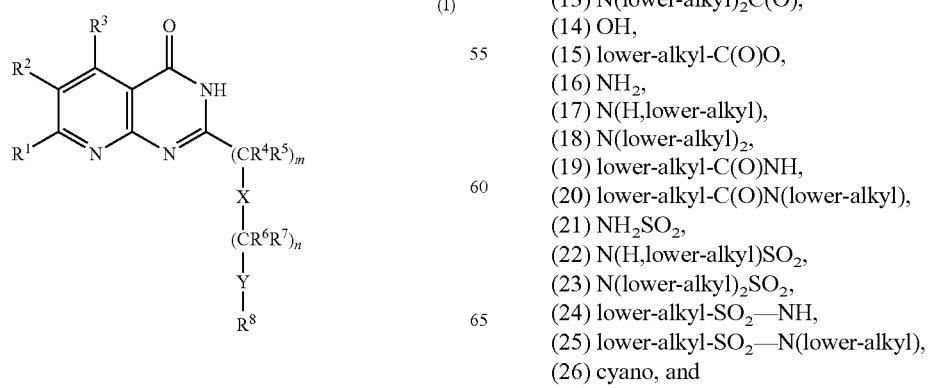

(I)

wherein:
(a) X is selected from the group consisting of:
(1) a single bond,
(2) O,
(3) $N(R^9)C(O)$,
(4) $N(R^9)C(O)O$,
(5) $OC(O)NR^9$,
(6) $N(R^9)C(O)NR^{10}$,
(7) $N(R^9)SO_2$, and
(8) $C(O)NR^9$ if m is 1, 2 or 3;
(b) Y is selected from the group consisting of:
(1) a single bond, and
(2) O if n is 1, 2, 3, 4, 5 or 6;
(c) $R^1$, $R^2$ and $R^3$ are independently from each other selected from the group consisting of:
(1) hydrogen,
(2) halogen,
(3) lower-alkyl,
(4) fluoro-lower-alkyl,
(5) lower-alkoxy,
(6) fluoro-lower-alkoxy, and
(7) cycloalkyl;
(d) $R^4$, $R^5$, $R^6$ and $R^7$ are independently from each other selected from the group consisting of:
(1) hydrogen,
(2) fluoro,
(3) lower-alkyl, and
(4) fluoro-lower-alkyl; or alternatively,
$R^4$ and $R^5$ are bound together to form a ring together with the carbon atom to which they are attached wherein —$R^4$—$R^5$— is —$(CH_2)_{2-6}$—, or $R^6$ and $R^7$ are bound together to form a ring together with the carbon atom to which they are attached wherein —$R^6$—$R^7$— is —$(CH_2)_{2-6}$—;
(e) $R^8$ is aryl or heteroaryl, wherein said aryl or heteroaryl is optionally substituted with 1 to 3 substituents independently from each other selected from the group consisting of:
(1) halogen,
(2) lower-alkyl,
(3) lower-alkoxy,
(4) fluoro-lower-alkyl,
(5) fluoro-lower-alkoxy,
(6) cycloalkyl,
(7) fluoro-cycloalkyl,
(8) cycloalkyl-oxy,
(9) C(O)OH,
(10) lower-alkoxy-C(O),
(11) $NH_2C(O)$,
(12) N(H,lower-alkyl)C(O),
(13) N(lower-alkyl)$_2$C(O),
(14) OH,
(15) lower-alkyl-C(O)O,
(16) $NH_2$,
(17) N(H,lower-alkyl),
(18) N(lower-alkyl)$_2$,
(19) lower-alkyl-C(O)NH,
(20) lower-alkyl-C(O)N(lower-alkyl),
(21) $NH_2SO_2$,
(22) N(H,lower-alkyl)$SO_2$,
(23) N(lower-alkyl)$_2SO_2$,
(24) lower-alkyl-$SO_2$—NH,
(25) lower-alkyl-$SO_2$—N(lower-alkyl),
(26) cyano, and

(27) phenyl which is optionally substituted with 1 to 3 substituents independently selected from the group consisting of halogen, lower-alkyl, lower-alkoxy and fluoro-lower-alkyl;

(f) $R^9$ and $R^{10}$ independently from each other are selected from the group consisting of:
(1) hydrogen,
(2) lower-alkyl, and
(3) fluoro-lower-alkyl; and (g) m is 0, 1, 2 or 3; and n is 0, 1, 2, 3, 4, 5 or 6; wherein m+n is $\geq 1$.

Preferred are compounds of formula (I) above wherein:
(a) X is selected from the group consisting of:
(1) a single bond,
(2) O,
(3) $N(R^9)C(O)$,
(4) $N(R^9)C(O)O$,
(5) $OC(O)NR^9$,
(6) $N(R^9)C(O)NR^{10}$, and
(7) $C(O)NR^9$ if m is 1, 2 or 3;
(b) Y is selected from the group consisting of:
(1) a single bond, and
(2) O if n is 1, 3, 4, 5 or 6;

Compounds of formula (I) are individually preferred and physiologically acceptable salts thereof are individually preferred and pharmaceutically acceptable esters thereof are individually preferred, with the compounds of formula (I) being particularly preferred.

The compounds of formula (I) can have one or more asymmetric C atoms and can therefore exist as an enantiomeric mixture, diastereomeric mixture or as optically pure compounds.

Preferably, X is selected from the group consisting of:
(1) a single bond,
(2) O,
(3) $N(R^9)C(O)$,
(4) $N(R^9)C(O)O$,
(5) $OC(O)NR^9$,
(6) $N(R^9)C(O)NR^{10}$, and
(7) $C(O)NR^9$ if m is 1, 2 or 3;

Preferably, Y is a single bond, or, if n is 1, 3, 4, 5 or 6, Y can also be O.

Preferred compounds of formula (I) as described above are those, wherein X is selected from the group consisting of:
(1) a single bond,
(2) O,
(3) $N(R^9)C(O)$,
(4) $N(R^9)C(O)O$, and
(5) $N(R^9)C(O)NR^{10}$.

Preferably, X is is selected from the group consisting of:
(1) a single bond,
(2) O,
(3) $N(R^9)C(O)$, and
(4) $N(R^9)C(O)O$.

Furthermore, it is preferred that X is $N(R^9)SO_2$. In certain preferred embodiments, Y is a single bond. In other particular preferred embodiments, Y is O. Each of the groups given above for X and Y respectively individually constitutes a particular preferred embodiment.

The X-groups as mentioned above are bound to the $(CR^4R^5)_m$ group on their left side and to the $(CR^6R^7)_n$ group on their right side.

Another preferred embodiment of the present invention is concerned with compounds of formula (I), wherein $R^1$, $R^2$ and $R^3$ independently from each other are selected from the group consisting of hydrogen, halogen, lower-alkyl and cycloalkyl; preferably hydrogen, halogen and lower-alkyl.

Preferably, $R^1$ is hydrogen, methyl or fluoro, more preferably hydrogen or methyl. Preferably, $R^2$ is hydrogen, methyl, ethyl, butyl, fluoro, chloro or bromo, more preferably hydrogen, methyl or bromo. Preferably, $R^3$ is hydrogen.

Other preferred compounds of the present invention are those, wherein $R^4$, $R^5$, $R^6$ and $R^7$ independently from each other are hydrogen or lower-alkyl. Preferably, $R^4$, $R^5$, $R^6$ and $R^7$ are hydrogen. In cases, wherein m or n are larger than 1, more than one of $R^4$, $R^5$, $R^6$ or $R^7$ occur. In such cases, the individual $R^4$, $R^5$, $R^6$ or $R^7$ can be equal or different. For example, if m is 3 and $R^4$ and $R^5$ are hydrogen or lower-alkyl, the group $-(CR^4R^5)_3-$ can, for example, be $-CH(CH_3)-CH_2-CH_2-$. Furthermore, in cases wherein m or n are larger than 1, it is preferred that only one $R^4$ and $R^5$ or one $R^6$ and $R^7$ are bound together to form a cycloalkyl.

In another preferred embodiment of the present invention, $R^8$ is aryl or heteroaryl, which aryl or heteroaryl is optionally substituted with 1 to 3 substituents independently selected from the group consisting of:
(1) halogen,
(2) lower-alkyl,
(3) lower-alkoxy,
(4) fluoro-lower-alkyl,
(5) fluoro-lower-alkoxy, and
(6) phenyl which is optionally substituted halogen.

Preferably, $R^8$ is aryl or heteroaryl, which aryl or heteroaryl is optionally substituted with 1 to 3 substituents independently selected from the group consisting of halogen, lower-alkyl, lower-alkoxy or fluoro-lower-alkyl. Preferably, $R^8$ is phenyl or naphthyl, which phenyl is optionally substituted with 1 to 2 substituents independently selected from the group consisting of halogen and lower-alkoxy. More preferably, $R^8$ is phenyl, 4-fluoro-phenyl, 3-chloro-phenyl, 2-methoxy-phenyl, 2-chloro-phenyl, 2-fluoro-phenyl, 3,4-dichlorophenyl, naphthalen-1-yl, or naphthalen-2-yl. Other preferred compounds are those, wherein $R^8$ is 3-chloro-4-fluoro-phenyl, 2,5-difluoro-phenyl or 5-methyl-2-phenyl-oxazol-4-yl.

It is preferred that m is 0 or 1. Furthermore, it is preferred that n is 0, 1, 2, 3 or 4. Each of the individual values given above for m and n respectively, individually constitutes a preferred embodiment of the present invention, also in combination with any of the other preferred embodiments. Compounds in which $R^9$ and $R^{10}$ are hydrogen are also preferred In particular, preferred compounds are the compounds of formula (I) described in the examples as individual compounds as well as pharmaceutically acceptable salts as well as pharmaceutically acceptable esters thereof. Preferred substituents are those of the specific examples given below.

Preferred compounds of formula (I) are those selected from the group consisting of:
2-Benzyloxymethyl-3H-pyrido[2,3-d]pyrimidin-4-one,
2-Phenoxymethyl-3H-pyrido[2,3-d]pyrimidin-4-one,
2-(4-Chloro-phenoxymethyl)-3H-pyrido[2,3-d]pyrimidin-4-one,
2-(5-Phenyl-pentyl)-3H-pyrido[2,3-d]pyrimidin-4-one,
2-(4-Methoxy-phenoxymethyl)-3H-pyrido[2,3-d]pyrimidin-4-one,
2-(4-Ethyl-phenoxymethyl)-3H-pyrido[2,3-d]pyrimidin-4-one,
2-(4-Phenyl-butyl)-3H-pyrido[2,3-d]pyrimidin-4-one,
2-(4-Fluoro-phenoxymethyl)-3H-pyrido[2,3-d]pyrimidin-4-one,
2-(3-Chloro-phenoxymethyl)-3H-pyrido[2,3-d]pyrimidin-4-one,
2-Phenethyl-3H-pyrido[2,3-d]pyrimidin-4-one,
2-[2-(3-Chloro-phenyl)-ethyl]-3H-pyrido[2,3-d]pyrimidin-4-one, 2-[2-(3-Methoxy-phenyl)-ethyl]-3H-pyrido[2,3-d]pyrimidin-4-one,
2-[4-(4-Chloro-phenyl)-butyl]-3H-pyrido[2,3-d]pyrimidin-4-one,
2-(6-Phenyl-hexyl)-3H-pyrido[2,3-d]pyrimidin-4-one,
2-[4-(4-Fluoro-phenyl)-butyl]-3H-pyrido[2,3-d]pyrimidin-4-one,
2-(2-Methoxy-phenoxymethyl)-3H-pyrido[2,3-d]pyrimidin-4-one,
2-p-Tolyloxymethyl-3H-pyrido[2,3-d]pyrimidin-4-one,
2-(2-Chloro-phenoxymethyl)-3H-pyrido[2,3-d]pyrimidin-4-one,
2-(2,3-Dimethyl-phenoxymethyl)-3H-pyrido[2,3-d]pyrimidin-4-one,
2-(Naphthalen-1-yloxymethyl)-3H-pyrido[2,3-d]pyrimidin-4-one,
2-(4-Chloro-2-methyl-phenoxymethyl)-3H-pyrido[2,3-d]pyrimidin-4-one,
6-Methyl-2-(4-phenyl-butyl)-3H-pyrido[2,3-d]pyrimidin-4-one,
(4-Oxo-3,4-dihydro-pyrido[2,3-d]pyrimidin-2-ylmethyl)-carbamic acid benzyl ester,
N-(4-Oxo-3,4-dihydro-pyrido[2,3-d]pyrimidin-2-ylmethyl)-3-phenyl-propionamide,
N-(4-Oxo-3,4-dihydro-pyrido[2,3-d]pyrimidin-2-ylmethyl)-4-phenyl-butyramide,
6-Bromo-2-(4-phenyl-butyl)-3H-pyrido[2,3-d]pyrimidin-4-one,
6-Bromo-2-[4-(4-fluoro-phenyl)-butyl]-3H-pyrido[2,3-d]pyrimidin-4-one,
2-[3-(4-Methoxy-phenyl)-propoxy]-3H-pyrido[2,3-d]pyrimidin-4-one,
2-(3-Phenyl-propoxy)-3H-pyrido[2,3-d]pyrimidin-4-one,
2-(4-Phenyl-butoxy)-3H-pyrido[2,3-d]pyrimidin-4-one,
2-[4-(4-Methoxy-phenyl)-butoxy]-3H-pyrido[2,3-d]pyrimidin-4-one,
2-(3-Pyridin-3-yl-propoxy)-3H-pyrido[2,3-d]pyrimidin-4-one,
2-(2-Phenoxy-ethoxy)-3H-pyrido[2,3-d]pyrimidin-4-one,
2-[2-(Naphthalen-2-yloxy)-ethoxy]-3H-pyrido[2,3-d]pyrimidin-4-one,
2-(3-Phenoxy-propoxy)-3H-pyrido[2,3-d]pyrimidin-4-one,
2-Phenethyloxymethyl-3H-pyrido[2,3-d]pyrimidin-4-one,
2-[2-(2-Fluoro-phenyl)-ethoxymethyl]-3H-pyrido[2,3-d]pyrimidin-4-one,
2-[3-(3,4-Difluoro-phenoxy)-propoxy]-3H-pyrido[2,3-d]pyrimidin-4-one,
2-[3-(4-Methoxy-phenoxy)-propoxy]-3H-pyrido[2,3-d]pyrimidin-4-one,
2-[2-(4-Fluoro-phenyl)-ethoxymethyl]-3H-pyrido[2,3-d]pyrimidin-4-one,
2-[4-(4-Fluoro-phenyl)-3-methyl-butyl]-3H-pyrido[2,3-d]pyrimidin-4-one,
2-[5-(4-Chloro-phenyl)-pentyl]-3H-pyrido[2,3-d]pyrimidin-4-one,
2-[3-(4-Fluoro-phenoxy)-propyl]-3H-pyrido[2,3-d]pyrimidin-4-one,
2-[2-(4-Chloro-phenyl)-ethoxymethyl]-3H-pyrido[2,3-d]pyrimidin-4-one,
2-(2-p-Tolyl-ethoxymethyl)-3H-pyrido[2,3-d]pyrimidin-4-one,
2-[2-(4-Methoxy-phenyl)-ethoxymethyl]-3H-pyrido[2,3-d]pyrimidin-4-one,
2-(2-Benzyloxy-ethyl)-3H-pyrido[2,3-d]pyrimidin-4-one,
2-(4'-Fluoro-biphenyl-4-yloxymethyl)-3H-pyrido[2,3-d]pyrimidin-4-one,
2-(4-m-Tolyl-butyl)-3H-pyrido[2,3-d]pyrimidin-4-one,
2-(1-Methyl-4-phenyl-butyl)-3H-pyrido[2,3-d]pyrimidin-4-one,
2-(Naphthalen-2-yloxymethyl)-3H-pyrido[2,3-d]pyrimidin-4-one,
1-Benzyl-3-(4-oxo-3,4-dihydro-pyrido[2,3-d]pyrimidin-2-ylmethyl)-urea,
2-[2-(4-Fluoro-phenyl)-ethoxymethyl]-6-methyl-3H-pyrido[2,3-d]pyrimidin-4-one,
2-(4-Iodo-phenoxymethyl)-3H-pyrido[2,3-d]pyrimidin-4-one,
2-[3-(4-Fluoro-phenoxy)-propoxy]-3H-pyrido[2,3-d]pyrimidin-4-one,
2-(3-p-Tolyloxy-propoxy)-3H-pyrido[2,3-d]pyrimidin-4-one,
2-[3-(2-Fluoro-phenoxy)-propoxy]-3H-pyrido[2,3-d]pyrimidin-4-one,
2-(3-o-Tolyloxy-propoxy)-3H-pyrido[2,3-d]pyrimidin-4-one,
2-[2-(2-Fluoro-phenyl)-ethoxymethyl]-7-methyl-3H-pyrido[2,3-d]pyrimidin-4-one,
(4-Oxo-3,4-dihydro-pyrido[2,3-d]pyrimidin-2-ylmethyl)-carbamic acid 2-chloro-benzyl ester,
2-[3-(3-Fluoro-phenoxy)-propoxy]-3H-pyrido[2,3-d]pyrimidin-4-one,
2-(3-m-Tolyloxy-propoxy)-3H-pyrido[2,3-d]pyrimidin-4-one,
2-[2-(2-Trifluoromethyl-phenyl)-ethoxymethyl]-3H-pyrido[2,3-d]pyrimidin-4-one,
2-[2-(2-Methoxy-phenyl)-ethoxymethyl]-3H-pyrido[2,3-d]pyrimidin-4-one,
2-(2-o-Tolyl-ethoxymethyl)-3H-pyrido[2,3-d]pyrimidin-4-one,
2-[2-(2-Chloro-phenyl)-ethoxymethyl]-3H-pyrido[2,3-d]pyrimidin-4-one,
2-Phenethyloxy-3H-pyrido[2,3-d]pyrimidin-4-one,
2-(3,4-Dichloro-benzyloxy)-3H-pyrido[2,3-d]pyrimidin-4-one,
2-[2-(4-Fluoro-phenyl)-ethoxy]-3H-pyrido[2,3-d]pyrimidin-4-one,
2-(2,4-Difluoro-benzyloxy)-3H-pyrido[2,3-d]pyrimidin-4-one,
2-[2-(4-Chloro-phenyl)-ethoxy]-3H-pyrido[2,3-d]pyrimidin-4-one,
2-(5-Phenyl-pentyloxy)-3H-pyrido[2,3-d]pyrimidin-4-one,
2-(6-Phenyl-hexyloxy)-3H-pyrido[2,3-d]pyrimidin-4-one,
2-[3-(4-Chloro-phenoxy)-propoxy]-3H-pyrido[2,3-d]pyrimidin-4-one,
2-[3-(2-Chloro-phenoxy)-propoxy]-3H-pyrido[2,3-d]pyrimidin-4-one,
2-[2-(3-Chloro-phenyl)-ethoxymethyl]-3H-pyrido[2,3-d]pyrimidin-4-one,
(6-Methyl-4-oxo-3,4-dihydro-pyrido[2,3-d]pyrimidin-2-ylmethyl)-carbamic acid benzyl ester,
and all pharmaceutically acceptable salts and esters thereof.

Particularly preferred compounds of formula (I) are those selected from the group consisting of:
2-[4-(4-Fluoro-phenyl)-butyl]-3H-pyrido[2,3-d]pyrimidin-4-one,
2-(2-Methoxy-phenoxymethyl)-3H-pyrido[2,3-d]pyrimidin-4-one,
2-(Naphthalen-1-yloxymethyl)-3H-pyrido[2,3-d]pyrimidin-4-one,
6-Methyl-2-(4-phenyl-butyl)-3H-pyrido[2,3-d]pyrimidin-4-one,
(4-Oxo-3,4-dihydro-pyrido[2,3-d]pyrimidin-2-ylmethyl)-carbamic acid benzyl ester,
N-(4-Oxo-3,4-dihydro-pyrido[2,3-d]pyrimidin-2-ylmethyl)-3-phenyl-propionamide, 2-[2-(Naphthalen-2-yloxy)-ethoxy]-3H-pyrido[2,3-d]pyrimidin-4-one,
2-(3-Phenoxy-propoxy)-3H-pyrido[2,3-d]pyrimidin-4-one,
2-[2-(2-Fluoro-phenyl)-ethoxymethyl]-3H-pyrido[2,3-d]pyrimidin-4-one,
2-(Naphthalen-2-yloxymethyl)-3H-pyrido[2,3-d]pyrimidin-4-one,
2-[2-(2-Fluoro-phenyl)-ethoxymethyl]-7-methyl-3H-pyrido[2,3-d]pyrimidin-4-one,
2-(3,4-Dichloro-benzyloxy)-3H-pyrido[2,3-d]pyrimidin-4-one,
2-[3-(2-Chloro-phenoxy)-propoxy]-3H-pyrido[2,3-d]pyrimidin-4-one,
2-[2-(3-Chloro-phenyl)-ethoxymethyl]-3H-pyrido[2,3-d]pyrimidin-4-one,
and all pharmaceutically acceptable salts and esters thereof.
Other preferred compounds as defined above are those selected from the group consisting of:
6-Chloro-2-[2-(2,5-difluoro-phenyl)-ethoxymethyl]-3H-pyrido[2,3-d]pyrimidin-4-one,
6-Chloro-2-[2-(3-chloro-phenyl)-ethoxymethyl]-3H-pyrido[2,3-d]pyrimidin-4-one,
6-Chloro-2-[2-(4-fluoro-phenyl)-ethoxymethyl]-3H-pyrido[2,3-d]pyrimidin-4-one,
6-Chloro-2-[2-(3-trifluoromethoxy-phenyl)-ethoxymethyl]-3H-pyrido[2,3-d]pyrimidin-4-one,
6-Chloro-2-[2-(3-chloro-4-fluoro-phenyl)-ethoxymethyl]-3H-pyrido[2,3-d]pyrimidin-4-one,
6-Chloro-2-[2-(4-chloro-phenyl)-ethoxymethyl]-3H-pyrido[2,3-d]pyrimidin-4-one,
3-(3-Fluoro-phenyl)-N-(4-oxo-3,4-dihydro-pyrido[2,3-d]pyrimidin-2-ylmethyl)-propionamide,
2-[2-(3-Chloro-phenyl)-ethoxymethyl]-6-fluoro-3H-pyrido[2,3-d]pyrimidin-4-one,
2-[2-(3-Chloro-phenyl)-ethoxymethyl]-7-fluoro-3H-pyrido[2,3-d]pyrimidin-4-one,
2-(5-Methyl-2-phenyl-oxazol-4-yl)-N-(4-oxo-3,4-dihydro-pyrido[2,3-d]pyrimidin-2-ylmethyl)-acetamide,
2-[1,2,4]Triazol-1-ylmethyl-3H-pyrido[2,3-d]pyrimidin-4-one,
2-(3-Chloro-phenoxy)-N-(4-oxo-3,4-dihydro-pyrido[2,3-d]pyrimidin-2-ylmethyl)-acetamide,
N-(4-Oxo-3,4-dihydro-pyrido[2,3-d]pyrimidin-2-ylmethyl)-2-(pyridin-2-yloxy)-acetamide,
2-[2-(3-Fluoro-phenyl)-ethoxymethyl]-3H-pyrido[2,3-d]pyrimidin-4-one,
2-[2-(3-Methoxy-phenyl)-ethoxymethyl]-3H-pyrido[2,3-d]pyrimidin-4-one,
7-Fluoro-2-[4-(4-fluoro-phenyl)-butyl]-3H-pyrido[2,3-d]pyrimidin-4-one,
7-Fluoro-2-[2-(2-fluoro-phenyl)-ethoxymethyl]-3H-pyrido[2,3-d]pyrimidin-4-one,
N-(6-Fluoro-4-oxo-3,4-dihydro-pyrido[2,3-d]pyrimidin-2-ylmethyl)-3-phenyl-propionamide,
7-Fluoro-2-[2-(3-trifluoromethyl-phenyl)-ethoxymethyl]-3H-pyrido[2,3-d]pyrimidin-4-one,
5-Methyl-2-(5-phenyl-pentyloxy)-3H-pyrido[2,3-d]pyrimidin-4-one,
6-Chloro-2-(3-phenoxy-propoxy)-3H-pyrido[2,3-d]pyrimidin-4-one,
7-Methyl-2-(5-phenyl-pentyloxy)-3H-pyrido[2,3-d]pyrimidin-4-one,
2-[3-(2-Chloro-phenoxy)-propoxy]-5-methyl-3H-pyrido[2,3-d]pyrimidin-4-one,
7-Fluoro-2-[2-(3-fluoro-phenyl)-ethoxymethyl]-3H-pyrido[2,3-d]pyrimidin-4-one,
7-Fluoro-2-[2-(4-fluoro-phenyl)-ethoxymethyl]-3H-pyrido[2,3-d]pyrimidin-4-one,
3-(2-Chloro-phenyl)-N-(4-oxo-3,4-dihydro-pyrido[2,3-d]pyrimidin-2-ylmethyl)-propionamide,
3-(3-Chloro-phenyl)-N-(4-oxo-3,4-dihydro-pyrido[2,3-d]pyrimidin-2-ylmethyl)-propionamide,
2-[2-(2-Chloro-phenyl)-ethoxymethyl]-7-fluoro-3H-pyrido[2,3-d]pyrimidin-4-one,
6-Chloro-2-[2-(2-chloro-phenyl)-ethoxymethyl]-3H-pyrido[2,3-d]pyrimidin-4-one,
6-Fluoro-2-[2-(3-fluoro-phenyl)-ethoxymethyl]-3H-pyrido[2,3-d]pyrimidin-4-one,
6-Chloro-2-[4-(4-fluoro-phenyl)-butyl]-3H-pyrido[2,3-d]pyrimidin-4-one,
2-[2-(2-Chloro-6-fluoro-phenyl)-ethoxymethyl]-7-fluoro-3H-pyrido[2,3-d]pyrimidin-4-one,
2-(2-m-Tolyl-ethoxymethyl)-3H-pyrido[2,3-d]pyrimidin-4-one,
2-[2-(4-Chloro-phenyl)-ethoxymethyl]-7-fluoro-3H-pyrido[2,3-d]pyrimidin-4-one,
3-(4-Chloro-phenyl)-N-(4-oxo-3,4-dihydro-pyrido[2,3-d]pyrimidin-2-ylmethyl)-propionamide,
(6-Fluoro-4-oxo-3,4-dihydro-pyrido[2,3-d]pyrimidin-2-ylmethyl)-carbamic acid benzyl ester,
2-[2-(2,5-Difluoro-phenyl)-ethoxymethyl]-7-fluoro-3H-pyrido[2,3-d]pyrimidin-4-one,
N-(4-Oxo-3,4-dihydro-pyrido[2,3-d]pyrimidin-2-ylmethyl)-3-m-tolyl-propionamide,
7-Fluoro-2-[2-(3-trifluoromethoxy-phenyl)-ethoxymethyl]-3H-pyrido[2,3-d]pyrimidin-4-one,
3-(3-Methoxy-phenyl)-N-(4-oxo-3,4-dihydro-pyrido[2,3-d]pyrimidin-2-ylmethyl)-propionamide,
2-[2-(3-Chloro-4-fluoro-phenyl)-ethoxymethyl]-7-fluoro-3H-pyrido[2,3-d]pyrimidin-4-one,
2-[2-(2,5-Difluoro-phenyl)-ethoxymethyl]-6-fluoro-3H-pyrido[2,3-d]pyrimidin-4-one,
(6-Chloro-4-oxo-3,4-dihydro-pyrido[2,3-d]pyrimidin-2-ylmethyl)-carbamic acid benzyl ester,
(7-Chloro-4-oxo-3,4-dihydro-pyrido[2,3-d]pyrimidin-2-ylmethyl)-carbamic acid benzyl ester,
(7-Fluoro-4-oxo-3,4-dihydro-pyrido[2,3-d]pyrimidin-2-ylmethyl)-carbamic acid benzyl ester,
6-Chloro-2-(2-naphthalen-2-yl-ethoxymethyl)-3H-pyrido[2,3-d]pyrimidin-4-one,
2-[2-(2,5-Difluoro-phenyl)-ethoxymethyl]-6-ethyl-3H-pyrido[2,3-d]pyrimidin-4-one,
2-[2-(3-Chloro-phenyl)-ethoxymethyl]-6-ethyl-3H-pyrido[2,3-d]pyrimidin-4-one,
6-Butyl-2-[2-(3-chloro-phenyl)-ethoxymethyl]-3H-pyrido[2,3-d]pyrimidin-4-one,
6-Butyl-2-[2-(2,5-difluoro-phenyl)-ethoxymethyl]-3H-pyrido[2,3-d]pyrimidin-4-one,
2-[2-(3-Chloro-4-fluoro-phenyl)-ethoxymethyl]-6-ethyl-3H-pyrido[2,3-d]pyrimidin-4-one,
6-Cyclopropyl-2-(4-phenyl-butyl)-3H-pyrido[2,3-d]pyrimidin-4-one,
2-(2-Fluoro-phenyl)-ethanesulfonic acid (4-oxo-3,4-dihydro-pyrido[2,3-d]pyrimidin-2-ylmethyl)-amide,
2-(3-Chloro-phenyl)-ethanesulfonic acid (4-oxo-3,4-dihydro-pyrido[2,3-d]pyrimidin-2-ylmethyl)-amide,
and all pharmaceutically acceptable salts and esters thereof.
Other particularly preferred compounds as defined above are those selected from the group consisting of:
6-Chloro-2-[2-(3-chloro-4-fluoro-phenyl)-ethoxymethyl]-3H-pyrido[2,3-d]pyrimidin-4-one,
2-[2-(3-Chloro-phenyl)-ethoxymethyl]-6-fluoro-3H-pyrido[2,3-d]pyrimidin-4-one,
2-[2-(3-Chloro-phenyl)-ethoxymethyl]-7-fluoro-3H-pyrido[2,3-d]pyrimidin-4-one,
2-(5-Methyl-2-phenyl-oxazol-4-yl)-N-(4-oxo-3,4-dihydro-pyrido[2,3-d]pyrimidin-2-ylmethyl)-acetamide,
6-Chloro-2-(3-phenoxy-propoxy)-3H-pyrido[2,3-d]pyrimidin-4-one, (6-Fluoro-4-oxo-3,4-dihydro-pyrido[2,3-d]pyrimidin-2-yl-methyl)-carbamic acid benzyl ester,
2-[2-(2,5-Difluoro-phenyl)-ethoxymethyl]-6-fluoro-3H-pyrido[2,3-d]pyrimidin-4-one,
2-[2-(2,5-Difluoro-phenyl)-ethoxymethyl]-6-ethyl-3H-pyrido[2,3-d]pyrimidin-4-one,
6-Butyl-2-[2-(2,5-difluoro-phenyl)-ethoxymethyl]-3H-pyrido[2,3-d]pyrimidin-4-one,
2-(2-Fluoro-phenyl)-ethanesulfonic acid (4-oxo-3,4-dihydro-pyrido[2,3-d]pyrimidin-2-ylmethyl)-amide,
and all pharmaceutically acceptable salts and esters thereof.

It will be appreciated that the compounds of general formula (I) in this invention may be derivatised at functional groups to provide derivatives which are capable of conversion back to the parent compound in vivo.

The invention further relates to a process for the manufacture of compounds of formula (I) as defined above, which process comprises converting a compound of formula (II)

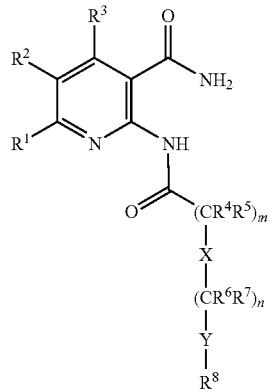

by an intramolecular condensation reaction to the compound of formula (I), wherein $R^1$, $R^2$, $R^3$, $R^4$, $R^5$, $R^6$, $R^7$, $R^8$, m, n, X and Y are as defined in the claims.

The conversion of the compound of formula (II) to the compound of formula (I) via an intramolecular condensation can conveniently be carried out by methods known to the person skilled in the art, for example, with 2-alkaloylamino-nicotinamides (V), under basic conditions using bases such as sodium, potassium or cesium carbonate or sodium or potassium hydroxide in solvents such as ethanol, methanol, water or mixtures thereof at elevated temperatures up to reflux, to give the compounds of formula (I). Alternatively, an acidic cyclization in the presence of p toluene sulfonic acid in a solvent such as toluene at elevated temperatures up to reflux can be employed.

The present invention also relates to compounds of formula (I) as defined above, when prepared by a process as described above.

The compounds of formula (I), which are the subject of this invention, can be manufactured as outlined in Scheme A-C, by the methods given in the examples or by analogous methods. Unless otherwise indicated, $R^1$, $R^2$, $R^3$, $R^4$, $R^5$, $R^6$, $R^7$, $R^8$, $R^9$, $R^{10}$, X, Y, m and n are as described above. The starting materials are either commercially available, described in the literature or can be prepared by methods well known in the art. In some instances, the syntheses require carboxylic acids as starting materials, which can be prepared as outlined in Schemes E-H.

Scheme A

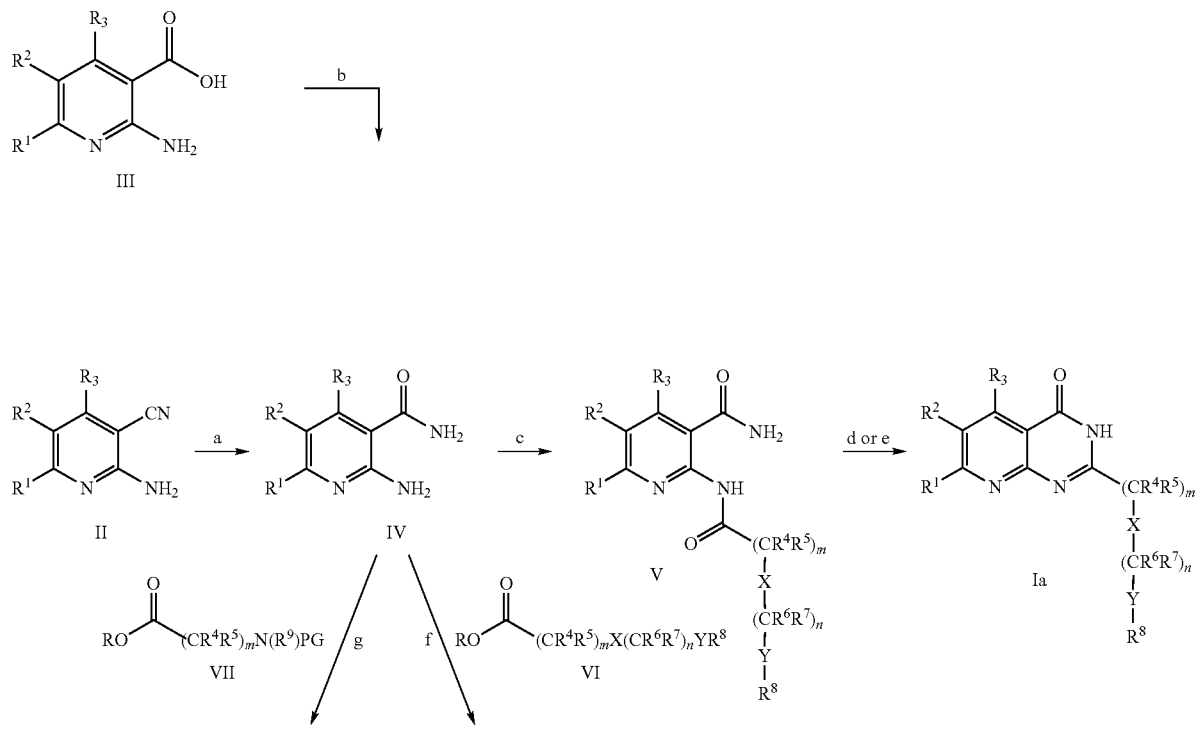

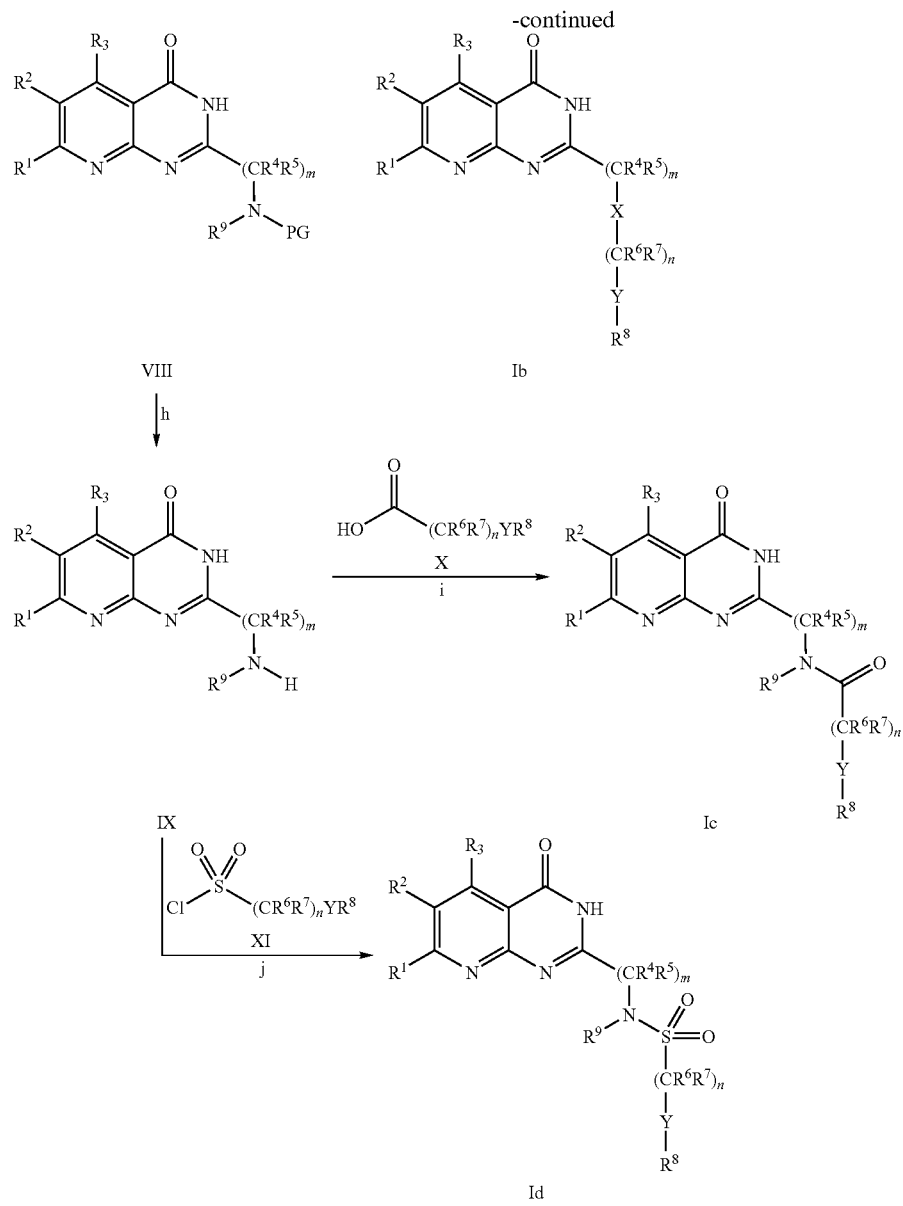

3H-pyrido[2,3-d]pyrimidin-4-ones (Ia) with an alkyl side chain (for m=1-3 or for m=0 and X=single bond) can be prepared by several methods. One method is outlined in scheme A. The starting materials 2-amino-3-cyano-pyridines (II) or 2-amino-nicotinic acids (III) are either commercially available, described in the literature or can be prepared by methods well known to a person skilled in the art. 2-Amino-nicotinamides (IV) can be prepared from 2-amino-nicotino-nitriles (II) by a hydrolysation step, for instance with a source of hydroxide ions, such as sodium or potassium hydroxide, and a catalyst, such as $H_2O_2$, in a suitable solvent, such as water, methanol or ethanol at elevated temperatures (step a). Alternatively, the 2-amino-nicotinamides (IV) might be prepared from the corresponding 2-amino-nicotinic acids (III) by conversion to the corresponding acid chlorides with thionylchloride or oxalylchloride in solvents such as toluene or $CH_2Cl_2$ preferably under reflux conditions and subsequent treatment of the acid chlorides with $NH_4OH$ in solvents such as THF (step b). 2-Amino-nicotinamides (IV) can then be reacted with a suitably activated carboxylic acid, for instance with a carboxylic acid chloride, bromide or carboxylic anhydride, in a suitable solvent, such as THF, DMF or $CH_2Cl_2$ optionally in the presence of a base such as pyridine, DMAP, Huenig's base, triethylamine, $Na_2CO_3$ or ammonium hydroxide to give 2-alkaloylamino-nicotinamides (V) which can be isolated after a usual workup including a purification step, such as column chromatography (step c). Activated carboxylic acids are either commercially available, described in the literature or can be prepared by methods well known to a person skilled in the art. (e.g. RCOCl: 1. $RCO_2H$, $CH_2Cl_2$, $(ClCO)_2$, DMF, rt; or 2. $RCO_2H$, thionyl chloride, reflux, with $R=(CR^4R^5)_m X(CR^6R^7)_n YR^8$). In a final step d, an intramolecular condensation can be carried out with 2-alkaloy-lamino-nicotinamides (V), for instance under basic conditions using bases such as sodium, potassium or cesium carbonate or sodium or potassium hydroxide in solvents such as ethanol, methanol, water or mixtures thereof at elevated temperatures up to reflux, to give 3H-pyrido[2,3-d]pyrimidin-4-ones (Ia) (step d). Alternatively, an acidic cyclization in the presence of p toluene sulfonic acid in a solvent such as toluene at elevated temperatures up to reflux can be employed (step e).

3H-Pyrido[2,3-d]pyrimidin-4-ones (Ib) with an ether side chain (m≠0 and X=O) can be prepared by reacting 2-amino-nicotinamides (IV) with a carboxylic acid ester (VI) (R being e.g. Me, Et, Bn or another suited protecting group as described e.g. in "Protective Groups in Organic Chemistry" by T. W. Greene and P. G. M. Wutts, $2^{nd}$ Ed., 1991, Wiley N.Y.) in the presence of a base, for instance by treatment of a methyl ester (VI) (R=Me) with LiHMDS (lithium hexamethyldisilazide) in THF at ambient temperature (step f). Esters (VI) are either commercially available, described in the literature, can be prepared by methods described in schemes E)-H) (e.g. via esterifications of carboxylic acids (III) in scheme E) or carboxylic acids (V) in scheme F) by methods known in the art, compounds (IV) in scheme G) or compounds (III) in scheme H)) or by methods well known to a person skilled in the art.

Protected amines (VIII) (m≠0, $R^9$ is either a residue as described above except for H or a protecting group) can be prepared from 2-amino-nicotinamides (IV) and carboxylic acid esters (VII) in close analogy to compounds (Ib) (step g). Alternatively, analogous acid chlorides ClC(O)(CR$^4$R$^5$)$_m$N(R$^9$)PG can be reacted with 2-amino-nicotinamides (IV) as described in steps c)-e) to form compounds (VIII). Removal of the amine protecting group(s) yields amines (IX) ($R^9$ as described above) (step h). Methods for the protection and deprotection of amines are well known to a person skilled in the art and described in the literature, e.g in "Protective Groups in Organic Chemistry" by T. W. Greene and P. G. M. Wutts, $2^{nd}$ Ed., 1991, Wiley N.Y. For instance, phthalyl glycyl chloride can be reacted with a 2-amino-nicotinamide (IV) in the presence of a base like pyridine in a solvent like dichloromethane, preferably at temperatures between 0° C. and ambient temperature and subsequent treatment at elevated temperatures in a solvent like DMF in the presence of a base like ethyl-diisopropyl-amine to form cyclization products (VIII) with $R^9$ and PG together forming a phthalimide. Removal of the phthaloyl protecting group can for example be achieved by treatment with hydrazine in a solvent like ethanol preferably at elevated temperatures to form a primary amine (IX) ($R^9$=H). Esters (VII) and corresponding acid chlorides ClC(O)(CR$^4$R$^5$)$_m$N(R$^9$)PG are either commercially available, described in the literature or can be prepared by methods well known to a person skilled in the art. Amines (IX) can be condensed with suitibly activated carboxylic acids (X) to form final products (Ic) (m≠0) (step i). Activated carboxylic acids are either commercially available, described in the literature or can be prepared by methods well known to a person skilled in the art. (e.g. carboxylic acid chlorides: 1. carboxylic acid, $CH_2Cl_2$, (ClCO)$_2$, DMF, rt; or 2. carboxylic acid, thionyl chloride, reflux). Alternatively, carboxylic acids (X) can be in situ activated and transformed into the final products (Ic) using e.g. N-(3-dimethylaminopropyl)-N'-ethyl-carbodiimide-hydrochloride, TBTU (O-(benzotriazol-1-yl)-N,N,N',N'-tetramethyluronium tetrafluoroborate) or BOP (benzotriazol-1-yloxytris(dimethylamino)phosphonium hexafluorophoshate) in the presence of a base such as ethyl-diisopropyl-amine, triethylamine, N-methylmorpholine optionally in the presence of 4-dimethylamino-pyridine or HOBt (1-hydroxybenzo-triazole) in solvents such as dichloromethane, DMF, DMA or dioxane at temperatures between 0° C. and ambient temperature. Condensation of amines (IX) with sulfonic acid chlorides (XI) gives the final products (Id) (m≠0) (step j). Sulfone amide formation can be carried out following methods described in the literature, e.g. reacting amine (IX) with sulfonic acid chloride (XI) in the presence of a base like ethyl-diisopropyl-amine in a solvent like dichloromethane preferably at temperatures between 0° C. and ambient temperature. Sulfonic acid chlorides are either commercially available, described in the literature or can be prepared by methods well known to a person skilled in the art. Alternatively, amines (IX) can be reacted with isocyanides to form final products (I) with X=NHC(O)NH as described in step g of scheme B or with chloroformates to form final products (I) with X=NHC(O)O as described in step h of scheme B.

If one of the starting materials, compounds of formula (IV), the activated carboxylic acid used to form compounds (V), esters (VI), esters (VII), carboxylic acids (X) or sulfonic acid chlorides (XI) contains one or more functional groups which are not stable or are reactive under the reaction conditions of one or more reaction steps, appropriate protecting groups (PG) (as described e.g. in "Protective Groups in Organic Chemistry" by T. W. Greene and P. G. M. Wutts, $2^{nd}$ Ed., 1991, Wiley N.Y.) can be introduced before the critical step applying methods well known in the art. Such protecting groups can be removed at a later stage of the synthesis using standard methods described in the literature.

If compounds (IV), esters (VI), esters (VII), carboxylic acids (X), sulfonic acid chlorides (XI) and/or the activated carboxylic acid used to form compounds (V) contain chiral centers, pyrido pyrimidinones (Ia), (Ib), (Ic) or (Id) can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization with optically pure acids or by separation of the antipodes by specific chromatographic methods using either a chiral adsorbens or a chiral eluent.

Scheme B

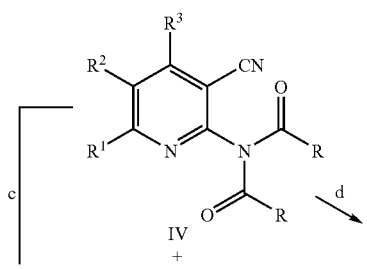

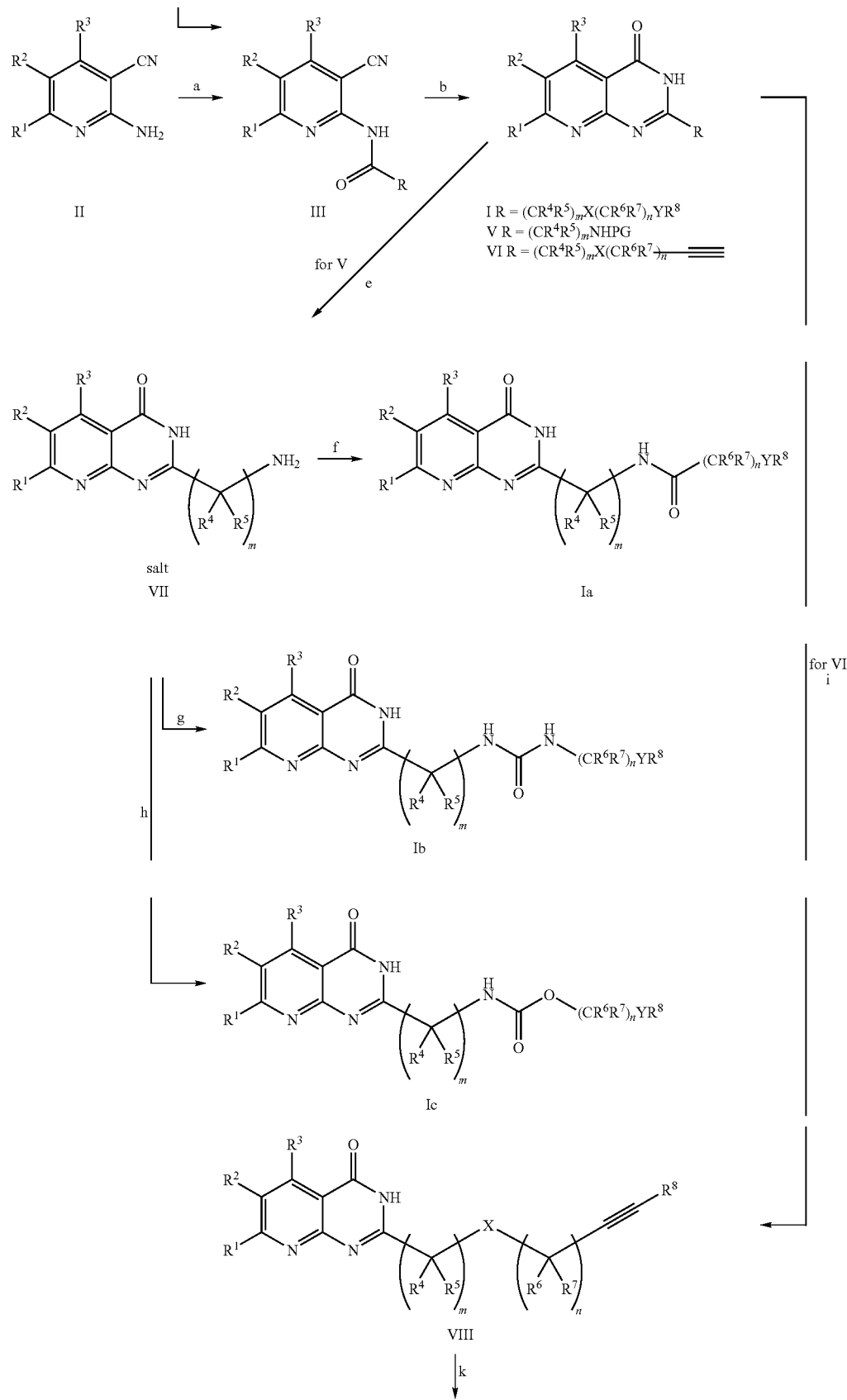

-continued

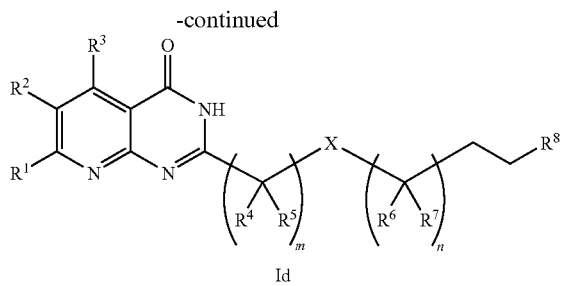

Id

Another method to obtain 2-alkyl-3H-pyrido[2,3-d]pyrimidin-4-ones (I) (for m=1-3 or for m=0 and X=single bond) using 2-amino-nicotinonitriles (II) as starting materials is outlined in Scheme B: 2-amino-nicotinonitriles (II) are reacted with a suitably activated carboxylic acid, for instance with a carboxylic acid chloride, bromide or carboxylic anhydride, in a suitable solvent, such as THF, DMF or $CH_2Cl_2$ optionally in the presence of a base such as pyridine, DMAP, Huenig's base, triethylamine, $Na_2CO_3$ or ammonium hydroxide to give N-acylated 2-amino-3-cyano-pyridines (III) after the usual workup and purification (step a). In some cases the corresponding N,N-diacylated 2-amino-3-cyano-pyridines (IV) can be isolated as well. 2-Alkyl-3H-pyrido[2,3-d]pyrimidin-4-ones (I) can be obtained from III by a hydrolysation of the nitrile functionality with a subsequent intramolecular condensation (step b). This reaction can be carried out by treatment of III with a source of hydroxide ions, such as sodium or potassium hydroxide or potassium carbonate, and a catalyst, such as $H_2O_2$, in a suitable solvent, such as water, methanol or ethanol at elevated temperatures. N,N-diacylated 2-amino-3-cyano-pyridines (IV) can be converted to the monoacylated pyridines (III), for instance by using aqueous calcium carbonate as described in the literature (see e.g. B. Abarca et al. *Tetrahedron* 1989, 45, 7041-7048) (step c). Alternatively, 2-alkyl-3H-pyrido[2,3-d]pyrimidin-4-ones (I) might be prepared from the N,N-diacylated 2-amino-3-cyano-pyridines (IV) in a one pot sequence, by a selective mono-hydolysis followed by a hydrolysation of the nitrile functionality with a subsequent intramolecular cyclisation using sodium or potassium hydroxide or potassium carbonate, and a catalyst, such as $H_2O_2$, in a suitable solvent, such as water, methanol or ethanol at elevated temperatures (step d).

In the cases in which 3H-pyrido[2,3-d]pyrimidin-4-ones (V) or (VI) are isolated after the cyclization the compounds can be modified further, optionally using one or more protecting groups which can be removed at an appropriate time point of the synthesis (steps e-k). Further modifications of derivatives (V) involve deprotection of the amine moiety to give 2-aminoalkyl-3H-pyrido[2,3-d]pyrimidin-4-ones (VII). The protecting group is removed under reaction conditions depending on the nature of the protecting group (step e). For instance, a benzyl carbamate can be removed under acidic conditions, for example by treatment with HBr/AcOH to provide amines (VII) as salts, which can serve as building blocks for further modifications. In the case of a BOC protecting group, the cleavage may be accomplished by treatment with TFA in $CH_2Cl_2$. VII can be transformed with a suitably activated carboxylic acid, for instance a carboxylic acid activated in situ by an activating agent such as EDCI optionally in the presence of HOBt and a base such as Huenig's base, $NEt_3$, NMM in $CH_2Cl_2$, DMF, DMA or dioxane, to 3H-pyrido[2,3-d]pyrimidin-4-ones (Ia), which can be obtained from the reaction mixture by a conventional workup (step f). Similarly, 3H-pyrido[2,3-d]pyrimidin-4-ones (Ib) can be obtained by reaction of VII with an isocyanide in solvents such as pyridine, dichloromethane at ambient temperatures up to reflux conditions (step g) followed by a conventional workup and purification. 3H-pyrido[2,3-d]pyrimidin-4-ones (Ic) can be obtained from VII (step h) by treatment with a chloroformate and a base, such as triethylamine, NMM or Huenig's base, in a solvent such as dichloromethane, followed by a conventional workup and purification. Alternatively, amines (VII) can be condensed with sulfonic acid chlorides $ClSO_2(CR^6R^7)_nYR^8$ to yield 3H-pyrido[2,3-d]pyrimidin-4-ones (I) with $X=N(R^9)SO_2$ as described in step j of scheme A. Sulfonic acid chlorides $ClSO_2(CR^6R^7)_nYR^8$ are either commercially available, described in the literature or can be prepared by methods well known to a person skilled in the art. Sulfone amide formation can be carried out following methods described in the literature, e.g. reacting amine (VII) with sulfonic acid chloride $ClSO_2(CR^6R^7)_nYR^8$ in the presence of a base like ethyl-diisopropyl-amine in a solvent like dichloromethane preferably at temperatures between 0° C. and ambient temperature. If the 2-substituent is appropriately functionalized with a terminal acetylene motif as in derivatives (VI), Sonogashira reactions can be carried out according to literature-described procedures with halogenated aromatic reactants such as iodoarenes, bromoarenes or chloroarenes or with aromatic triflates (step i). The conditions of the Sonogashira reaction might involve a palladium catalyst and a copper catalyst such as $Pd(PPh_3)_4/CuI$ or $Pd(OAc)_2/CuI$ or $PdCl_2(PPh_3)_2/CuI$, and a base, for instance an amine such as triethylamine or piperidine, which might also serve as a solvent, alternatively a solvent such as THF might be used. After a conventional workup and purification, an acetylenic compound (VIII) is obtained. This can be further transformed (step k), by a reduction of the acetylenic bond under an atmosphere of hydrogen, with a catalyst such as palladium on charcoal in a solvent such as ethanol, to give 3H-pyrido[2,3-d]pyrimidin-4-ones (Id).

If one of the starting materials, compounds of formula (II) or the substituents introduced in steps g, h, f or i contain one or more functional groups which are not stable or are reactive under the reaction conditions, appropriate protecting groups (PG) (as described e.g. in "Protective Groups in Organic Chemistry" by T. W. Greene and P. G. M. Wutts, $2^{nd}$ Ed., 1991, Wiley N.Y.) can be introduced before the critical step applying methods well known in the art. Such protecting groups can be removed at a later stage of the synthesis using standard methods described in the literature.

If compounds (III) or (IV) and/or the substituents introduced in steps g, h, f or i contain chiral centers, pyrido pyrimidinones (I), (Ia), (Ib), (Ic) or (Id) can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization with optically pure acids or by separation of the antipodes by specific chromatographic methods using either a chiral adsorbens or a chiral eluent.

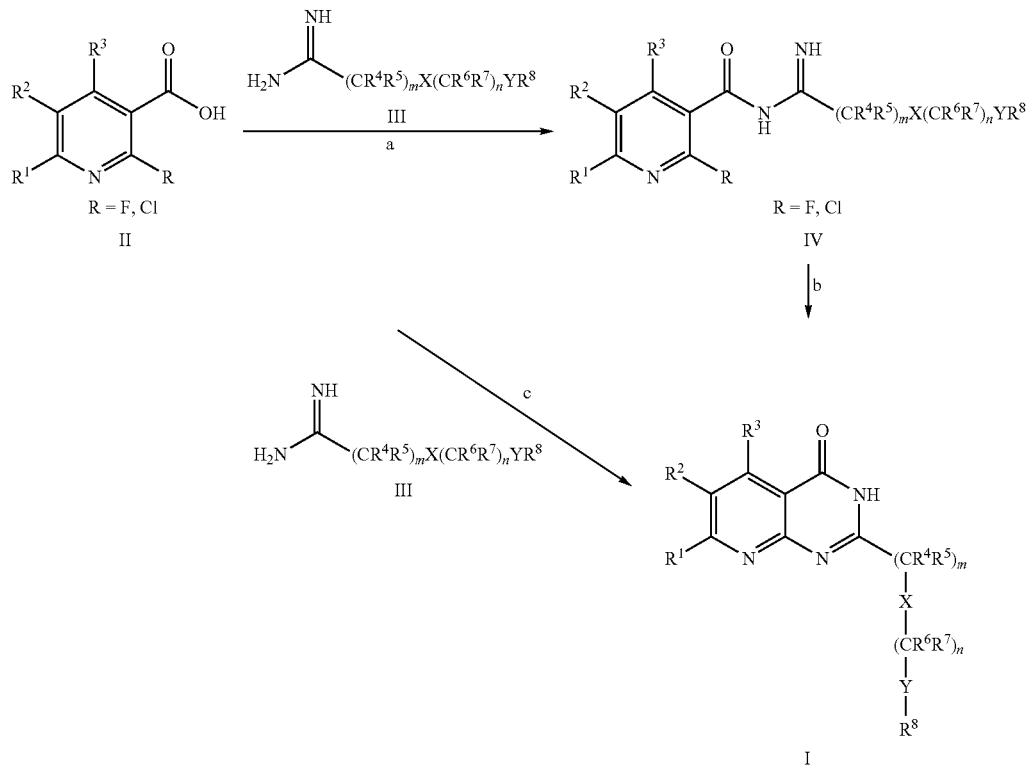

3H-Pyrido[2,3-d]pyrimidin-4-ones (I) (for m=1-3 or for m=0 and X=single bond) can be synthesized starting from 2-fluoro-nicotinic acids (II) or 2-chloro-nicotinic acids (II) as outlined in scheme C: carboxylic acids (II) can be condensed—after suitable activation—with amidines (III) or the corresponding amidine salts to give acylamidines (IV) under reaction conditions well known to a person skilled in the art (step a). If the activated carboxylic acid is for instance a carboxylic acid chloride, bromide or carboxylic anhydride the reaction can be performed in a solvent such as dichloromethane, optionally in the presence of a base such as triethylamine, ethyl-diisopropyl-amine or N-ethylmorpholine at temperatures between 0° C. and ambient temperature. Activated carboxylic acids are either commercially available, described in the literature or can be prepared by methods well known to a person skilled in the art. (e.g. carboxylic acid chlorides: 1. carboxylic acid, $CH_2Cl_2$, $(ClCO)_2$, DMF, rt; or 2. carboxylic acid, thionyl chloride, reflux). Alternatively, carboxylic acids (II) can be in situ activated and transformed into acylamidines (IV) using e.g. N-(3-dimethylaminopropyl)-N'-ethyl-carbodiimide-hydrochloride, TBTU (O-(benzotriazol-1-yl)-N,N,N',N'-tetramethyluronium tetrafluoroborate) or BOP (benzotriazol-1-yloxytris-(dimethylamino)phosphonium hexafluorophoshate) in the presence of a base such as ethyl-diisopropyl-amine, triethylamine, N-methylmorpholine optionally in the presence of 4-dimethylamino-pyridine or HOBt (1-hydroxybenzo-triazole) in solvents such as dichloromethane, DMF, DMA or dioxane preferably at temperatures between 0° C. and ambient temperature. Amidines (III) or its corresponding salts are either commercially available, described in the literature, or can be synthesized by methods well known to a person skilled in the art. For instance, compounds (III) can be synthesized by treating the corresponding carboxylic acid esters (e.g. compounds (IV) in scheme G) or compounds (III) in scheme H) or esters which can be synthesized via esterifications of carboxylic acids (III) in scheme E) or carboxylic acids (V) in scheme F by methods known in the art) with trimethylaluminum and ammonium chloride in a solvent like toluene, preferably at temperatures between 0° C. and ambient temperature. Cyclisation of acylamidines (IV) to 3H-pyrido[2,3-d]pyrimidin-4-ones (I) can for example be achieved by treatment with a base like potassium tert-butylate or potassium carbonate in a solvent like DMSO or DMF at temperatures between 0° C. and the reflux temperature of the solvent (step b). In cases were 2-fluoro-nicotinic acids (II) (R=F) are used as starting materials, activated carboxylic acids and amidines (III) provide directly the final products (I) without prior isolation of acyl amidines (IV) (step c). Preferably, these reactions are performed by treating 2-fluoro substituted carboxylic acid chlorides and amidines (III) in the presence of a base like N,N-diisopropyl ethyl amine in a solvent like acetonitrile at temperatures between ambient temperature and the reflux temperature of the solvent.

If one of the starting materials, compounds of formula (II) or (III) contain one or more functional groups which are not stable or are reactive under the reaction conditions, appropriate protecting groups (PG) (as described e.g. in "Protective Groups in Organic Chemistry" by T. W. Greene and P. G. M. Wutts, 2$^{nd}$ Ed., 1991, Wiley N.Y.) can be introduced before the critical step applying methods well known in the art. Such protecting groups can be removed at a later stage of the synthesis using standard methods described in the literature. Optionally, 3H-pyrido[2,3-d]pyrimidin-4-ones carrying a protecting group can be further elaborated after the cyclisation (step b or c) to the final products as described in schemes A and B.

If compounds (II) or (III) contain chiral centers, pyrido pyrimidinones (I) can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization with optically pure acids or by separation of the antipodes by specific chromatographic methods using either a chiral adsorbens or a chiral eluent.

(V) (step c). Compounds (V) can alternatively be prepared from substituted 2-amino-nicotinic acids (IX) and urea as described in the literature (compare e.g. C. Sanmartin et al. *Bioorg. Med. Chem.* 2005, 13, 2031-2044; step g). Substituted 2-amino-nicotinic acids (IX) are commercial, known in the literature or can be prepared by a person skilled in the art. Conversion of 2,4-dioxo pyrimidines (V) into the corresponding 2,4-dichloro pyrimidines (VI) can e.g. be achieved via treatment with phosphorous oxychloride, preferably under reflux conditions (step d). Selective displacement of the 4-chloro atom of compounds (VI), e.g. using aqueous sodium hydroxide at ambient temperature, leads to 2-chloro-4-oxy pyrimidines (VII) (step e). Compounds (VII) can be reacted with alcohols (VIII) to give the final compounds (I) (step f). This reaction can be performed in the presence of a suitable, non-nucleophilic base such as KOtBu in solvents like DMSO at temperatures between ambient temperature and the reflux temperature of the solvent, optionally using a microwave

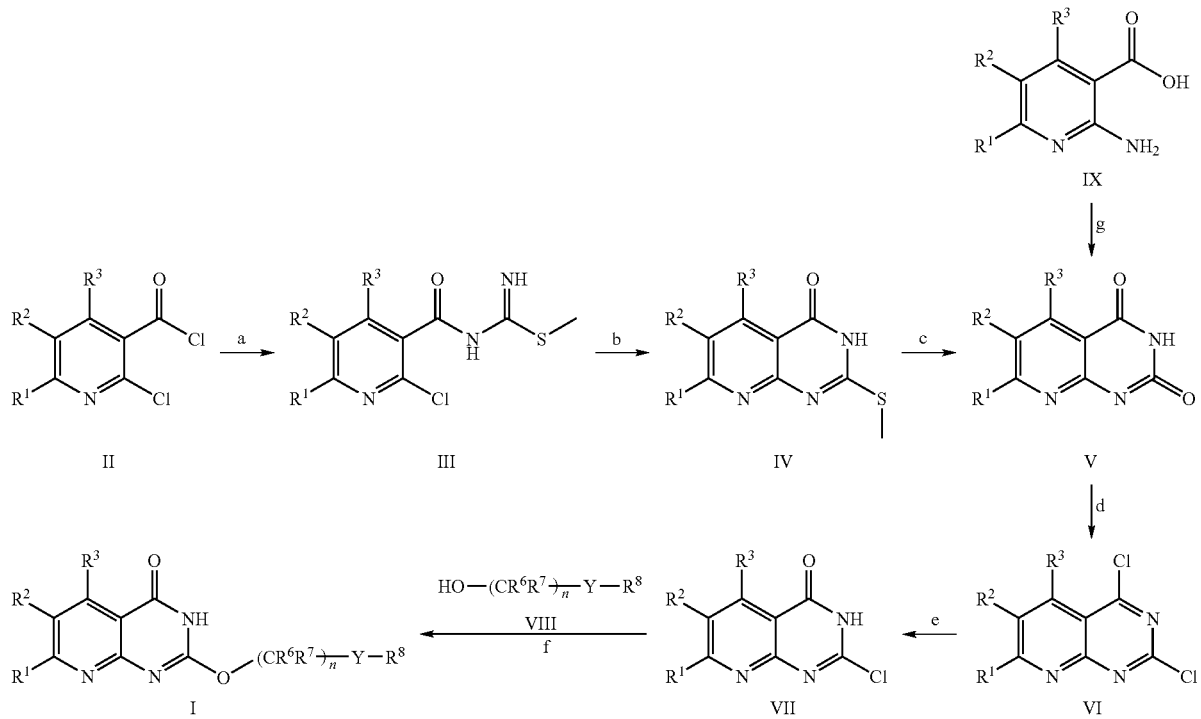

Scheme D

2-Alkoxy-3H-pyrido[2,3-d]pyrimidin-4-ones I (for m=0, X=O) can be prepared as outlined in Scheme D: 2-Chloronicotinic acid chlorides (II) can be prepared from the corresponding 2-chloronicotinic acids, which are commercial, known or can be prepared by a person skilled in the art. Reaction of acid chlorides (II) with 2-methyl-isothiourea in a solvent like chloroform and in the presence of a base like pyridine at a temperature between 0° C. and the reflux temperature of the solvent gives acyl pseudothioureas (III) (step a). Cyclisation of compounds (III) in a solvent like e.g. DMF in a temperature range between ambient temperature and the reflux temperature of the solvent provides pyrimidine derivatives (IV) (step b). Treatment of compounds (IV) with aqueous acid, e.g. with hydrochloric acid preferably at elevated temperatures, leads to the formation of 2,4-dioxo pyrimidines oven. 2-Alkoxy-3H-pyrido[2,3-d]pyrimidin-4-ones (I) can then be isolated from the reaction mixture, for instance by HPLC.

If one of the starting materials, compounds of formula (II) or (IX) or alcohols (VIII) contain one or more functional groups which are not stable or are reactive under the reaction conditions of one or more reaction steps, appropriate protecting groups (PG) (as described e.g. in "Protective Groups in Organic Chemistry" by T. W. Greene and P. G. M. Wutts, 2$^{nd}$ Ed., 1991, Wiley N.Y.) can be introduced before the critical step applying methods well known in the art. Such protecting groups can be removed at a later stage of the synthesis using standard methods described in the literature.

If compounds (II) or (IX) and/or alcohols (VIII) contain chiral centers, pyrido pyrimidinones (I) can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization with optically pure acids or by separation of the antipodes by specific chromatographic methods using either a chiral adsorbens or a chiral eluent.

Scheme E: Preparation of carboxylic acids used in Scheme A and B (1)

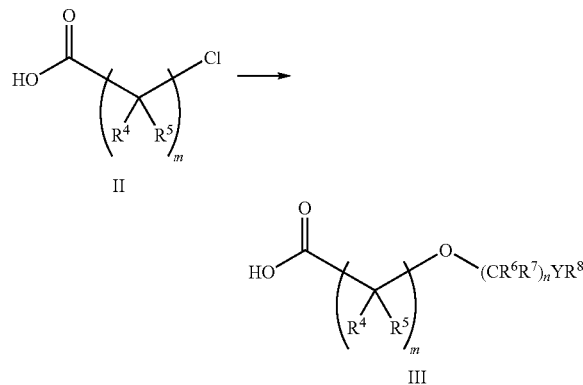

Alkoxyalkanoic acids (III) (with m≠0) can be prepared as outlined in scheme E: A chloroalkanoic acid (II) is reacted with an alcoholate in a suitable solvent, such as DMF, THF or mixtures thereof, typically at elevated temperature. The alcoholate may be pre-pared by treatment of the corresponding alcohol with a suitable base, such as NaH or KOtBu. After a workup that is suitable for weakly acidic organic substances, the alkoxyalkanoic acids (III) are usually obtained in a pure enough form to be used in the next step with no further purification.

Compounds (III) can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization with optically pure amines such as e. g. (R) or (S)-1-phenyl-ethylamine, (R) or (S)-1-naphthalen-1-yl-ethylamine, brucine, quinine or quinidine or by separation of the antipodes by specific chromatographic methods using either a chiral adsorbens or a chiral eluent. Optionally, compounds (III) can be synthesized in a stereoselective manner applying methods well known to a person skilled in the art.

Scheme F: Preparation of carboxylic acids used in Scheme A and B (2)

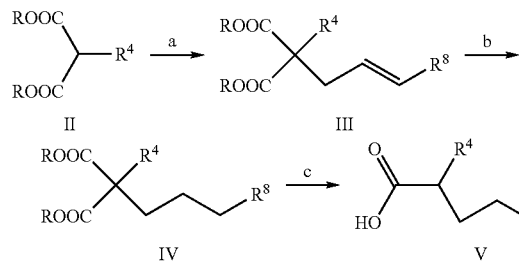

5-Aryl-pentanoic acids (V), which are substituted in the 2-position by hydrogen, an alkyl chain or a fluorinated alkyl chain, can be prepared by the method outlined in scheme F: In a first step a, deprotonated, suitably substituted malonate (II) (R being e.g. Me, Et, Bn or another suited protecting group as described e.g. in "Protective Groups in Organic Chemistry" by T. W. Greene and P. G. M. Wutts, $2^{nd}$ Ed., 1991, Wiley N.Y.) is reacted with triphenylphosphonium bromide and a (substituted) aryl aldehyde in a suitable solvent, such as DMF or DMSO, typically at elevated temperature. Substituted malonates (II) are easily obtained, either commercially or by well-known procedures, and are easily deprotonated by a suitable base, such as NaH, KOtBu, NaOMe or NaOEt, in a suitable solvent, such as diethyl ether or THF. The product (III) can be obtained from the reaction mixture by a usual workup including a purification step, for instance column chromatography. 2-Substituted 2-(3-aryl-allyl)-malonic acid esters (III) can be reduced to the corresponding 2-(3-aryl-propyl)-malonic acid esters (IV) in a suitable solvent, such as methanol, ethanol or EtOAc, under an atmosphere of hydrogen, and with a suitable catalyst, such as palladium on charcoal (step b). Upon completion of the reaction, filtration and evaporation of the solvent might be sufficient to obtain the product (IV) in pure form. 2-Substituted 5-aryl-pentanoic acids (V) can be obtained from (IV) by a step commonly known as "saponification/decarboxylation" (step c): IV is heated together with an alkali hydroxide, such as potassium, sodium or lithium hydroxide in a suitable solvent, such as ethanol. Depending on the nature of R, a two step procedure: i) removal of the ester protecting group (as described e.g. in "Protective Groups in Organic Chemistry" by T. W. Greene and P. G. M. Wutts, $2^{nd}$ Ed., 1991, Wiley N.Y.) and ii) decarboxylation to give compounds (V) might be appropriate. After evaporation of the solvent, a workup that is suitable for weakly acidic organic substances, and a purification step, 2-substituted 5-aryl-pentanoic acids (V) are obtained from the reaction mixture.

Compounds (V) can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization with optically pure amines such as e. g. (R) or (S)-1-phenyl-ethylamine, (R) or (S)-1-naphthalen-1-yl-ethylamine, brucine, quinine or quinidine or by separation of the antipodes by specific chromatographic methods using either a chiral adsorbens or a chiral eluent. Optionally, compounds (V) can be synthesized in a stereoselective manner applying methods well known to a person skilled in the art.

Scheme G: Preparation of carboxylic acids used in Scheme A and B (3)

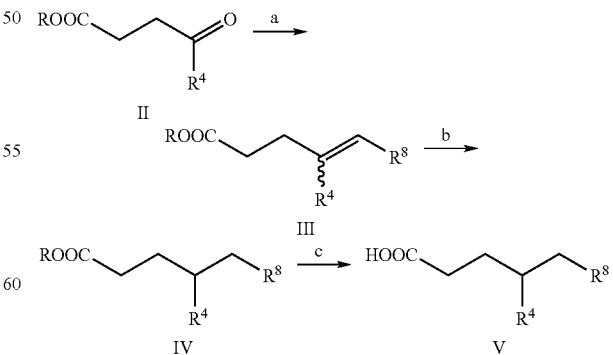

4-Alkyl or 4-fluoroalkyl-5-aryl-pentanoic acids (V) can be prepared as outlined in Scheme G: In a first step a, which is commonly known as a Wittig reaction, a suitable base such as KOtBu or sodium ethanolate is added to an aryl triphenyl phosponium salt (Wittig salt) in a suitable solvent, such as ethanol or THF. The mixture is stirred for some time at a suitable temperature to allow for the formation of the well-known "ylide"-intermediate of the Wittig reaction, before ethyl levulinate or a similar, suitably substituted γ-ketoacid (II) is added to the mixture (R being e.g. Me, Et, Bn or another suited protecting group as described e.g. in "Protective Groups in Organic Chemistry" by T. W. Greene and P. G. M. Wutts, $2^{nd}$ Ed., 1991, Wiley N.Y.), and the mixture is kept at a temperature that is dependent on the nature of the employed Wittig reagent. III is obtained from the reaction mixture after the usual workup and a purification step, for instance column chromatography. In a next step b, the obtained alkenoic acid ester (III) can be reduced under an atmosphere of hydrogen, with a catalyst such as palladium on charcoal, in a solvent such as ethanol or EtOAc. Filtration and evaporation of the solvent might be sufficient to obtain the product (IV) in pure form. In a saponification step c, the obtained IV can be saponified with an alkali hydroxide in a suitable solvent, such as potassium, sodium or lithium hydroxide in solvents such as ethanol, methanol or THF or mixtures thereof, to give a 4-alkyl or a 4-fluoroalkyl-5-aryl-pentanoic acid (V) after a workup that is suitable for weakly acidic organic substances. Depending on the nature of R, an alternative procedure to cleave the ester (IV) might be appropriate (compare e.g. "Protective Groups in Organic Chemistry" by T. W. Greene and P. G. M. Wutts, $2^{nd}$ Ed., 1991, Wiley N.Y.).

Compounds (V) can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization with optically pure amines such as e. g. (R) or (S)-1-phenyl-ethylamine, (R) or (S)-1-naphthalen-1-yl-ethylamine, brucine, quinine or quinidine or by separation of the antipodes by specific chromatographic methods using either a chiral adsorbens or a chiral eluent. Optionally, compounds (V) can be synthesized in a stereoselective manner applying methods well known to a person skilled in the art.

Scheme H: Preparation of carboxylic acids used in Scheme A and B (4)

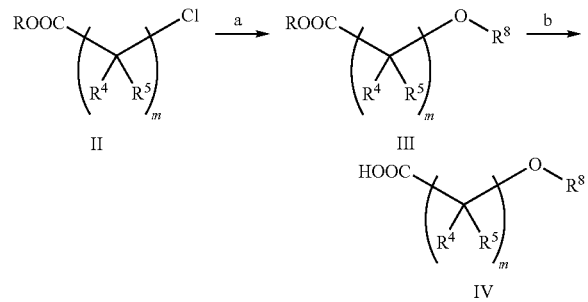

Aryloxy-alkanoic acids (IV) (with m≠0) can be prepared as outlined in Scheme H: In a first step a, a suitable base such as sodium ethanolate, sodium methanolate or KOtBu is added to a suitably substituted phenol and ethyl chloroalkanoate (II) in a solvent such as ethanol (R being e.g. Me, Et, Bn or another suited protecting group as described e.g. in "Protective Groups in Organic Chemistry" by T. W. Greene and P. G. M. Wutts, $2^{nd}$ Ed., 1991, Wiley N.Y.). After completion of the reaction, which might occur at elevated temperature, the mixture is worked up in the usual way. After evaporation of the solvent, a residue is obtained from which the product (III) can be isolated, for instance by column chromatography. In a next step b, the obtained aryloxy-alkanoic acid ester is saponified, for instance by treatment with an alkali hydroxide, such as potassium, sodium or lithium hydroxide, in a suitable solvent, such as ethanol, methanol or THF or mixtures thereof. A workup that is suitable for weakly acidic organic substances then gives aryloxy-alkanoic acids (IV). Depending on the nature of R, an alternative procedure to cleave the ester (III) might be appropriate (compare e.g. "Protective Groups in Organic Chemistry" by T. W. Greene and P. G. M. Wutts, $2^{nd}$ Ed., 1991, Wiley N.Y.).

Compounds (IV) can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization with optically pure amines such as e. g. (R) or (S)-1-phenyl-ethylamine, (R) or (S)-1-naphthalen-1-yl-ethylamine, brucine, quinine or quinidine or by separation of the antipodes by specific chromatographic methods using either a chiral adsorbens or a chiral eluent. Optionally, compounds (IV) can be synthesized in a stereoselective manner applying methods well known to a person skilled in the art.

The corresponding salts with acids can be obtained by standard methods known to the person skilled in the art, e.g. by dissolving the compound of formula(I) in a suitable solvent such as e.g. dioxan or THF and adding an appropriate amount of the corresponding acid. The products can usually be isolated by filtration or by chromatography. The conversion of a compound of formula (I) into a pharmaceutically acceptable salt with a base can be carried out by treatment of such a compound with such a bases. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation.

The conversion of compounds of formula (I) into pharmaceutically acceptable esters can be carried out e.g. by treatment of a suitable carboxy group present in the molecule with a suitable alcohol using e.g. a condensating reagent such as benzotriazol-1-yloxytris(dimethylamino)phosphonium hexafluorophosphate (BOP), N,N-dicylohexylcarbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluorborate (TBTU). Pharmaceutically acceptable esters can furthermore be prepared by treatment of a suitable hydroxy group present in the molecule with a suitable acid, optionally or if necessary in the presence of a condensating agent as described above.

Insofar as their preparation is not described in the examples, the compounds of formula (I) as well as all intermediate products can be prepared according to analogous methods or according to the methods set forth above. Starting materials are commercially available or known in the art.

As described above, the compounds of formula (I) of the present invention can be used as pharmaceutical compositions for the treatment and/or prevention of diseases which are modulated by HM74A agonists. Examples of such diseases are increased lipid and cholesterol levels, particularly dyslipidemia, low HDL-cholesterol, atherosclerotic diseases, hypertriglyceridemia, thrombosis, angina pectoris, peripheral vascular disease, stroke, diabetes, particularly non-insulin dependent diabetes mellitus, metabolic syndrome, Alzheimer's disease, Parkinson's disease, schizophrenia, sepsis, inflammatory diseases (such as e.g. asthma, arthritis, colitis, pancreatitis, cholestasis/fibrosis of the liver, and diseases that have an inflammatory component such as e.g. Alzheimer's disease or impaired/improvable cognitive function). The use as pharmaceutical composition for the treatment of atherosclerosis, low HDL cholesterol levels, non-insulin dependent diabetes mellitus, and the metabolic syndrome is preferred.

The invention therefore also relates to pharmaceutical compositions comprising a compound as described above and a pharmaceutically acceptable carrier and/or adjuvant.

Further, the invention relates to compounds as described above for use as therapeutic active substances, especially as therapeutic active substances for the treatment and/or prevention of diseases which are modulated by HM74A agonists, particularly as therapeutically active substances for the treatment and/or prevention of increased lipid levels, increased cholesterol levels, atherosclerotic diseases, dyslipidemia, low HDL-cholesterol, hypertriglyceridemia, thrombosis, angina pectoris, peripheral vascular disease, stroke, diabetes, non-insulin dependent diabetes mellitus, metabolic syndrome, Alzheimer's disease, Parkinson's disease, schizophrenia, impaired or improvable cognitive function, sepsis, inflammatory diseases, asthma, arthritis, colitis, pancreatitis and cholestasis/fibrosis of the liver.

In another embodiment, the invention relates to a method for the treatment and/or prevention of diseases which are modulated by HM74A agonists, particularly for the treatment and/or prevention of increased lipid levels, increased cholesterol levels, atherosclerotic diseases, dyslipidemia, low HDL-cholesterol, hypertriglyceridemia, thrombosis, angina pectoris, peripheral vascular disease, stroke, diabetes, non-insulin dependent diabetes mellitus, metabolic syndrome, Alzheimer's disease, Parkinson's disease, schizophrenia, impaired or improvable cognitive function, sepsis, inflammatory diseases, asthma, arthritis, colitis, pancreatitis and cholestasis/fibrosis of the liver, which method comprises administering a compound as described above to a human or animal.

The invention further relates to the use of compounds as defined above for the treatment and/or prevention of diseases which are modulated by HM74A agonists, particularly for the treatment and/or prevention of increased lipid levels, increased cholesterol levels, atherosclerotic diseases, dyslipidemia, low HDL-cholesterol, hypertriglyceridemia, thrombosis, angina pectoris, peripheral vascular disease, stroke, diabetes, non-insulin dependent diabetes mellitus, metabolic syndrome, Alzheimer's disease, Parkinson's disease, schizophrenia, impaired or improvable cognitive function, sepsis, inflammatory diseases, asthma, arthritis, colitis, pancreatitis and cholestasis/fibrosis of the liver.

In addition, the invention relates to the use of compounds as described above for the preparation of pharmaceutical compositions for the treatment and/or prevention of diseases which are modulated by HM74A agonists, particularly for the treatment and/or prevention of increased lipid levels, increased cholesterol levels, atherosclerotic diseases, dyslipidemia, low HDL-cholesterol, hypertriglyceridemia, thrombosis, angina pectoris, peripheral vascular disease, stroke, diabetes, non-insulin dependent diabetes mellitus, metabolic syndrome, Alzheimer's disease, Parkinson's disease, schizophrenia, impaired or improvable cognitive function, sepsis, inflammatory diseases, asthma, arthritis, colitis, pancreatitis and cholestasis/fibrosis of the liver. Such pharmaceutical compositions comprise a compound as described above.

Prevention and/or treatment of atherosclerosis, low HDL cholesterol levels, non-insulin dependent diabetes mellitus, and the metabolic syndrome is preferred.

The following tests were carried out in order to determine the biological activity of the compounds of formula (I).

Primary Radiolabelled Ligand Competition Binding Assay

Nicotinic acid binding assays were performed with membrane preparations. A cell pellet containing $1 \times 10^8$ HEK-293 cells, stably transfected with the HM74A receptor, was resuspended in 3 ml of ice cold Dounce Buffer (10 mM Tris-Cl pH 7.6, 0.5 mM $MgCl_2$) supplemented with Roche protease inhibitor cocktail and homogenized at high speed on a Polytron homogenizer two times for 20 sec on ice. Nuclei and unbroken cells were removed by centrifugation for 5 min at $1,000 \times g$ after the addition of 1 ml of tonicity restoration buffer (10 mM Tris pH 7.6, 0.5 mM $MgCl_2$, 600 mM NaCl). The homogenate was centrifuged at $60,000 \times g$ for 30 min and pellets were resuspended in Tris buffer (50 mM Tris pH 7.4, containing protease inhibitors). Binding reactions contained 20 µg membranes as determined by BCA protein assay (Pierce), 50 nM [$^3$H]-nicotinic acid (Amersham) with or without compound addition in 250 µl of binding buffer (50 mM Tris pH 7.4, 2 mM $MgCl_2$, 0.02% CHAPS). Incubations were carried out at room temperature for 2 hrs and terminated by filtration using a Filtermate Harvester (PerkinElmer) onto GF/C filter plates (Millipore). Bound [$^3$H]-nicotinic acid was determined by scintillation counting using Top Count NXT (PerkinElmer). Compounds were dissolved in a concentration of $10^{-2}$ or $10^{-3}$ M in DMSO, further dilutions were performed in binding buffer. The effects of compounds were expressed as % inhibition of [$^3$H]-nicotinic acid binding. Sigmoidal curves were fitted using the XLfit3 program (curve fitting and statistical analysis software from ID Business Solutions Ltd. UK) and $IC_{50}$ values determined. The compounds of the present invention exhibit $IC_{50}$ values in a range of about 0.001 µM to about 100 µM in the binding assay. Preferably, the compounds of the present invention have $IC_{50}$ values in a range of about 0.001 µM to about 10.0 µM, more preferably about 0.001 µM to about 1 µM.

Secondary Fluorescent Calcium Indicator Assay (FLIPR)

HEK-293 cells were grown in tissue culture medium (DMEM/Nut mix F12 Medium with Glutamax I (Invitrogen), containing 10% FBS) at 37° C. in a 5% $CO_2$ atmosphere. These cells were cultured in 6-well dishes at $3 \times 10^5$ cells/well and double transfected with DNA vectors (pcDNA3.1, Invitrogen) expressing either HM74A or HM74 and the chimeric G protein Gqi9. Two days after transfection the wells were combined and plated in 150 $cm^2$ flasks, in the presence of 50 µg/ml Hygromycin (Invitrogen) and 500 µg/ml Geneticin (Gibco). Fourteen days after plating, colonies were picked, expanded and analyzed for expression using a functional assay (FLIPR). Stable transfected HEK-293 cells expressing either HM74A or HM74 and the chimeric G protein Gqi9 were plated at 50,000 cells/well in black 96-well plates with clear bottom (Costar) and cultured to confluency overnight in growth media (DMEM/Nut mix F12 Medium with Glutamax I (Invitrogen), containing 10% FBS) at 37° C. in a humidified cell incubator containing 5% $CO_2$. Growth media was aspirated and replaced with 100 µl of 1× FLIPR Calcium Assay Dye (Molecular Devices) in Hank's balanced salt solution (HBSS) containing 10 mM HEPES, and 250 mM probenecid (Sigma), for 1 hour at 37° C. Cell plates were transferred to a FLIPR unit (Molecular Devices), and 50 µl of 3× compound dilution were added. Fluorescence emissions were measured and the effects of compounds were expressed as % stimulation of maximal nicotinic acid response (100 µM). Sigmoidal curves were fitted using the XLfit3 program (ID Business Solutions Ltd. UK) and $EC_{50}$ values determined.

The compounds of the present invention exhibit $EC_{50}$ values in a range of about 0.001 µM to about 100 µM in the FLIPR assay. Preferably, the compounds of the present invention have $EC_{50}$ values in a range of about 0.001 µM to about 10.0 µM; more preferably about 0.001 µM to about 1 µM.

In the following table, $EC_{50}$ values for some of the compounds of the present invention are shown.

| Example | $EC_{50}$ HM74A [µM] |
|---------|----------------------|
| 2       | 5.7053               |
| 28      | 2.714                |
| 58      | 0.4255               |

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 5000 mg, preferably about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-1000 mg, preferably 1-300 mg, more preferably 1-100 mg, of a compound of formula I.

The following Examples serve to illustrate the present invention in more detail. They are, however, not intended to limit its scope in any manner.

EXAMPLES

Abbreviations:
AcOH=acetic acid, $Boc_2O$=ditert-butyldicarbonate, BOP—Cl=bis(2-oxo-3-oxazolidinyl)phosphonic chloride, nBuLi=n-butyl lithium, $CH_2Cl_2$=dichloromethane, $CH_3CN$=acetonitrile, DIPEA=N,N-diisopropylethylamine, DMF=N,N-dimethylformamide, DMSO=dimethylsulfoxide, DMAP=N,N-dimethylaminopyridine, EtOH=ethanol, EDCI=N-(3-dimethylaminopropyl)-N'-ethylcarbodiimide hydrochloride, EtOAc=ethyl acetate, $Et_2O$=diethyl ether, h=hour, HCl=hydrochloric acid, HOBt=1-hydroxybenzo-triazole, KOH=potassium hydroxide, KOtBu=potassium tert-butylate, LiHMDS=lithium hexamethyldisilazide, MeOH=methanol, min=minutes, NaH=sodium hydride, $Na_2SO_4$=sodium sulfate, $NH_4Cl$=ammonium chloride, NMM=N-methylmorpholine, iPrOH=isopropanol, quant.=quantitative, r.t.=room temperature, KOH=potassium hydroxide, TBME=tert-butylmethyl ether, TBTU=O-(benzotriazol-1-yl)-N,N,N',N'-tetramethyluronium tetrafluoroborate, THF=tetrahydrofuran, TFA=trifluoroacetic acid.

General Remarks

The reactions were performed under argon, when appropriate.

Example 1

2-Benzyloxymethyl-3H-pyrido[2,3-d]pyrimidin-4-one 1.1

2-Amino-nicotinamide [13438-65-8] was prepared from 2-amino-3-cyanopyridine [24517-64-4] according to a procedure described by E. C. Taylor and A. J. Crovetti, J. Org. Chem. 1954, 19(10) pp 1633-1640, MS(m/e): 137.1 [M⁺].

1.2

To a slurry of 2-amino-nicotinamide (100 mg, 0.7 mmol) in THF (5 ml) was added dropwise benzyloxyacetyl chloride [19810-31-2] (127 µL, 0.8 mmol) in THF (2 ml) at 5° C. The reaction mixture was heated to reflux for 2 hours. Water was added, the phases were separated and the inorganic layer was extracted with EtOAc (3 times). The combined organic layers were washed with brine, dried over $Na_2SO_4$, filtrated and concentrated in vacuo. Column chromatography on silica gel with $CH_2Cl_2$:MeOH 9:1 as eluent yielded 2-(2-benzyloxy-acetylamino)-nicotinamide (76 mg, 36%), MS(m/e): 286.1 [M+H⁺].

1.3

2-(2-Benzyloxy-acetylamino)-nicotinamide (76 mg, 0.3 mmol) in $H_2O$/EtOH (4 ml, 1:1) was stirred with sodium carbonate (28 mg, 0.3 mmol) at reflux for 2 hours. Water was added, the phases were separated and the inorganic layer was extracted with EtOAc (3 times). The combined organic layers were washed with brine, dried over Na$_2$SO$_4$, filtrated and concentrated in vacuo to yield 2-benzyloxymethyl-3H-pyrido[2,3-d]pyrimidin-4-one (15 mg, 21%) as a white solid, MS (m/e): 268.1 [M$^+$].

Example 2

2-Phenoxymethyl-3H-pyrido[2,3-d]pyrimidin-4-one

In analogy to examples 1.2-1.3, from 2-amino-nicotinamide [13438-65-8] and phenoxyacetyl chloride [701-99-5] was prepared 2-phenoxymethyl-3H-pyrido[2,3-d]pyrimidin-4-one as a white solid, MS (m/e): 254.1 [M+H$^+$].

Example 3

2-(4-Chloro-phenoxymethyl)-3H-pyrido[2,3-d]pyrimidin-4-one

In analogy to examples 1.2-1.3, from 2-amino-nicotinamide [13438-65-8] and 4-chlorophenoxyacetyl chloride [4122-68-3] was prepared 2-(4-chloro-phenoxymethyl)-3H-pyrido[2,3-d]pyrimidin-4-one as a light yellow solid, MS (m/e): 288.1 [M+H$^+$, 1Cl].

Example 4

2-(5-Phenyl-pentyl)-3H-pyrido[2,3-d]pyrimidin-4-one 4.1

A solution of 6-phenylhexanoic acid [5581-75-9] (1.45 g, 7.6 mmol) in CH$_2$Cl$_2$ (15 ml) was treated with oxalyl chloride (0.72 ml, 8.6 mmol) in the presence of a catalytic amount of DMF. The solution was stirred for 2 h at ambient temperature. The solvent was evaporated to give crude 6-phenylhexanoic acid chloride, which was used without further purification in the next step.

4.2

To 2-amino-3-cyanopyridine [24517-64-4] (200 mg, 1.7 mmol) in CH$_2$Cl$_2$ (3 ml) and pyridine (3 ml) was added a solution of 6-phenylhexanoic acid chloride (1.5 eq) in CH$_2$Cl$_2$ (1 ml) and the reaction mixture was stirred overnight at ambient temperature. Water was added, the phases were separated and the pH of the inorganic layer was adjusted (pH 7). The inorganic phase was extracted with EtOAc (3 times), the combined organic layers were washed with brine, dried over Na$_2$SO$_4$, filtrated and concentrated in vacuo. Trituration from diethyl ether yielded 6-phenyl-hexanoic acid (3-cyano-pyridin-2-yl)-amide 360 mg (73%) as a white solid, MS (m/e): 294.3 [M+H$^+$].

4.3

To 6-phenyl-hexanoic acid (3-cyano-pyridin-2-yl)-amide (360 mg, 1.2 mmol) in sodium hydroxide (6 ml, 5M) was added ethanol (0.1 ml) and hydrogen peroxide (3% in H$_2$O, 1.5 ml). The reaction mixture was heated to reflux for 3 hours. Water was added, the solution was acidified (pH 5) and extracted with EtOAc (3 times). The combined organic phases were washed with brine, dried over Na$_2$SO$_4$, filtrated and concentrated in vacuo. Column chromatography on silica gel with CH$_2$Cl$_2$:MeOH 9:1 as eluent, followed by trituration from diethyl ether yielded 2-(5-phenyl-pentyl)-3H-pyrido[2,3-d]pyrimidin-4-one as a white solid, MS (m/e): 294.3 [M+H$^+$].

Example 5

2-(4-Methoxy-phenoxymethyl)-3H-pyrido[2,3-d]pyrimidin-4-one

In analogy to examples 4.2-4.3, from 4-methoxy-phenoxyacetic acid chloride [42082-29-1] and 2-amino-3-cyanopyridine [24517-64-4] was prepared 2-(4-methoxy-phenoxymethyl)-3H-pyrido[2,3-d]pyrimidin-4-one as a white solid, MS (m/e): 284.0 [M+H$^+$].

Example 6

2-(4-Ethyl-phenoxymethyl)-3H-pyrido[2,3-d]pyrimidin-4-one

In analogy to examples 4.2-4.3, from (4-ethylphenoxy)acetyl chloride [167762-94-9] and 2-amino-3-cyanopyridine [24517-64-4] was prepared 2-(4-ethyl-phenoxymethyl)-3H-pyrido[2,3-d]pyrimidin-4-one as a white solid, MS (m/e): 282.3 [M+H$^+$].

Example 7

2-(4-Phenyl-butyl)-3H-pyrido[2,3-d]pyrimidin-4-one

In analogy to examples 4.2-4.3, from 5-phenylvaleryl chloride [20371-41-9] and 2-amino-3-cyanopyridine [24517-64-4] was prepared 2-(4-phenyl-butyl)-3H-pyrido[2,3-d]pyrimidin-4-one as a white solid, MS (m/e): 280.3 [M+H$^+$].

Example 8

2-(4-Fluoro-phenoxymethyl)-3H-pyrido[2,3-d]pyrimidin-4-one

In analogy to examples 4.2-4.3, from (4-fluorophenoxy)-acetyl chloride [405-78-7] and 2-amino-3-cyanopyridine [24517-64-4] was prepared 2-(4-fluoro-phenoxymethyl)-3H-pyrido[2,3-d]pyrimidin-4-one as a white solid, MS (m/e): 272.0 [M+H$^+$].

Example 9

2-(3-Chloro-phenoxymethyl)-3H-pyrido[2,3-d]pyrimidin-4-one 9.1

In analogy to example 4.2, from 3-chlorophenoxyacetyl chloride [114476-84-5] and 2-amino-3-cyanopyridine [24517-64-4] was prepared 2-(3-chloro-phenoxy)-N-(3-cyano-pyridin-2-yl)-acetamide as light brown solid, MS (m/e): 288.0 [M+H$^+$, 1Cl].

9.2

In analogy to example 4.3, from 2-(3-chloro-phenoxy)-N-(3-cyano-pyridin-2-yl)-acetamide was prepared 2-(3-chloro-phenoxymethyl)-3H-pyrido[2,3-d]pyrimidin-4-one as a white solid, MS (m/e): 287.9 [M+H$^+$, 1Cl].

Example 10

2-Phenethyl-3H-pyrido[2,3-d]pyrimidin-4-one

In analogy to examples 4.2-4.3, from benzenepropanoyl chloride [645-45-4] and 2-amino-3-cyanopyridine [24517-

64-4] was prepared 2-phenethyl-3H-pyrido[2,3-d]pyrimidin-4-one as a light yellow solid, MS (m/e): 252.1 [M+H$^+$].

Example 11

2-[2-(3-Chloro-phenyl)-ethyl]-3H-pyrido[2,3-d]pyrimidin-4-one

In analogy to examples 4.2-4.3, from 3-(3-chlorophenyl)propanoyl chloride [40478-50-0] and 2-amino-3-cyanopyridine [24517-64-4] was prepared 2-[2-(3-chloro-phenyl)-ethyl]-3H-pyrido[2,3-d]pyrimidin-4-one as a white solid, MS (m/e): 286.0 [M+H$^+$, 1Cl].

Example 12

2-[2-(3-Methoxy-phenyl)-ethyl]-3H-pyrido[2,3-d]pyrimidin-4-one

In analogy to examples 4.2-4.3, from 3-(3-methoxyphenyl)propionyl chloride [40478-49-7] and 2-amino-3-cyanopyridine [24517-64-4] was prepared 2-[2-(3-methoxy-phenyl)-ethyl]-3H-pyrido[2,3-d]pyrimidin-4-one as a white solid, MS (m/e): 282.0 [M+H$^+$].

Example 13

2-[4-(4-Chloro-phenyl)-butyl]-3H-pyrido[2,3-d]pyrimidin-4-one

In analogy to examples 4.2-4.3, from 5-(4-chloro-phenyl)-pentanoyl chloride [61875-54-5] and 2-amino-3-cyanopyridine [24517-64-4] was prepared 2-[4-(4-chloro-phenyl)-butyl]-3H-pyrido[2,3-d]pyrimidin-4-one as a white solid, MS (m/e): 314.0 [M+H$^+$, 1Cl].

Example 14

2-(6-Phenyl-hexyl)-3H-pyrido[2,3-d]pyrimidin-4-one

In analogy to example examples 4.2-4.3, from 7-phenyl-heptanoyl chloride [61875-55-6] and 2-amino-3-cyanopyridine [24517-64-4] was prepared 2-(6-phenyl-hexyl)-3H-pyrido[2,3-d]pyrimidin-4-one as a colorless oil, MS (m/e): 307.2 [M$^+$].

Example 15

2-[4-(4-Fluoro-phenyl)-butyl]-3H-pyrido[2,3-d]pyrimidin-4-one

In analogy to examples 4.2-4.3, from 5-(4-fluorophenyl)pentanoyl chloride [204589-92-4] and 2-amino-3-cyanopyridine [24517-64-4] was prepared 2-[4-(4-fluoro-phenyl)-butyl]-3H-pyrido[2,3-d]pyrimidin-4-one as a white solid, MS (m/e): 298 [M+H$^+$].

Example 16

2-(2-Methoxy-phenoxymethyl)-3H-pyrido[2,3-d]pyrimidin-4-one

In analogy to examples 4.2-4.3, from (2-methoxyphenoxy)acetyl chloride [40926-73-6] and 2-amino-3-cyanopyridine [24517-64-4] was prepared 2-(2-methoxy-phenoxymethyl)-3H-pyrido[2,3-d]pyrimidin-4-one as a white solid, MS: 283.9 [M+H$^+$].

Example 17

2-p-Tolyloxymethyl-3H-pyrido[2,3-d]pyrimidin-4-one

In analogy to examples 4.2-4.3, from (4-methylphenoxy)acetyl chloride [15516-47-9] and 2-amino-3-cyanopyridine [24517-64-4] was prepared 2-p-tolyloxymethyl-3H-pyrido[2,3-d]pyrimidin-4-one as a white solid, MS: 268.2 [M+H$^+$].

Example 18

2-(2-Chloro-phenoxymethyl)-3H-pyrido[2,3-d]pyrimidin-4-one

In analogy to examples 4.2-4.3, from (2-chlorophenoxy)acetyl chloride [20143-41-3] and 2-amino-3-cyanopyridine [24517-64-4] was prepared 2-(2-chloro-phenoxymethyl)-3H-pyrido[2,3-d]pyrimidin-4-one as a white solid, MS: 287.9 [M+H$^+$, 1Cl].

Example 19

2-(2,3-Dimethyl-phenoxymethyl)-3H-pyrido[2,3-d]pyrimidin-4-one

In analogy to examples 4.2-4.3, from (2,3-dimethylphenoxy)acetyl chloride [40926-74-7] and 2-amino-3-cyanopyridine [24517-64-4] was prepared 2-(2,3-dimethyl-phenoxymethyl)-3H-pyrido[2,3-d]pyrimidin-4-one as a white solid, MS (m/e): 282 [M+H$^+$].

Example 20

2-(Naphthalen-1-yloxymethyl)-3H-pyrido[2,3-d]pyrimidin-4-one

In analogy to examples 4.2-4.3, from (naphthalen-1-yloxy)-acetyl chloride [2007-12-7] and 2-amino-3-cyanopyridine [24517-64-4] was prepared 2-(naphthalen-1-yloxymethyl)-3H-pyrido[2,3-d]pyrimidin-4-one as a off-white solid, MS (m/e): 304 [M+H$^+$].

Example 21

2-(4-Chloro-2-methyl-phenoxymethyl)-3H-pyrido[2,3-d]pyrimidin-4-one

In analogy to examples 4.2-4.3, from (2-methyl-4-chlorophenoxy)acetyl chloride [6597-79-1] and 2-amino-3-cyanopyridine [24517-64-4] was prepared 2-(4-chloro-2-methyl-phenoxymethyl)-3H-pyrido[2,3-d]pyrimidin-4-one as a white solid, MS (m/e): 301.9 [M+H$^+$, 1Cl].

Example 22

6-Methyl-2-(4-phenyl-butyl)-3H-pyrido[2,3-d]pyrimidin-4-one

In analogy to examples 4.2-4.3, from 5-phenylvaleryl chloride [20371-41-9] and 2-amino-5-methylnicotinonitrile [38076-78-7] was prepared 6-methyl-2-(4-phenyl-butyl)-3H-pyrido[2,3-d]pyrimidin-4-one as a white solid, MS (m/e): 294.1 [M+H$^+$].

Example 23

(4-Oxo-3,4-dihydro-pyrido[2,3-d]pyrimidin-2-ylmethyl)-carbamic acid benzyl ester In analogy to examples 4.2-4.3, from benzyloxycarbonylaminoacetyl chloride [15050-24-5] and 2-amino-3-cyanopyridine [24517-64-4] was prepared (4-oxo-3,4-dihydro-pyrido[2,3-d]pyrimidin-2-ylmethyl)-carbamic acid benzyl ester as a off-white solid, MS (m/e): 311 [M+H$^+$].

Example 24

N-(4-Oxo-3,4-dihydro-pyrido[2,3-d]pyrimidin-2-ylmethyl)-3-phenyl-propionamide 24.1
(4-Oxo-3,4-dihydro-pyrido[2,3-d]pyrimidin-2-ylmethyl)-carbamic acid benzyl ester (383 mg, 1.23 mmol) in HBr (33% in acetic acid, 4 ml) was stirred for 2 h at ambient temperature. TBME (15 ml) was added and the precipitated solid was filtrated and washed with TBME to yield a salt of 2-aminomethyl-3H-pyrido[2,3-d]pyrimidin-4-one (0.1 CH$_3$CO$_2$H, 2.03 HBr) as white solid, MS: 176 [M$^+$], which was subjected to the next reaction without further purification.

24.2
To 3-phenylpropionic acid [501-52-0] (66.6 mg, 0.444 mmol) in DMF (4 ml) was added EDCI [25952-53-8] (102 mg, 0.532 mmol), HOBt [2592-95-2] (8 mg, 0.059 mmol) and NMM [109-02-4] (0.15 ml, 1.18 mmol) at 0° C. The reaction mixture was stirred at ambient temperature for 2 h, and then was added to a solution of the salt of 2-aminomethyl-3H-pyrido[2,3-d]pyrimidin-4-one (CH$_3$CO$_2$H, HBr) (100 mg) in DMF (2 ml). Stirring was continued for 18 h, the solvents were evaporated and the residue was redissolved in EtOAc/THF and a saturated solution of ammonium chloride. The inorganic layer was extracted with EtOAc. The combined organic phases were washed with brine, dried over Na$_2$SO$_4$, filtrated and evaporated. Column chromatography with CH$_2$Cl$_2$/MeOH 9:1, followed by trituration with TBME gave N-(4-oxo-3,4-dihydro-pyrido[2,3-d]pyrimidin-2-ylmethyl)-3-phenyl-propionamide (43.1 mg, 47%) as a off-white solid, MS (m/e): 309 [M+H$^+$].

Example 25

N-(4-Oxo-3,4-dihydro-pyrido[2,3-d]pyrimidin-2-ylmethyl)-4-phenyl-butyramide

In analogy to example 24.2, from 4-phenylbutyric acid [1821-12-1] and 2-aminomethyl-3H-pyrido[2,3-d]pyrimidin-4-one was prepared N-(4-oxo-3,4-dihydro-pyrido[2,3-d]pyrimidin-2-ylmethyl)-4-phenyl-butyramide as a pink solid, MS (m/e): 323.3 [M+H$^+$].

Example 26

6-Bromo-2-(4-phenyl-butyl)-3H-pyrido[2,3-d]pyrimidin-4-one

In analogy to examples 4.2-4.3, from 5-phenylvaleryl chloride [20371-41-9] and 2-amino-5-bromonicotinonitrile [709652-82-4] was prepared 6-bromo-2-(4-phenyl-butyl)-3H-pyrido[2,3-d]pyrimidin-4-one as a white solid, MS (m/e): 357.9 [M+H$^+$, 1Br].

Example 27

6-Bromo-2-[4-(4-fluoro-phenyl)-butyl]-3H-pyrido[2,3-d]pyrimidin-4-one

In analogy to examples 4.2-4.3, from 5-(4-fluorophenyl)pentanoyl chloride [204589-92-4] and 2-amino-5-bromonicotinonitrile [709652-82-4] was prepared 6-bromo-2-[4-(4-fluoro-phenyl)-butyl]-3H-pyrido[2,3-d]pyrimidin-4-one as a white solid, MS (m/e): 376.1 [M+H$^+$, 1Br].

Example 28

2-[3-(4-Methoxy-phenyl)-propoxy]-3H-pyrido[2,3-d]pyrimidin-4-one

In a screw-capped glass tube, 3-(4-methoxyphenyl)-1-propanol ([5406-18-8], 137 mg, 0.826 mmol) was added to a mixture of 2-chloropyrido[2,3-d]pyrimidin-4(1H)-one ([93049-38-8], 50 mg, 0.28 mmol) and KOtBu (62 mg, 0.55 mmol) in DMSO (2 ml). The mixture was heated (3 days, 120° C.) and the title compound was isolated from the product mixture by reversed-phase, preparative HPLC (Agilent Zorbax XdB C18 column, solvent gradient 5-95% CH$_3$CN in 0.1% TFA(aq) over 7 min, flow rate 30 ml/min). MS: m/e=310.5 [M−H$^-$], $^1$H NMR (d$^6$-DMSO): δ 2.02 (dd, 2H), 3.36 (d, 2H), 3.71 (s, 3H), 4.42 (d, 2H), 6.86 (d, 2H), 7.15 (d, 2H), 7.36 (dd, 1H), 8.38 (d, 1H), 8.79 (d, 1H).

Example 29

2-(3-Phenyl-propoxy)-3H-pyrido[2,3-d]pyrimidin-4-one

The title compound (MS: m/e=280.4 [M−H$^-$]) was obtained in analogy to example 28 from 3-phenyl-1-propanol [122-97-4].

Example 30

2-(4-Phenyl-butoxy)-3H-pyrido[2,3-d]pyrimidin-4-one

The title compound (MS: m/e=294 [M−H$^-$]) was obtained in analogy to example 28 from 4-phenyl-1-butanol [3360-41-6].

Example 31

2-[4-(4-Methoxy-phenyl)-butoxy]-3H-pyrido[2,3-d]pyrimidin-4-one

The title compound (MS: m/e=324.5 [M−H$^-$]) was obtained in analogy to example 28 from 4-(4-methoxyphenyl)-1-butanol [52244-70-9].

Example 32

2-(3-Pyridin-3-yl-propoxy)-3H-pyrido[2,3-d]pyrimidin-4-one

The title compound (MS: m/e=281.4 [M−H$^-$]) was obtained in analogy to example 28 from 3-(3-pyridyl)-1-propanol [2859-67-8].

Example 33

2-(2-Phenoxy-ethoxy)-3H-pyrido[2,3-d]pyrimidin-4-one

The title compound (MS: m/e=282.1 [M−H⁻]) was obtained in analogy to example 28 from 2-phenoxyethanol [122-99-6].

Example 34

2-[2-(Naphthalen-2-yloxy)-ethoxy]-3H-pyrido[2,3-d]pyrimidin-4-one

The title compound (MS: m/e=332.3 [M−H⁻]) was obtained in analogy to example 28 from 2-(2-naphtoxy)ethanol [93-20-9].

Example 35

2-(3-Phenoxy-propoxy)-3H-pyrido[2,3-d]pyrimidin-4-one

The title compound (MS: m/e=296.5 [M−H⁻]) was obtained in analogy to example 28 from 3-phenoxy-1-propanol [6180-61-6].

Example 36

2-Phenethyloxymethyl-3H-pyrido[2,3-d]pyrimidin-4-one 36.1

NaH (6.87 g, 172 mmol) was added slowly to a solution of 2-phenylethanol ([60-12-8], 6.00 g, 5.88 ml, 49.1 mmol) in DMF (50 ml). The reaction mixture was heated and kept for 10 min at 60° C. Chloroacetic acid ([79-11-8], 8.12 g, 86 mmol) was added slowly and carefully (exothermic), and the mixture was kept for 1 h at 60° C. The mixture was poured on ice and extracted twice with diethyl ether. Then the water phase was acidified (HCl, pH~3) and extracted twice with ethyl acetate. Phenethyloxy-acetic acid [81228-03-7] was obtained after drying (Na₂SO₄), and evaporation of the solvent. The compound was sufficiently pure for the next step without further purification.

36.2

Phenethyloxy-acetic acid (3.89 g, 18.9 mmol) was dissolved in a mixture of 50 ml dichloromethane and 2.6 ml DMF. Oxalyl chloride ([79-37-8], 1.76 ml, 20.8 mmol) was slowly added, and the mixture was stirred at r.t. overnight. Phenethyloxy-acetyl chloride [221019-38-1] was obtained after evaporation of the solvent, and was sufficiently pure for the next step.

36.3

Phenethyloxy-acetyl chloride (3.79 g, 6.12 mmol) was added to a solution of 2-amino-3-cyanopyridine ([24517-64-4], 662 mg, 5.56 mmol) and DMAP (67 mg, 0.55 mmol) in a mixture of dichloromethane (8 ml) and pyridine (8 ml). After 3 h at r.t., the solvent was evaporated, and N-(3-cyano-pyridin-2-yl)-2-phenethyloxy-acetamide was isolated from the residue by column chromatography (silica gel, heptane, ethyl acetate, methanol). MS: m/e=282.1 [M+H⁺], ¹H NMR (d⁶-DMSO): 2.91 (t, 2H), 3.77 (t, 2H), 4.18 (s, 2H), 7.17-7.23 (m, 5H), 7.47 (dd, 1H), 8.37 (d, 1H), 8.71 (d, 1H), 10.55 (bs, 1H).

36.4

Potassium carbonate (1.22 g, 8.82 mmol), DMSO (0.44 ml), and hydrogen peroxide (0.9 ml of a 30% solution in H₂O) were added to a suspension of N-(3-cyano-pyridin-2-yl)-2-phenethyloxy-acetamide (400 mg, 1.42 mmol) in methanol (6 ml). After 3 h at r.t., the mixture was taken up in ethyl acetate, and washed with salt. NH₄Cl. The solution was dried (Na₂SO₄) and the solvent was evaporated. The residue was triturated with tert-butyl methyl ether to give the title compound. MS: m/e=280.4 [M−H⁻], ¹H NMR (d⁶-DMSO): 2.91 (t, 2H), 3.78 (t, 2H), 4.45 (s, 2H), 7.17-7.22 (m, 5H), 7.53 (dd, 1H), 8.49 (d, 1H), 8.93 (d, 1H), 12.44 (bs, 1H).

Example 37

2-[2-(2-Fluoro-phenyl)-ethoxymethyl]-3H-pyrido[2,3-d]pyrimidin-4-one

The title compound (MS: m/e=298.4 [M−H⁻]) was obtained in analogy to example 36 from 2-(2-fluoro-phenyl)-ethanol [50919-06-7].

Example 38

2-[3-(3,4-Difluoro-phenoxy)-propoxy]-3H-pyrido[2,3-d]pyrimidin-4-one

The title compound (MS: m/e=332.3 [M−H⁻]) was obtained in analogy to example 28 from 3,4-difluoro-phenoxy)-propanol.

Example 39

2-[3-(4-Methoxy-phenoxy)-propoxy]-3H-pyrido[2,3-d]pyrimidin-4-one

The title compound (MS: m/e=326.3 [M−H⁻]) was obtained in analogy to example 28 from 3-(4-methoxy-phenoxy)-propanol [118943-21-8].

Example 40

2-[2-(4-Fluoro-phenyl)-ethoxymethyl]-3H-pyrido[2,3-d]pyrimidin-4-one 40.1

N-(3-Cyano-pyridin-2-yl)-2-[2-(4-fluoro-phenyl)-ethoxy]-acetamide (MS: m/e=300.3 [M+H⁺]) was obtained from [2-(4-fluoro-phenyl)-ethoxy]-acetic acid [81228-04-8] in analogy to examples 36.2-36.3.

40.2

Hydrogen peroxide (3% in H₂O, 2.8 ml) and ethanol (0.6 ml) were added to a suspension of N-(3-cyano-pyridin-2-yl)-2-[2-(4-fluoro-phenyl)-ethoxy]-acetamide (900 mg, 3 mmol) in 5N NaOH (11 ml), and the mixture was heated to reflux (4 h). Upon cooling, the solution was diluted with water and acidified (HCl, pH ~3). The precipitated title compound was filtered off, triturated with tert-butyl methyl ether, and dried. MS: m/e=300.3 [M+H⁺], ¹H NMR (d⁶-DMSO): 2.89 (t, 2H), 3.77 (t, 2H), 4.45 (s, 2H), 7.04-7.12 (m, 2H), 7.28-7.33 (m, 2H), 7.54 (dd, 1H), 8.50 (d, 1H), 8.95 (d, 1H), 12.45 (bs, 1H).

Example 41

2-[4-(4-Fluoro-phenyl)-3-methyl-butyl]-3H-pyrido[2,3-d]pyrimidin-4-one 41.1

Sodium ethanolate (0.836 g, 12 mmol) was added under cooling (0° C.) to a solution of 4-fluorobenzyl triphenylphosphonium chloride ([3462-95-1], 5.00 g, 12 mmol) in ethanol, and the mixture was stirred for 45min at r.t. Ethyl levulinate ([539-88-8], 1.77 g, 12 mmol) was added, and the light-orange mixture was refluxed (36 h). After the usual workup, 5-(4-fluoro-phenyl)-4-methyl-pent-4-enoic acid ethyl ester was obtained by column chromatography (silica gel, ethyl acetate/hexane) from the reaction mixture. MS: m/e=237.1 [M+H$^+$].

41.2

A slurry of palladium on charcoal (10%, 1.00 g) and 5-(4-fluoro-phenyl)-4-methyl-pent-4-enoic acid ethyl ester (1.01 g) in ethanol (20 ml) was stirred for 2 h under an atmosphere of hydrogen. The reaction mixture was filtered (dicalite), and the solvent was evaporated. Upon evaporation of the solvent, 5-(4-fluoro-phenyl)-4-methyl-pentanoic acid ethyl ester was obtained; the compound was used in the next step without further purification. MS: m/e=239.3 [M+H$^+$].

41.3

5-(4-Fluoro-phenyl)-4-methyl-pentanoic acid ethyl ester (1.18 g, 5 mmol) was added to a solution of KOH (1.39 g, 25 mmol) in ethanol (20 ml). After 2 h at r.t., the solvent was evaporated and the residue was taken up in water, which was made alkaline (KOH) and was extracted twice with diethyl ether. Upon acidification of the water phase (HCl), the product was extracted with ethyl acetate. The organic phase was washed (brine), dried (Na$_2$SO$_4$), and the solvent was evaporated. The obtained 5-(4-fluoro-phenyl)-4-methyl-pentanoic acid was used in the next step without any further purification. $^1$H NMR (d$^6$-DMSO): 0.85 (d, 3H), 1.48 (m, 1H), 1.71 (m, 2H), 2.34-2.65 (m, 4H), 6.92 (m, 2H), 7.06 (m, 2H).

41.4

5-(4-Fluoro-phenyl)-4-methyl-pentanoic acid (3-cyano-pyridin-2-yl)-amide was obtained from 5-(4-fluoro-phenyl)-4-methyl-pentanoic acid in analogy to examples 36.2-36.3. MS: m/e=312.3 [M+H$^+$].

41.5

The title compound was obtained from 5-(4-fluoro-phenyl)-4-methyl-pentanoic acid (3-cyano-pyridin-2-yl)-amide in analogy to example 40.2. MS: m/e=312.1 [M+H$^+$]. $^1$H NMR (d$^6$-DMSO): 0.87 (d, 3H), 1.60 (m, 1H), 1.77 (m, 2H), 2.60-2.80 (m, 4H), 7.07 (m, 2H), 7.21 (m, 2H), 7.49 (dd, 1H), 8.45 (d, 1H), 8.91 (d, 1H).

Example 42

2-[5-(4-Chloro-phenyl)-pentyl]-3H-pyrido[2,3-d]pyrimidin-4-one 42.1

6-(4-Chloro-phenyl)-hexanoic acid (3-cyano-pyridin-2-yl)-amide was obtained from 6-(4-chloro-phenyl)-hexanoic acid [161725-12-8] in analogy to examples 36.2-36.3. MS: m/e=328.3 [M+H$^+$].

42.2

The title compound was obtained from 6-(4-chloro-phenyl)-hexanoic acid (3-cyano-pyridin-2-yl)-amide in analogy to example 40.2. MS: m/e=328.1 [M+H$^+$].

Example 43

2-[3-(4-Fluoro-phenoxy)-propyl]-3H-pyrido[2,3-d]pyrimidin-4-one 43.1

Under cooling (0° C.), sodium ethanolate (2.18 g, 32 mmol) was added to a mixture of 4-fluorophenol ([371-41-5], 3.00 g, 27 mmol), ethyl 4-chlorobutyrate ([3153-36-4], 4.84 g, 32 mmol) and ethanol (15 ml), and the reaction mixture was then refluxed overnight. The solvent was evaporated, the residue was taken up in ethyl ester and was washed with water. After drying (Na$_2$SO$_4$), the solvent was evaporated, and 4-(4-fluoro-phenoxy)-butyric acid ethyl ester was isolated from the residue by column chromatography (silica gel, ethyl acetate/heptane). $^1$H NMR (d$^6$-DMSO): 1.29 (t, 3H), 2.11 (tt, 2H), 2.51 (t, 2H), 3.96 (t, 2H), 4.13 (q, 2H), 6.79-6.85 (m, 2H), 6.92-6.99 (m, 2H).

43.2

4-(4-Fluoro-phenoxy)-butyric acid was obtained from 4-(4-fluoro-phenoxy)-butyric acid ethyl ester in analogy to example 41.3. $^1$H NMR (d$^6$-DMSO): 2.10 (tt, 2H), 2.59 (t, 2H), 3.97 (t, 2H), 6.79-6.84 (m, 2H), 6.92-6.99 (m, 2H).

43.3

N-(3-Cyano-pyridin-2-yl)-4-(4-fluoro-phenoxy)-butyramide was obtained from 4-(4-fluoro-phenoxy)-butyric acid in analogy to examples 36.2-36.3. MS: m/e=300.3 [M+H$^+$].

43.4

The title compound was obtained from N-(3-cyano-pyridin-2-yl)-4-(4-fluoro-phenoxy)-butyramide in analogy to example 40.2. MS: m/e=300.3 [M+H$^+$]), $^1$H NMR (d$^6$-DMSO): 2.16 (tt, 2H), 2.75 (t, 2H), 4.02 (t, 2H), 6.91-6.99 (m, 2H), 7.30-7.34 (m, 2H), 7.31 (dd, 1H), 8.37 (d, 1H), 8.77 (d, 1H).

Example 44

2-[2-(4-Chloro-phenyl)-ethoxymethyl]-3H-pyrido[2,3-d]pyrimidin-4-one

The title compound was obtained from 2-(4-chloro-phenyl)-ethanol [1875-88-3] in analogy to example 36. MS: m/e=316.1 [M+H$^+$].

Example 45

2-(2-p-Tolyl-ethoxymethyl)-3H-pyrido[2,3-d]pyrimidin-4-one

The title compound was obtained from 2-p-tolyl-ethanol [699-02-5] in analogy to example 36. MS: m/e=296.4 [M+H$^+$].

Example 46

2-[2-(4-Methoxy-phenyl)-ethoxymethyl]-3H-pyrido[2,3-d]pyrimidin-4-one

The title compound was obtained from 2-(4-methoxy-phenyl)-ethanol [702-23-8] in analogy to example 36. MS: m/e=312.1 [M+H$^+$].

Example 47

2-(2-Benzyloxy-ethyl)-3H-pyrido[2,3-d]pyrimidin-4-one

The title compound was obtained from 3-benzyloxy-propionic acid [27912-85-2] in analogy to examples 36.2-36.4. MS: m/e=282.3 [M+H$^+$].

Example 48

2-(4'-Fluoro-biphenyl-4-yloxymethyl)-3H-pyrido[2,3-d]pyrimidin-4-one 48.1

N-(3-Cyano-pyridin-2-yl)-2-(4'-fluoro-biphenyl-4-yl)-acetamide was obtained from (4'-fluoro-biphenyl-4-yl)-acetic acid [6908-38-9] in analogy to examples 36.2-36.3. MS: m/e=348.4 [M+H$^+$].

48.2

The title compound was obtained from N-(3-cyano-pyridin-2-yl)-2-(4'-fluoro-biphenyl-4-yl)-acetamide in analogy to example 40.2. MS: m/e=348.1 [M+H$^+$].

Example 49

2-(4-m-Tolyl-butyl)-3H-pyrido[2,3-d]pyrimidin-4-one 49.1

Pent-4-ynoic acid (3-cyano-pyridin-2-yl)-amide was obtained from pentynoic acid [6089-09-4] in analogy to examples 36.2-36.3. MS: m/e=200.3 [M+H$^+$].

49.2

Under an atmosphere of argon, bis(triphenylphosphine)palladium(II) chloride ([13965-03-2], 326 mg) and copper(I) iodide (44 mg) were added to a solution of 3-iodotoluene ([625-95-6], 506 mg, 2 mmol) and pent-4-ynoic acid (3-cyano-pyridin-2-yl)-amide (508 mg, 3 mmol) in diethylamine (15 ml). The mixture was kept at r.t. (3d). The volatiles were evaporated, and the residue was taken up in ethyl acetate. After washing (H$_2$O) and drying (Na$_2$SO$_4$), the solvent was evaporated and 5-m-tolyl-pent-4-ynoic acid (3-cyano-pyridin-2-yl)-amide was isolated from the reaction mixture by column chromatography (silica gel, ethyl acetate/heptane). MS: m/e=290.1 [M+H$^+$].

49.3

5-m-Tolyl-pentanoic acid (3-cyano-pyridin-2-yl)-amide was obtained from 5-m-tolyl-pent-4-ynoic acid (3-cyano-pyridin-2-yl)-amide in analogy to example 41.2. MS: m/e=294.4 [M+H$^+$].

49.4

The title compound was obtained from 5-m-tolyl-pentanoic acid (3-cyano-pyridin-2-yl)-amide in analogy to example 40.2. MS: m/e=294.3 [M+H$^+$].

Example 50

2-(1-Methyl-4-phenyl-butyl)-3H-pyrido[2,3-d]pyrimidin-4-one 50.1

Under cooling (0° C.), diethyl methylmalonate ([609-08-5], 1.175 g, 7 mmol) was added to a suspension of NaH (60% in mineral oil, 325 mg, 8 mmol) in diethyl ether (30 ml). After 3 h at r.t, the solvent was evaporated and the residue was dissolved in DMF (20 ml). To this solution, triphenylvinylphosphonium bromide ([5044-52-0], 3.00 g, 8 mmol) and benzaldehyde ([100-52-7], 860 mg, 8 mmol) were added. The reaction mixture was stirred at 100° C. overnight, and was then taken up in ethyl acetate, washed (H$_2$O), and dried (Na$_2$SO$_4$). The solvent was evaporated, and 2-methyl-2-(3-phenyl-allyl)-malonic acid diethyl ester was isolated from the residue by column chromatography (silica gel, ethyl acetate/heptane). MS: m/e=291.0 [M+H$^+$].

50.2

2-Methyl-2-(3-phenyl-propyl)-malonic acid diethyl ester was obtained from 2-methyl-2-(3-phenyl-allyl)-malonic acid diethyl ester in analogy to example 41.2. MS: m/e=293.0 [M+H$^+$].

50.3

2-Methyl-2-(3-phenyl-propyl)-malonic acid diethyl ester was added to a solution of KOH in ethanol. The mixture was stirred for 5 h at r.t., and was then heated to reflux overnight. The solvent was evaporated, the residue was taken up in water, and extracted with diethyl ether. The water phase was acidified (HCl), and extracted with ethyl acetate. The organic phase was washed (brine), dried (Na$_2$SO$_4$), and the solvent was evaporated. The obtained 2-methyl-5-phenyl-pentanoic acid was sufficiently pure for the next step. MS: m/e=191.4 [M−H$^-$].

50.4

2-Methyl-5-phenyl-pentanoic acid (3-cyano-pyridin-2-yl)-amide was obtained from 2-methyl-5-phenyl-pentanoic acid in analogy to examples 36.2-36.3. MS: m/e=294.3 [M+H$^+$].

50.5

The title compound was obtained from 2-methyl-5-phenyl-pentanoic acid (3-cyano-pyridin-2-yl)-amide in analogy to example 40.2. MS: m/e=294.3 [M+H$^+$].

Example 51

2-(Naphthalen-2-yloxymethyl)-3H-pyrido[2,3-d]pyrimidin-4-one

The title compound was obtained from 2-naphtoxyacetic acid [120-23-0] in analogy to example 40. MS: m/e=304.0 [M+H$^+$].

Example 52

1-Benzyl-3-(4-oxo-3,4-dihydro-pyrido[2,3-d]pyrimidin-2-ylmethyl)-urea

Benzyl isocyanate was added to a solution of 2-aminomethyl-3H-pyrido[2,3-d]pyrimidin-4-one (example 24.1) in pyridine; the reaction mixture was kept at r.t. overnight. The volatiles were evaporated and the title compound was isolated from the reaction mixture by reversed-phase, preparative HPLC. MS: m/e=308.4 [M−H$^-$].

Example 53

2-[2-(4-Fluoro-phenyl)-ethoxymethyl]-6-methyl-3H-pyrido[2,3-d]pyrimidin-4-one

The title compound was obtained from 2-amino-5-methyl-nicotinonitrile [38076-78-7] in analogy to example 40. MS: m/e=314.3 [M+H$^+$].

Example 54

2-(4-Iodo-phenoxymethyl)-3H-pyrido[2,3-d]pyrimidin-4-one

The title compound was obtained from (4-iodo-phenoxy)-acetic acid [1878-94-0] in analogy to examples 36.2-36.4. MS: m/e=380.3 [M+H$^+$].

Example 55

2-[3-(4-Fluoro-phenoxy)-propoxy]-3H-pyrido[2,3-d]pyrimidin-4-one

The title compound was obtained from 3-(4-fluoro-phenoxy)-propan-1-ol [104413-57-2] in analogy to example 28. MS: m/e=314.1 [M−H$^-$].

Example 56

2-(3-p-Tolyloxy-propoxy)-3H-pyrido[2,3-d]pyrimidin-4-one

The title compound was obtained from 3-p-tolyloxy-propan-1-ol [52449-00-0] in analogy to example 28. MS: m/e=310.5 [M−H$^-$].

Example 57

2-[3-(2-Fluoro-phenoxy)-propoxy]-3H-pyrido[2,3-d]pyrimidin-4-one

The title compound was obtained from 3-(2-fluoro-phenoxy)-propan-1-ol [145073-40-1] in analogy to example 28. MS: m/e=314.3 [M−H$^-$].

Example 58

2-(3-o-Tolyloxy-propoxy)-3H-pyrido[2,3-d]pyrimidin-4-one

The title compound was obtained from 3-o-tolyloxy-propan-1-ol [52448-99-4] in analogy to example 28. MS: m/e=310.4 [M−H$^-$].

Example 59

2-[2-(2-Fluoro-phenyl)-ethoxymethyl]-7-methyl-3H-pyrido[2,3-d]pyrimidin-4-one

The title compound was obtained from 2-amino-6-methyl-nicotinonitrile [84647-20-1] and 2-(2-fluoro-phenyl)-ethanol [50919-06-7] in analogy to example 36. MS: m/e=312.1 [M−H$^-$].

Example 60

(4-Oxo-3,4-dihydro-pyrido[2,3-d]pyrimidin-2-ylmethyl)-carbamic acid 2-chloro-benzyl ester Triethylamine (0.26 ml), 2-chlorobenzyl chloroformate ([39545-31-8], 130 mg) and DMAP (8 mg) were added to a solution of 2-aminomethyl-3H-pyrido[2,3-d]pyrimidin-4-one (25.1, 150 mg) in dichloromethane (3 ml). The mixture was kept overnight at r.t., and then diluted with dichloromethane and washed with water. After drying (Na$_2$SO$_4$) and evaporation of the solvent, the title compound was isolated from the reaction mixture by preparative, reversed-phase HPLC (Agilent Zorbax XdB C18 column, solvent gradient 5-95% CH$_3$CN in 0.1% TFA(aq) over 7 min, flow rate 30 ml/min). MS: m/e=343.0 [M−H$^-$].

Example 61

2-[3-(3-Fluoro-phenoxy)-propoxy]-3H-pyrido[2,3-d]pyrimidin-4-one

The title compound was obtained in analogy to example 28 from 3-(3-fluoro-phenoxy)-propan-1-ol [133077-41-5]. MS: m/e=314.1 [M−H$^-$].

Example 62

2-(3-m-Tolyloxy-propoxy)-3H-pyrido[2,3-d]pyrimidin-4-one

The title compound was obtained in analogy to example 28 from 3-m-tolyloxy-propan-1-ol [13030-21-2]. MS: m/e=310.4 [M−H$^-$].

Example 63

2-[2-(2-Trifluoromethyl-phenyl)-ethoxymethyl]-3H-pyrido[2,3-d]pyrimidin-4-one

The title compound was prepared from 2-(2-trifluoromethyl-phenyl)-ethanol [94022-96-5] in analogy to example 36. MS: m/e=348.4 [M−H$^-$].

Example 64

2-[2-(2-Methoxy-phenyl)-ethoxymethyl]-3H-pyrido[2,3-d]pyrimidin-4-one

The title compound was prepared from 2-(2-methoxy-phenyl)-ethanol [7417-18-7] in analogy to example 36. MS: m/e=310.4 [M−H$^-$].

Example 65

2-(2-o-Tolyl-ethoxymethyl)-3H-pyrido[2,3-d]pyrimidin-4-one

The title compound was prepared from 2-o-tolyl-ethanol [19819-98-8] in analogy to example 36. MS: m/e 296.5 [M+H$^+$].

Example 66

2-[2-(2-Chloro-phenyl)-ethoxymethyl]-3H-pyrido[2,3-d]pyrimidin-4-one

The title compound was prepared from 2-(2-chloro-phenyl)-ethanol [19819-95-5] in analogy to example 36. MS: m/e=314.1 [M−H⁻].

Example 67

2-Phenethyloxy-3H-pyrido[2,3-d]pyrimidin-4-one

The title compound was prepared from 2-phenyl-ethanol [60-12-8] in analogy to example 28. MS: m/e=268.2 [M+H⁺].

Example 68

2-(3,4-Dichloro-benzyloxy)-3H-pyrido[2,3-d]pyrimidin-4-one

The title compound was prepared from (3,4-dichloro-phenyl)-methanol [1805-32-9] in analogy to example 28. MS: m/e=322.1 [M+H⁺].

Example 69

2-[2-(4-Fluoro-phenyl)-ethoxy]-3H-pyrido[2,3-d]pyrimidin-4-one

The title compound was prepared from 2-(4-fluoro-phenyl)-ethanol [7589-27-7] in analogy to example 28. MS: m/e=286.1 [M+H⁺].

Example 70

2-(2,4-Difluoro-benzyloxy)-3H-pyrido[2,3-d]pyrimidin-4-one

The title compound was prepared from (2,4-difluoro-phenyl)-methanol [56456-47-4] in analogy to example 28. MS: m/e=290.0 [M+H⁺].

Example 71

2-[2-(4-Chloro-phenyl)-ethoxy]-3H-pyrido[2,3-d]pyrimidin-4-one

The title compound was prepared from 2-(4-chloro-phenyl)-ethanol [1875-88-3] in analogy to example 28. MS: m/e=302.1 [M+H⁺].

Example 72

2-(5-Phenyl-pentyloxy)-3H-pyrido[2,3-d]pyrimidin-4-one

The title compound was prepared from 5-phenyl-pentan-1-ol [10521-91-2] in analogy to example 28. MS: m/e=310.1 [M+H⁺].

Example 73

2-(6-Phenyl-hexyloxy)-3H-pyrido[2,3-d]pyrimidin-4-one

The title compound was prepared from 6-phenyl-hexan-1-ol [10521-91-2] in analogy to example 28. MS: m/e=324.3 [M+H⁺].

Example 74

2-[3-(4-Chloro-phenoxy)-propoxy]-3H-pyrido[2,3-d]pyrimidin-4-one

The title compound was obtained in analogy to example 28 from 3-(4-chloro-phenoxy)-propan-1-ol [18673-04-6]. MS: m/e=330.3 [M−H⁻].

Example 75

2-[3-(2-Chloro-phenoxy)-propoxy]-3H-pyrido[2,3-d]pyrimidin-4-one

The title compound was obtained in analogy to example 28 from 3-(4-chloro-phenoxy)-propan-1-ol [18673-04-6]. MS: m/e=330.3 [M−H⁻].

Example 76

2-[2-(3-Chloro-phenyl)-ethoxymethyl]-3H-pyrido[2,3-d]pyrimidin-4-one

The title compound was obtained in analogy to example 28 from 3-(2-chloro-phenoxy)-propan-1-ol [60222-56-2]. MS: m/e=330.3 [M−H⁻].

Example 77

(6-Methyl-4-oxo-3,4-dihydro-pyrido[2,3-d]pyrimidin-2-ylmethyl)-carbamic acid benzyl ester The title compound was obtained in analogy to example 28 from 3-(3-chloro-phenoxy)-propan-1-ol [57264-55-8]. MS: m/e=323.5 [M−H⁻].

Example 78

6-Chloro-2-[2-(2,5-difluoro-phenyl)-ethoxymethyl]-3H-pyrido[2,3-d]pyrimidin-4-one 78.1

Ethyl iodoacetate (340 μg, 12.9 mmol) was added to an ice cold solution of 2-(2,5-difluoro-phenyl)-ethanol (500 mg, 2.4 mmol), silver trifluoromethanesulfonate (685 mg, 2.7 mmol) and 2,6-di-tert-butylpyridin (820 μl, 3.6 mmol) in dichloromethane (5 ml). The reaction mixture was stirred at ambient temperature for 14 h, diluted with dichloromethane and filtered over speedex. Ice water/0.1 N aqueous HCl 1/1 was added to the filtrate and the filtrate was extracted two times with dichloromethane. The combined extracts were washed with aqueous NaHCO₃ solution and brine and dried over sodium sulfate. Removal of the solvent under reduced pressure left a colorless oil which was purified by column chromatography (silica gel, isopropyl acetate/heptane) to give [2-(2,5-difluoro-phenyl)-ethoxy]-acetic acid ethyl ester (320 mg, 1.3 mmol; 54%) as colorless oil. MS: m/e=245.0 [M+H⁺].

78.2

A 2 M solution of trimethylaluminum in toluene (3.3 ml, 7 mmol) was added within 10 min to an ice cold suspension of dry ammonium chloride (350 mg, 7 mmol) in toluene (4 ml). The mixture was stirred for 1 h at ambient temperature. A solution of [2-(2,5-difluoro-phenyl)-ethoxy]-acetic acid ethyl ester (320 mg, 1.3 mmol) in toluene (2 ml) was added and the reaction mixture was warmed to 80° C. for 14 h. Cooling to 0° C. was followed by the careful addition of methanol (5 ml) and stirring for 30 min at ambient temperature. The solid was filtered off and washed with methanol. The filtrate was brought to dryness and treated with iPrOH/acetone 4/1 (12 ml) for 2 h. The solid was filtered off and the filtrate was brought to dryness to give 2-[2-(2,5-difluoro-phenyl)-ethoxy]-acetamidine hydrochloride (385 mg, 1.5 mmol; quant.) as yellow crystals. MS: m/e=215.4 [M+H$^+$].

78.3

2,5-Dichloronicotinic acid (50 mg, 260 μmol), TBTU (88 mg, 273 μmol) and DIPEA (130 μl, 781 μmol) were added to a solution of 2-[2-(2,5-difluoro-phenyl)-ethoxy]-acetamidine hydrochloride (65 mg, 260 μmol) in DMF (1 ml). The solution was stirred for 72 h at ambient temperature and poured onto ice water/dichloromethane 1/1. The layers were separated, the aqueous layer was extracted two times with dichloromethane, the combined extracts were washed with brine and dried over sodium sulfate. Removal of the solvent under reduced pressure yielded 2,5-dichloro-N-{2-[2-(2,5-difluoro-phenyl)-ethoxy]-1-imino-ethyl}-nicotinamide (97 mg, 250 μmol; 96%) as orange oil which was used in the next step without further purification. MS: m/e=388.2 [M+H$^+$].

78.4

KOtBu (28 mg, 250 μmol) was added at ambient temperature to a solution of 2,5-dichloro-N-{2-[2-(2,5-difluoro-phenyl)-ethoxy]-1-imino-ethyl}-nicotinamide (97 mg, 250 μmol) in DMSO (1 ml). The solution was stirred for 1 h at 50° C., cooled to ambient temperature, KOtBu (28 mg, 250 μmol) was added and the reaction solution was stirred at 50° C. for 14 h. The mixture was poured onto isopropyl acetate/ice water 1/1. The layers were separated and the aqueous layer was extracted two times with isopropyl acetate. The combined extracts were washed three times with brine and dried over sodium sulfate. The solvent was removed under reduced pressure to leave a yellow solid which was recrystallized from dichloromethane/heptane to give 6-chloro-2-[2-(2,5-difluoro-phenyl)-ethoxymethyl]-3H-pyrido[2,3-d]pyrimidin-4-one (8 mg, 23 mmol; 9%) as yellow crystals. MS: m/e=352.3 [M+H$^+$].

Example 79

6-Chloro-2-[2-(3-chloro-phenyl)-ethoxymethyl]-3H-pyrido[2,3-d]pyrimidin-4-one 79.1

To a solution of 2-(3-chloro-phenyl)-ethanol (1.96 g, 12.51 mmol) in THF (55 ml) was added n-BuLi (8.8 ml, 1.6 M solution in hexane, 13.77 mmol) at −78° C. Then sodium iodoacetate (2.6 g, 12.51 mmol) was added and the mixture was allowed to warm to ambient temperature and was stirred overnight. The THF was then removed and 1 N HCl was added to the remaining residue to adjust the pH to 1. This mixture was extracted two times with dichloromethane and the combined extracts were dried (Na$_2$SO$_4$) and evaporated. The remaining red liquid was dissolved in MeOH (60 ml) and thionylchloride (1.56 ml, 21.5 mmol) was added dropwise at −15° C. The reaction mixture was then stirred for 1.5 h at ambient temperature. Then water was added and the mixture was extracted three times with ether. The combined extracts were washed with brine, dried (Na$_2$SO$_4$) and evaporated. The remaining residue was then purified by column chromatography (silica gel, heptane/ethyl acetate 95:5 to 88:12) to give [2-(3-chloro-phenyl)-ethoxy]-acetic acid methyl ester (2.161 g, 9.45 mmol; 76%) as orange liquid. MS: m/e=229.2 [M+H$^+$].

79.2

In analogy to the procedure described in example 78.2, [2-(3-chloro-phenyl)-ethoxy]-acetic acid methyl ester was treated with trimethylaluminum and ammonium chloride to obtain 2-[2-(3-chloro-phenyl)-ethoxy]-acetamidine hydrochloride as brown oil. MS: m/e=213.1 [M+H$^+$].

79.3

In analogy to the procedure described in example 78.3, 2,5-dichloronicotinic acid was reacted with 2-[2-(3-chlorophenyl)-ethoxy]-acetamidine hydrochloride in the presence of TBTU and DIPEA to give 2,5-dichloro-N-{2-[2-(3-chloro-phenyl)-ethoxy]-1-imino-ethyl}-nicotinamide as orange oil. MS: m/e=388.1 [M+H$^+$].

79.4

In analogy to the procedure described in example 78.4, 2,5-dichloro-N-{2-[2-(3-chloro-phenyl)-ethoxy]-1-imino-ethyl}-nicotinamide was treated with KOtBu to obtain 6-chloro-2-[2-(3-chloro-phenyl)-ethoxymethyl]-3H-pyrido[2,3-d]pyrimidin-4-one as colorless crystals. MS: m/e=350.2 [M+H$^+$].

Example 80

6-Chloro-2-[2-(4-fluoro-phenyl)-ethoxymethyl]-3H-pyrido[2,3-d]pyrimidin-4-one 80.1

In analogy to the procedure described in example 78.1, 2-(4-fluoro-phenyl)-ethanol was reacted with ethyl iodoacetate in the presence of silver trifluoromethanesulfonate and 2,6-di-tert-butylpyridin to give [2-(4-fluoro-phenyl)-ethoxy]-acetic acid ethyl ester as colorless liquid. $^1$H NMR (CDCl$_3$): 1.28 (t, J=7.2 Hz, 3H), 2.92 (t, J=7.0 Hz, 2H), 3.73 (t, J=7.0 Hz, 2H), 4.07 (s, 2H), 4.22 (q, J=7.2 Hz, 2H), 6.97 (m, 2H), 7.21 (m, 2H).

80.2

In analogy to the procedure described in example 78.2, [2-(4-fluoro-phenyl)-ethoxy]-acetic acid ethyl ester was treated with trimethylaluminum and ammonium chloride to obtain 2-[2-(4-fluoro-phenyl)-ethoxy]-acetamidine hydrochloride as yellow solid. MS: m/e=197.1 [M+H$^+$].

80.3

In analogy to the procedure described in example 78.3, 2,5-dichloronicotinic acid was reacted with 2-[2-(4-fluorophenyl)-ethoxy]-acetamidine hydrochloride in the presence of TBTU and DIPEA to give 2,5-dichloro-N-{2-[2-(4-fluorophenyl)-ethoxy]-1-imino-ethyl}-nicotinamide as orange oil. MS: m/e=370.0 [M+H$^+$].

80.4

In analogy to the procedure described in example 78.4, 2,5-dichloro-N-{2-[2-(4-fluoro-phenyl)-ethoxy]-1-imino-ethyl}-nicotinamide was treated with KOtBu to obtain 6-chloro-2-[2-(4-fluoro-phenyl)-ethoxymethyl]-3H-pyrido[2,3-d]pyrimidin-4-one as yellow crystals. MS: m/e=334.4 [M+H$^+$].

Example 81

6-Chloro-2-[2-(3-trifluoromethoxy-phenyl)-ethoxymethyl]-3H-pyrido[2,3-d]pyrimidin-4-one 81.1

In analogy to the procedure described in example 78.1, 2-(3-trifluoromethoxy-phenyl)-ethanol was reacted with ethyl iodoacetate in the presence of silver trifluoromethanesulfonate and 2,6-di-tert-butylpyridin to give [2-(3-trifluoromethoxy-phenyl)-ethoxy]-acetic acid ethyl ester as colorless oil. MS: m/e=293.1 [M+H$^+$].

81.2

In analogy to the procedure described in example 78.2, [2-(3-trifluoromethoxy-phenyl)-ethoxy]-acetic acid ethyl ester was treated with trimethylaluminum and ammonium chloride to obtain 2-[2-(3-trifluoromethoxy-phenyl)-ethoxy]-acetamidine hydrochloride as orange oil. MS: m/e=263.1 [M+H$^+$].

81.3

In analogy to the procedure described in example 78.3, 2,5-dichloronicotinic acid was reacted with 2-[2-(3-trifluoromethoxy-phenyl)-ethoxy]-acetamidine hydrochloride in the presence of TBTU and DIPEA to give 2,5-dichloro-N-{1-imino-2-[2-(3-trifluoromethoxy-phenyl)-ethoxy]-ethyl}-nicotinamide as orange oil. MS: m/e=436.2 [M+H$^+$].

81.4

In analogy to the procedure described in example 78.4, 2,5-dichloro-N-{1-imino-2-[2-(3-trifluoromethoxy-phenyl)-ethoxy]-ethyl}-nicotinamide was treated with KOtBu to obtain 6-chloro-2-[2-(3-trifluoromethoxy-phenyl)-ethoxymethyl]-3H-pyrido[2,3-d]pyrimidin-4-one as colorless crystals. MS: m/e=400.1 [M+H$^+$].

Example 82

6-Chloro-2-[2-(3-chloro-4-fluoro-phenyl)-ethoxymethyl]-3H-pyrido[2,3-d]pyrimidin-4-one 82.1

In analogy to the procedure described in example 78.1, 2-(3-chloro-4-fluoro-phenyl)-ethanol was reacted with ethyl iodoacetate in the presence of silver trifluoromethanesulfonate and 2,6-di-tert-butylpyridin to give [2-(3-chloro-4-fluoro-phenyl)-ethoxy]-acetic acid ethyl ester as colorless oil. MS: m/e=261.2 [M+H$^+$].

82.2

In analogy to the procedure described in example 78.2, [2-(3-chloro-4-fluoro-phenyl)-ethoxy]-acetic acid ethyl ester was treated with trimethylaluminum and ammonium chloride to obtain 2-[2-(3-chloro-4-fluoro-phenyl)-ethoxy]-acetamidine hydrochloride as yellow crystals. MS: m/e=231.2 [M+H$^+$].

82.3

In analogy to the procedure described in example 78.3, 2,5-dichloronicotinic acid was reacted with 2-[2-(3-chloro-4-fluoro-phenyl)-ethoxy]-acetamidine hydrochloride in the presence of TBTU and DIPEA to give 2,5-dichloro-N-{2-[2-(3-chloro-4-fluoro-phenyl)-ethoxy]-1-imino-ethyl}-nicotinamide as orange oil. MS: m/e=404.2 [M+H$^+$].

82.4

In analogy to the procedure described in example 78.4, 2,5-dichloro-N-{2-[2-(3-chloro-4-fluoro-phenyl)-ethoxy]-1-imino-ethyl}-nicotinamide was treated with KOtBu to obtain 6-chloro-2-[2-(3-chloro-4-fluoro-phenyl)-ethoxymethyl]-3H-pyrido[2,3-d]pyrimidin-4-one as orange crystals. MS: m/e=368.0 [M+H$^+$].

Example 83

6-Chloro-2-[2-(4-chloro-phenyl)-ethoxymethyl]-3H-pyrido[2,3-d]pyrimidin-4-one 83.1

In analogy to the procedure described in example 78.1, 2-(4-chloro-phenyl)-ethanol was reacted with ethyl iodoacetate in the presence of silver trifluoromethanesulfonate and 2,6-di-tert-butylpyridin to give [2-(4-chloro-phenyl)-ethoxy]-acetic acid ethyl ester as colorless liquid. MS: m/e=243.2 [M+H$^+$].

83.2

In analogy to the procedure described in example 78.2, [2-(4-chloro-phenyl)-ethoxy]-acetic acid ethyl ester was treated with trimethylaluminum and ammonium chloride to obtain 2-[2-(4-chloro-phenyl)-ethoxy]-acetamidine hydrochloride as white solid. $^1$H NMR (d$^6$-DMSO): 2.89 (t, J=6.9 Hz, 2H), 3.69 (t, J=6.9 Hz, 2H), 4.29 (s, 2H), 7.273-7.38 (m, 4H), 8.93 (s br, 4H).

83.3

In analogy to the procedure described in example 78.3, 2,5-dichloronicotinic acid was reacted with 2-[2-(4-chlorophenyl)-ethoxy]-acetamidine hydrochloride in the presence of TBTU and DIPEA to give 2,5-dichloro-N-{2-[2-(4-chloro-phenyl)-ethoxy]-1-imino-ethyl}-nicotinamide as yellow oil. MS: m/e=388.1 [M+H$^+$].

83.4

In analogy to the procedure described in example 78.4, 2,5-dichloro-N-{2-[2-(4-chloro-phenyl)-ethoxy]-1-imino-ethyl}-nicotinamide was treated with KOtBu to obtain 6-chloro-2-[2-(4-chloro-phenyl)-ethoxymethyl]-3H-pyrido[2,3-d]pyrimidin-4-one as orange crystals. MS: m/e=350.2 [M+H$^+$].

Example 84

3-(3-Fluoro-phenyl)-N-(4-oxo-3,4-dihydro-pyrido[2,3-d]pyrimidin-2-ylmethyl)-propionamide 84.1

To a solution of 2-amino-nicotinamide [13438-65-8] (3.0 g, 21.9 mmol) in CH$_2$Cl$_2$ (120 ml) and pyridine (10.56 ml, 131.3 mmol) was added phthalyl-glycyl-chloride (5.87 g, 26.3 mmol) at 0° C. The solution turned to a white suspension while stirring 0.5 hours at 0° C. and 1 hour at ambient temperature. The solid was filtrated and washed with CH$_2$Cl$_2$ to obtain 2-[2-(1,3-dioxo-1,3-dihydro-isoindol-2-yl)-acetylamino]-nicotinamide (7.10 g, 21.9 mmol; 100%) as white solid. MS (m/e): 325.1 [M+H$^+$].

84.2

A solution of 2-[2-(1,3-dioxo-1,3-dihydro-isoindol-2-yl)-acetylamino]-nicotinamide (7.24 g, 22.3 mmol) and DIPEA (14.4 ml, 111.6 mmol) in DMF (250 ml) was stirred overnight at 100° C. The reaction mixture was evaporated, redissolved in toluene and brought to dryness under reduced pressure. The residue was triturated with 100 ml EtOAc/MeOH (19/1) and filtrated to yield 2-(4-oxo-3,4-dihydro-pyrido[2,3-d]pyrimidin-2-ylmethyl)-isoindole-1,3-dione (6.03 g, 19.7 mmol; 88%) as light brown solid. MS (m/e): 307.2 [M+H$^+$].

84.3

A suspension of 2-(4-oxo-3,4-dihydro-pyrido[2,3-d]pyrimidin-2-ylmethyl)-isoindole-1,3-dione (1.0 g, 3.26 mmol) and hydrazine monohydrate (0.48 ml, 9.79 mmol) in ethanol (90 ml) was stirred at 50° C. for 3 hours. The mixture was cooled to ambient temperature and sodium carbonate (0.38 g, 3.59 mmol) and water (1 ml) were added. The suspension was stirred overnight at ambient temperature. The solid residue was filtered off, triturated with CH$_2$Cl$_2$/MeOH (4/1) under reflux conditions. A white solid was filtered off and triturated with TBME to yield 2-aminomethyl-3H-pyrido[2,3-d]pyrimidin-4-one (0.285 g, 1.62 mmol; 50%), as white solid. MS (m/e): 176.8 [M+H$^+$].

84.4

To a suspension of 2-aminomethyl-3H-pyrido[2,3-d]pyrimidin-4-one (77 mg, 0.39 mmol) in acetonitrile (4 ml) and DMF (0.5 ml) were added successively DIPEA (0.30 ml, 1.78 mmol), 3-(3-fluorophenyl)propionic acid (60 mg, 0.36 mmol) and BOP—Cl (136 mg, 0.54 mmol). The reaction mixture was stirred for 1 hour at ambient temperature, evaporated and triturated with CH$_2$Cl$_2$/MeOH (4/1). Filtration delivered 3-(3-fluoro-phenyl)-N-(4-oxo-3,4-dihydro-pyrido[2,3-d]pyrimidin-2-ylmethyl)-propionamide (30 mg, 92 μmol; 26%) as white solid. MS (m/e): 327.3 [M+H$^+$].

Example 85

2-[2-(3-Chloro-phenyl)-ethoxymethyl]-6-fluoro-3H-pyrido[2,3-d]pyrimidin-4-one

To a solution of 2,5-difluoropyridine-3-carboxylic acid (150 mg, 0.94 mmol) in CH$_2$Cl$_2$ (5 ml) at 0° C. was added oxalylchloride (97 μl, 1.13 mmol) dropwise followed by 2 drops of DMF. The reaction mixture was warmed to room temperature and stirred for 4 h. The reaction mixture was concentrated in vacuo and used in the next step without further purification. The crude acid chloride was dissolved in MeCN (5 ml) and N,N-diisopropyl ethyl amine (345 μl, 2.67 mmol) was added followed by 2-[2-(3-chlorophenyl)-ethoxy]-acetamidine hydrochloride salt (222 mg, 0.89 mmol) (prepared as described in example 79.2). The reaction mixture was stirred at room temperature for 16 h and then heated to reflux for an additional 16 h. The reaction mixture was cooled to room temperature and concentrated in vacuo to give a residue which was partitioned between water and ethyl acetate. The organic phases were combined, washed with 1N HCl, sat. NaHCO$_3$, brine, dried over MgSO$_4$, filtered and concentrated in vacuo to give a crude residue which was triturated with ether (3×5 ml) to give the desired product 2-[2-(3-chlorophenyl)-ethoxymethyl]-6-fluoro-3H-pyrido[2,3-d]pyrimidin-4-one (65 mg, 0.19 mmol; 22%) as an off white solid. MS: m/e=334.1 [M+H$^+$].

Example 86

2-[2-(3-Chloro-phenyl)-ethoxymethyl]-7-fluoro-3H-pyrido[2,3-d]pyrimidin-4-one

The title compound was prepared in analogy to example 85 from 2,6-difluoropyridine-3-carboxylic acid and 2-[2-(3-chloro-phenyl)-ethoxy]-acetamidine hydrochloride (example 79.2). Light brown solid. MS: m/e=334.1 [M+H$^+$].

Example 87

2-(5-Methyl-2-phenyl-oxazol-4-yl)-N-(4-oxo-3,4-dihydro-pyrido[2,3-d]pyrimidin-2-ylmethyl)-acetamide In analogy to example 84.4, from 2-aminomethyl-3H-pyrido[2,3-d]pyrimidin-4-one (example 84.3) and (5-methyl-2-phenyl-oxazol-4-yl)-acetic acid [107367-98-6] was prepared 2-(5-methyl-2-phenyl-oxazol-4-yl)-N-(4-oxo-3,4-dihydro-pyrido[2,3-d]pyrimidin-2-ylmethyl)-acetamide as a white solid. MS (m/e): 376.3 [M+H$^+$].

Example 88

2-[1,2,4]Triazol-1-ylmethyl-3H-pyrido[2,3-d]pyrimidin-4-one 88.1

To a solution of 2-amino-nicotinamide (200 mg, 1.4 mmol) in DMF (3 ml) was added successively 1H-1,2,4-triaazole-1-acetic acid [28711-29-7] (185 mg, 1.4 mmol), diisopropylethylamine [7087-68-5] (200 μl, 1.4 mmol) and O-(7-azabenzotriazol-1-yl)-N,N,N',N'-tetramethyluronium hexafluorophosphatehexafluorophosphate [200731-31-3] (555 mg, 1.4 mmol) at r.t. The reaction mixture was stirred for 18 hours. The solvent was removed in vacuo, and the residue was digested with dichloromethane to yield product as an off-white solid. Filtration and drying gave 206 mg of 2-(2-[1,2,4]triazol-1-yl-acetylamino)-nicotinamide as off-white solid, which was used without further purification in the next step.

88.2

2-(2-[1,2,4]Triazol-1-yl-acetylamino)-nicotinamide (206 mg, 0.8 mmol) was dissolved in pyridine (4 ml). The solution was microwaved for 15 min at 150° C. The solvent was removed in vacuo, and the residue purified by chromatography on silica (dichloromethane/methanol gradient) to yield 2-[1,2,4]triazol-1-ylmethyl-3H-pyrido[2,3-d]pyrimidin-4-one (18 mg, 72 μmol; 9%) as a yellow solid. MS (m/e): 229.1 [M+H$^+$].

Example 89

2-(3-Chloro-phenoxy)-N-(4-oxo-3,4-dihydro-pyrido[2,3-d]pyrimidin-2-ylmethyl)-acetamide In analogy to example 84.4, from 2-aminomethyl-3H-pyrido[2,3-d]pyrimidin-4-one (example 84.3) and 3-chlorophenoxyacetic acid [588-32-9] was prepared 2-(3-chloro-phenoxy)-N-(4-oxo-3,4-dihydro-pyrido[2,3-d]pyrimidin-2-ylmethyl)-acetamide as a white solid. MS (m/e): 345.2 [M+H$^+$].

Example 90

N-(4-Oxo-3,4-dihydro-pyrido[2,3-d]pyrimidin-2-ylmethyl)-2-(pyridin-2-yloxy)-acetamide In analogy to example 84.4, from 2-aminomethyl-3H-pyrido[2,3-d]pyrimidin-4-one (example 84.3) and (2-pyridinyloxy)-acetic acid [58530-50-0] was prepared N-(4-oxo-3,4-dihydro-pyrido[2,3-d]pyrimidin-2-ylmethyl)-2-(pyridin-2-yloxy)-acetamide as a white solid. MS (m/e): 312.0 [M+H$^+$].

Example 91

2-[2-(3-Fluoro-phenyl)-ethoxymethyl]-3H-pyrido[2,3-d]pyrimidin-4-one 91.1

To a solution of 2-(3-fluoro-phenyl)-ethanol (4.0 g, 28.5 mmol) in DMF (60 ml) was added a 60% dispersion of sodium hydride in oil (2.40 g, 60 mmol). The suspension was heated to 60° C. for 0.75 hours. Chloroacetic acid (4.72 g, 50 mmol) was added dropwise. After 36 hours at 60° C. the brown reaction mixture was brought to dryness under reduced pressure, dissolved in EtOAc and washed with 1M HCl, water and brine. The organic layers were dried over MgSO$_4$, filtrated, the solvent was removed under reduced pressure and the residue purified by column chromatography (silica gel, EtOAc/heptane, 3/1) to yield [2-(3-fluoro-phenyl)-ethoxy]-acetic acid (2.02 g, 18 mmol; 36%) as colorless liquid. MS (m/e): 197.4 [M−H]$^-$.

91.2

A solution of [2-(3-fluoro-phenyl)-ethoxy]-acetic acid (1.20 g, 6.05 mmol), EDCI (1.28 g, 6.66 mmol), HOBt (0.90 g, 6.66 mmol) and DIPEA (1.56 ml, 9.08 mmol) in methanol (4 ml) was stirred at 0° C. for 2 hours. The reaction mixture was brought to dryness, dissolved in CH$_2$Cl$_2$ and washed twice with 1M NaOH and brine. The organic layers were dried over MgSO$_4$, filtrated, the solvent was removed under reduced pressure and the residue was purified by column chromatography (silica gel, EtOAc/heptane, 1/4) to yield [2-(3-fluoro-phenyl)-ethoxy]-acetic acid methyl ester (1.20 g, 5.6 mmol; 93%) as colorless liquid. MS (m/e): 213.2 [M+H]$^+$.

91.3

A suspension of 2-amino-nicotinamide (250 mg, 1.82 mmol) and [2-(3-fluoro-phenyl)-ethoxy]-acetic acid methyl ester (464 mg, 2.18 mmol) in THF (5 ml) was treated with LiHMDS (1M THF solution, 4.6 ml) overnight at ambient temperature. The yellow suspension was filtrated, the filtrate was brought to dryness and the residue was purified by column chromatography (amino-phase silica gel, CH$_2$Cl$_2$/MeOH, 19/1) to give 2-[2-(3-fluoro-phenyl)-ethoxymethyl]-3H-pyrido[2,3-d]pyrimidin-4-one (303 mg, 1 mmol; 55%) as white solid. MS (m/e): 300.2 [M+H]$^+$

Example 92

2-[2-(3-Methoxy-phenyl)-ethoxymethyl]-3H-pyrido[2,3-d]pyrimidin-4-one

In analogy to example 91.3, 2-amino-nicotinamide and [2-(3-methoxy-phenyl)-ethoxy]-acetic acid methyl ester (prepared from 2-(3-methoxyphenyl)ethanol [5020-41-7] in analogy to example 91.1-91.2) reacted in the presence of LiHMDS in THF to yield after purification of the crude product with column chromatography (silica gel, EtOAc) 2-[2-(3-methoxy-phenyl)-ethoxymethyl]-3H-pyrido[2,3-d]pyrimidin-4-one as white solid. MS (m/e): 312.2 [M+H$^+$].

Example 93

7-Fluoro-2-[4-(4-fluoro-phenyl)-butyl]-3H-pyrido[2,3-d]pyrimidin-4-one 93.1

Thionylchloride (288 µl, 3.98 mmol) was added dropwise to a solution of 5-(4-fluoro-phenyl)-pentanoic acid (520 mg, 2.65 mmol) in methanol (11 ml) at −15° C. The reaction mixture was then stirred at room temperature for 1.5 h. Water was added and the mixture was extracted 3 times with diethylether. The combined extracts were washed with water and brine, dried (Na$_2$SO$_4$) and evaporated. The remaining residue was purified by column chromatography (silica gel, ethyl acetate/heptane 5:95 to 12:88) to obtain 5-(4-fluoro-phenyl)-pentanoic acid methyl ester (420 mg, 2 mmol; 75%) as colorless liquid. MS: m/e 211.0 [M+H$^+$].

93.2

In analogy to the procedure described in example 78.2, 5-(4-fluoro-phenyl)-pentanoic acid methyl ester was treated with trimethylaluminum and ammonium chloride to obtain 5-(4-fluoro-phenyl)-pentanamidine hydrochloride as off-white solid. MS: m/e=195.2 [M+H$^+$].

93.3

The title compound was prepared in analogy to example 85 from 2,6-difluoropyridine-3-carboxylic acid and 5-(4-fluoro-phenyl)-pentanamidine hydrochloride. White solid. MS: m/e=316.1 [M+H$^+$].

Example 94

7-Fluoro-2-[2-(2-fluoro-phenyl)-ethoxymethyl]-3H-pyrido[2,3-d]pyrimidin-4-one 94.1

In analogy to the procedure described in example 79.1, 2-(2-fluorophenyl)-ethanol was converted to [2-(2-fluorophenyl)-ethoxy]-acetic acid methyl ester. Yellow oil. MS: m/e=213.1 [M+H$^+$].

94.2

In analogy to the procedure described in example 78.2, [2-(2-fluorophenyl)-ethoxy]-acetic acid methyl ester was treated with trimethylaluminum and ammonium chloride to obtain 2-[2-(3-chloro-phenyl)-ethoxy]-acetamidine hydrochloride as colorless oil. MS: m/e=197.2 [M+H$^+$].

94.3

The title compound was synthesized in analogy to example 85 using 2,6-difluoropyridine-3-carboxylic acid and 2-[2-(2-fluorophenyl)-ethoxy]-acetamidine to give 7-fluoro-2-[2-(2-fluorophenyl)-ethoxymethyl]-3H-pyrido[2,3-d]pyrimidin-4-one as the desired product (80%) as a white solid. MS: m/e=318.2 [M+H$^+$].

Example 95

N-(6-Fluoro-4-oxo-3,4-dihydro-pyrido[2,3-d]pyrimidin-2-ylmethyl)-3-phenyl-propionamide 95.1

A suspension of 2-chloro-5-fluoro-nicotinic acid (2.0 g, 11.39 mmol), HOBt (2.31 g, 17.13 mmol), BOP—Cl (4.37 g, 17.15 mmol), ammonium chloride (1.22 g, 22.86 mmol), DIPEA (12 ml, 66.74 mmol) in DMF (75 ml) was stirred at ambient temperature for 18 hours. The reaction mixture was diluted with EtOAc and washed with water and brine. The organic phases were dried over MgSO$_4$, filtrated and evaporated. The crude product was purified by column chromatography (silica gel, EtOAc) to obtain 2-chloro-5-fluoro-nicotinamide (850 mg, 4.9 mmol; 43%) as white solid. MS (m/e): 175.1 [M+H$^+$].

95.2

A solution of 2-chloro-5-fluoro-nicotinamide (70 mg, 0.40 mmol) and 4-methoxybenzylamine (550 mg, 4.01 mmol) in ethyleneglycol (1 ml) was microwaved for 50 min at 140° C. A white solid was filtered off and the filtrate evaporated. The residue was dissolved in EtOAc, washed with water and brine, dried over MgSO$_4$ and the solvent removed under reduced pressure. The residue was purified by column chromatography (silica gel, EtOAc/heptane, 1/1) to obtain 5-fluoro-2-(4-methoxy-benzylamino)-nicotinamide (56 mg, 0.2 mmol; 51%) as white solid. MS (m/e): 276.3 [M+H$^+$].

95.3

5-Fluoro-2-(4-methoxy-benzylamino)-nicotinamide (220 mg, 0.80 mmol) in CH$_2$Cl$_2$ (2 ml) and anisole (1 ml) was treated with TFA (2.57 ml, 34.6 mmol) at 60° C. for 3 hours. The reaction mixture was brought to dryness and the residue purified by column chromatography (silica gel, EtOAc/heptane, 1/4) to yield 2-amino-5-fluoro-nicotinamide (100 mg, 0.65 mmol; 81%) as yellow solid. MS (m/e): 156.1 [M+H$^+$].

95.4

Starting from 2-amino-5-fluoro-nicotinamide, 2-aminomethyl-6-fluoro-3H-pyrido[2,3-d]pyrimidin-4-one was synthesized in analogy to example 84.1-84.3. Yellow solid. MS (m/e): 195.1 [M+H$^+$].

95.5

A solution of 2-aminomethyl-6-fluoro-3H-pyrido[2,3-d]pyrimidin-4-one (130 mg, 0.67 mmol) in THF (5 ml) was treated with DIPEA (173 mg, 1.34 mmol) and 3-phenyl-propionyl chloride (136 mg, 0.80 mmol) at 0° C. for 18 hours. The reaction mixture was diluted with EtOAc, washed with water and brine. The organic layers were dried over MgSO$_4$, filtrated, evaporated and chromatographed (silica gel, EtOAc/heptane, 1/1) to yield N-(6-fluoro-4-oxo-3,4-dihydro-pyrido [2,3-d]pyrimidin-2-ylmethyl)-3-phenyl-propionamide (6 mg, 13 µmol; 2%) as yellow solid. MS (m/e): 327.3 [M+H$^+$].

Example 96

7-Fluoro-2-[2-(3-trifluoromethyl-phenyl)-ethoxymethyl]-3H-pyrido[2,3-d]pyrimidin-4-one 96.1

In analogy to the procedure described in example 78.1, 2-(3-trifluoromethyl-phenyl)-ethanol was reacted with ethyl iodoacetate in the presence of silver trifluoromethanesulfonate and 2,6-di-tert-butylpyridin to give [2-(3-trifluoromethyl-phenyl)-ethoxy]-acetic acid ethyl ester as colorless liquid. MS: m/e=277.2 [M+H$^+$].

96.2

In analogy to the procedure described in example 78.2, [2-(3-trifluoromethyl-phenyl)-ethoxy]-acetic acid ethyl ester was treated with trimethylaluminum and ammonium chloride to obtain 2-[2-(3-trifluoromethyl-phenyl)-ethoxy]-acetamidine hydrochloride as brown solid. MS: m/e=247.2 [M+H$^+$].

96.3

The title compound was prepared in analogy to example 85 from 2,6-difluoropyridine-3-carboxylic acid and 2-[2-(3-trifluoromethyl-phenyl)-ethoxy]-acetamidine hydrochloride. Brown solid. MS: m/e=368.1 [M+H$^+$].

Example 97

5-Methyl-2-(5-phenyl-pentyloxy)-3H-pyrido[2,3-d]pyrimidin-4-one 97.1

5-Methyl-1H-pyrido[2,3-d]pyrimidine-2,4-dione (H. Junek, I. Wrtilek, *Monatsh. Chem.* 1970, 101, 1130-5; 2 g, 11 mmol) was suspended at ambient temperature in phosphorous oxychloride (7.7 ml, 85 mmol) and stirred under reflux conditions for 14 h. The reaction mixture was poured onto ice water, filtered and the filtrate was extracted two times with isopropyl acetate. The combined extracts were washed with brine, dried over sodium sulfate and the solvent was removed under reduced pressure. The crude product was purified by column chromatography (silica gel, isopropyl acetate/heptane) to give 2,4-dichloro-5-methyl-pyrido[2,3-d]pyrimidine (302 mg, 1.4 mmol; 13%) as yellow crystals. MS: m/e=214.1 [M+H$^+$].

97.2

2,4-Dichloro-5-methyl-pyrido[2,3-d]pyrimidine (302 mg, 1.4 mmol) was suspended at ambient temperature in aqueous 1N NaOH solution (6 ml) and stirred for 1 h. The pH was adjusted to 7 with aqueous 25% HCl solution and the mixture was washed two times with dichloromethane. The aqueous layer was brought to dryness under reduced pressure to give 344 mg (1.48 mmol; quant.) 2-chloro-5-methyl-3H-pyrido[2,3-d]pyrimidin-4-one hydrochloride as off-white solid which was used in the next step without further purification. MS: m/e=195.9 [M+H$^+$].

97.3

2-Chloro-5-methyl-3H-pyrido[2,3-d]pyrimidin-4-one hydrochloride (36 mg, 155 µmol) was dissolved in DMSO (0.8 ml). Molecular sieves 4Å, 5-phenyl-1-pentanol (80 µl, 465 µmmol) and potassium tert-butylate (35 mg, 310 µmol) were added and the suspension was stirred at 120° C. for 48 h under an argon atmosphere. The molecular sieves were filtered off, the filtrate was poured onto ice water/isopropyl acetate 1/1, the layers were separated and the aqueous layer was extracted two times with isopropyl acetate. The combined extracts were washed with brine, dried over sodium sulfate and the solvent was removed under reduced pressure. The crude product was purified by column chromatography (silica gel, isopropyl acetate/heptane) to give 5-methyl-2-(5- phenyl-pentyloxy)-3H-pyrido[2,3-d]pyrimidin-4-one (16 mg, 50 µmol; 32%) as yellow crystals. MS: m/e=324.4 [M+H+].

Example 98

6-Chloro-2-(3-phenoxy-propoxy)-3H-pyrido[2,3-d]pyrimidin-4-one 98.1

Under an atmosphere of nitrogen, and at a temperature of 0° C., a solution of 2,5-dichloropyridine-3-carbonyl chloride [175277-81-3] (4.82 g, 23 mmol) in CHCl$_3$ (7 ml) was slowly added to a solution of methyl aminomethanimidothioate hydroiodide [4338-95-8] (5.00 g, 23 mmol) and triethylamine (6.36 ml, 46 mmol) in pyridine (7 ml). The reaction mixture was stirred at r.t. over the weekend, was taken up in ethyl acetate and washed (water). After drying (Na$_2$SO$_4$) and evaporation of the solvent, the residue was purified (column chromatography, silica gel, CH$_2$Cl$_2$/MeOH) to give 1-(2,5-dichloro-pyridine-3-carbonyl)-2-methyl-isothiourea (3.50 g, 13 mmol; 58%). MS: m/e=262.0 [M+H+]); $^1$H NMR (d$^6$-DMSO): δ 2.44 (s, 3H), 8.27 (d, 1H), 8.55 (d, 1H), 9.15 (bs, 1H), 9.55 (bs, 1H).

98.2

A solution of 1-(2,5-dichloro-pyridine-3-carbonyl)-2-methyl-isothiourea (2.44 g, 9 mmol) in DMF (8 ml) was heated under an atmosphere of nitrogen to 157° C. for 15 min. After cooling, ethanol (8 ml) was added, the precipitated 6-chloro-2-methylsulfanyl-3H-pyrido[2,3-d]pyrimidin-4-one hydrochloride was filtered off, and residual solvents were removed in a high vacuum overnight (770 mg, 2.9 mmol; 32%). $^1$H NMR (d$^6$-DMSO): δ 3.34 (s, 3H), 8.44 (d, 1H), 8.80 (d, 1H), 8.85 (bs, 1H), 8.95 (bs, 1H).

98.3

6-Chloro-2-methylsulfanyl-3H-pyrido[2,3-d]pyrimidin-4-one hydrochloride (380 mg, 1.4 mmol) was heated in 2N HCl (1.4 ml) to reflux for 1 h. The obtained suspension was cooled, diluted with a small amount of water, and filtered. Residual solvent was removed from the obtained 6-chloro-1H-pyrido[2,3-d]pyrimidine-2,4-dione hydrochloride by high vacuum over the weekend (230 mg, 0.95 mmol; 68%). $^1$H NMR (d$^6$-DMSO): δ 3.37 (bs, 1H), 7.5 (bs, 1H), 7.8 (bs, 1H), 8.25 (d, 1H), 8.30 (d, 1H).

98.4

A mixture of 6-chloro-1H-pyrido[2,3-d]pyrimidine-2,4-dione hydrochloride (360 mg, 1.54 mmol) and phosphorus oxychloride (5.6 ml) was heated to reflux over night under an atmosphere of nitrogen. Excess phosphorus oxychloride was evaporated, the black mixture was poured into ice water, and extracted (CH$_2$Cl$_2$). The combined organic layers were dried (Na$_2$SO$_4$), and the solvent was evaporated. The crude 2,4,6-trichloro-pyrido[2,3-d]pyrimidine was used without further purification and characterization in the next step.

98.5

2,4,6-Trichloro-pyrido[2,3-d]pyrimidine (360 mg, crude) was dissolved in 1N NaOH (6 ml) (ultrasonication) and stirred for 30 min at r.t. The obtained suspension was extracted with Et$_2$O. The water layer was separated, acidified (HCl), and again extracted (EtOAc). The organic layer was dried (Na$_2$SO$_4$), filtered and evaporated to give crude 2,6-dichloro-3H-pyrido[2,3-d]pyrimidin-4-one (MS: m/e=214.3 [M−H−]) which was used without further purification in the next step.

98.6

A solution of 2,6-dichloro-3H-pyrido[2,3-d]pyrimidin-4-one (60 mg, crude), 3-phenoxy-1-propanol [6180-61-6] (127 mg, 0.84 mmol), and KOtBu (62 mg, 0.55 mmol) in DMSO (1 ml) was heated in a microwave oven to 180° C. for 15 min. After filtration, the title compound (2.3 mg, 6.9 Amok; 2.5%, MS: m/e=330.3 [M−H−]) was obtained from the reaction mixture by preparative, reverse-phase HPLC (Agilent Zorbax XdB C18 column, solvent gradient 5-95% CH$_3$CN in 0.1% TFA(aq) over 7 min, flow rate 30 ml/min).

Example 99

7-Methyl-2-(5-phenyl-pentyloxy)-3H-pyrido[2,3-d]pyrimidin-4-one 99.1

In analogy to the procedure described in example 97.2, 2,4-dichloro-7-methyl-pyrido[2,3-d]pyrimidine (R. K. Robins, G. H. Hitchings, *J. Am. Chem. Soc.* 1958, 80, 3449-57) was treated with 1N NaOH solution to give 2-chloro-7-methyl-3H-pyrido[2,3-d]pyrimidin-4-one hydrochloride as orange solid. MS: m/e=196.1 [M+H+].

99.2

In analogy to the procedure described in example 97.3, 2-chloro-7-methyl-3H-pyrido[2,3-d]pyrimidin-4-one hydrochloride was reacted with 5-phenyl-1-pentanol in DMSO in the presence of molecular sieves and potassium tert-butylate to give 7-methyl-2-(5-phenyl-pentyloxy)-3H-pyrido[2,3-d]pyrimidin-4-one as yellow crystals. MS: m/e=324.4 [M+H+].

Example 100

2-[3-(2-Chloro-phenoxy)-propoxy]-5-methyl-3H-pyrido[2,3-d]pyrimidin-4-one

In analogy to the procedure described in example 97.3, 2-chloro-5-methyl-3H-pyrido[2,3-d]pyrimidin-4-one hydrochloride was reacted with 3-(2-chloro-phenoxy)-propan-1-ol [60222-56-2] in DMSO in the presence of molecular sieves and potassium tert-butylate to give the title compound as off-white crystals. MS: m/e=346.1 [M+H+].

Example 101

7-Fluoro-2-[2-(3-fluoro-phenyl)-ethoxymethyl]-3H-pyrido[2,3-d]pyrimidin-4-one 101.1

In analogy to the procedure described in example 78.1, 2-(3-fluoro-phenyl)-ethanol was reacted with ethyl iodoacetate in the presence of silver trifluoromethanesulfonate and 2,6-di-tert-butylpyridin to give [2-(3-fluoro-phenyl)-ethoxy]-acetic acid ethyl ester as colorless liquid. MS: m/e=227.2 [M+H+].

101.2

In analogy to the procedure described in example 78.2, [2-(3-fluoro-phenyl)-ethoxy]-acetic acid ethyl ester was treated with trimethylaluminum and ammonium chloride to obtain 2-[2-(3-fluoro-phenyl)-ethoxy]-acetamidine hydrochloride as yellow solid. MS: m/e=197.1 [M+H+].

101.3

The title compound was prepared in analogy to example 85 from 2,6-difluoropyridine-3-carboxylic acid and 2-[2-(3- fluoro-phenyl)-ethoxy]-acetamidine hydrochloride. Light brown solid. MS: m/e=318.1 [M+H$^+$].

Example 102

7-Fluoro-2-[2-(4-fluoro-phenyl)-ethoxymethyl]-3H-pyrido[2,3-d]pyrimidin-4-one

The title compound was prepared in analogy to example 85 from 2,6-difluoropyridine-3-carboxylic acid and 2-[2-(4-fluoro-phenyl)-ethoxy]-acetamidine hydrochloride (example 80.2). Light brown solid. MS: m/e=318.1 [M+H$^+$].

Example 103

3-(2-Chloro-phenyl)-N-(4-oxo-3,4-dihydro-pyrido[2,3-d]pyrimidin-2-ylmethyl)-propionamide In analogy to example 84.4, from 2-aminomethyl-3H-pyrido[2,3-d]pyrimidin-4-one (example 84.3) and 3-(2-chlorophenyl)propionic acid [1643-28-3] was prepared 3-(2-chloro-phenyl)-N-(4-oxo-3,4-dihydro-pyrido[2,3-d]pyrimidin-2-ylmethyl)-propionamide as a white solid. MS (m/e): 342.9 [M+H$^+$].

Example 104

3-(3-Chloro-phenyl)-N-(4-oxo-3,4-dihydro-pyrido[2,3-d]pyrimidin-2-ylmethyl)-propionamide In analogy to example 84.4, from 2-aminomethyl-3H-pyrido[2,3-d]pyrimidin-4-one (example 84.3) and 3-(3-chlorophenyl)propionic acid [21640-48-2] was prepared 3-(3-chloro-phenyl)-N-(4-oxo-3,4-dihydro-pyrido[2,3-d]pyrimidin-2-ylmethyl)-propionamide. The crude product was purified by column chromatography (amino-phase silica gel, CH$_2$Cl$_2$/MeOH (4/1)) and subsequent trituration with TBME to give the title compound as white solid. MS (m/e): 342.9 [M+H$^+$].

Example 105

2-[2-(2-Chloro-phenyl)-ethoxymethyl]-7-fluoro-3H-pyrido[2,3-d]pyrimidin-4-one 105.1
In analogy to the procedure described in example 78.1, 2-(2-chloro-phenyl)-ethanol was reacted with ethyl iodoacetate in the presence of silver trifluoromethanesulfonate and 2,6-di-tert-butylpyridin to give [2-(2-chloro-phenyl)-ethoxy]-acetic acid ethyl ester as yellow liquid. $^1$H NMR (CDCl$_3$): 1.28 (t, J=7.3 Hz, 3H), 3.09 (t, J=7.1 Hz, 2H), 3.78 (t, J=7.1 Hz, 2H), 4.09 (s, 2H), 4.21 (q, J=7.3 Hz, 2H), 7.13-7.23 (m, 2H), 7.29-7.37 (m, 2H).

105.2
In analogy to the procedure described in example 78.2, [2-(2-chloro-phenyl)-ethoxy]-acetic acid ethyl ester was treated with trimethylaluminum and ammonium chloride to obtain 2-[2-(2-chloro-phenyl)-ethoxy]-acetamidine hydrochloride as yellow solid. MS: m/e=213.2 [M+H$^+$].

105.3
The title compound was prepared in analogy to example 85 from 2,6-difluoropyridine-3-carboxylic acid and 2-[2-(2-chloro-phenyl)-ethoxy]-acetamidine hydrochloride. Light brown solid. MS: m/e=334.2 [M+H$^+$].

Example 106

6-Chloro-2-[2-(2-chloro-phenyl)-ethoxymethyl]-3H-pyrido[2,3-d]pyrimidin-4-one 106.1
In analogy to the procedure described in example 78.3, 2,5-dichloronicotinic acid was reacted with 2-[2-(2-chloro-phenyl)-ethoxy]-acetamidine hydrochloride (example 105.2) in the presence of TBTU and DIPEA to give 2,5-dichloro-N-{2-[2-(2-chloro-phenyl)-ethoxy]-1-imino-ethyl}-nicotinamide as orange oil. MS: m/e=388.1 [M+H$^+$].

106.2
In analogy to the procedure described in example 78.4, 2,5-dichloro-N-{2-[2-(2-chloro-phenyl)-ethoxy]-1-imino-ethyl}-nicotinamide was treated with KOtBu to obtain 6-chloro-2-[2-(2-chloro-phenyl)-ethoxymethyl]-3H-pyrido[2,3-d]pyrimidin-4-one as off-white crystals. MS: m/e=350.3 [M+H$^+$].

Example 107

6-Fluoro-2-[2-(3-fluoro-phenyl)-ethoxymethyl]-3H-pyrido[2,3-d]pyrimidin-4-one

The title compound was prepared in analogy to example 85 from 2,5-difluoropyridine-3-carboxylic acid and 2-[2-(3-fluoro-phenyl)-ethoxy]-acetamidine hydrochloride (example 101). Light brown solid. MS: m/e=318.2 [M+H$^+$].

Example 108

6-Chloro-2-[4-(4-fluoro-phenyl)-butyl]-3H-pyrido[2,3-d]pyrimidin-4-one 108.1
In analogy to the procedure described in example 78.3, 2,5-dichloronicotinic acid was reacted with 5-(4-fluoro-phenyl)-pentanamidine hydrochloride (example 93.2) in the presence of TBTU and DIPEA to give 2,5-dichloro-N-[5-(4-fluoro-phenyl)-1-imino-pentyl]-nicotinamide as brown oil. MS: m/e=368.1 [M+H$^+$].

108.2
In analogy to the procedure described in example 78.4, 2,5-dichloro-N-[5-(4-fluoro-phenyl)-1-imino-pentyl]-nicotinamide was treated with KOtBu to obtain 6-chloro-2-[4-(4-fluoro-phenyl)-butyl]-3H-pyrido[2,3-d]pyrimidin-4-one as off-white crystals. MS: m/e=332.2 [M+H$^+$].

Example 109

2-[2-(2-Chloro-6-fluoro-phenyl)-ethoxymethyl]-7-fluoro-3H-pyrido[2,3-d]pyrimidin-4-one 109.1
In analogy to the procedure described in example 78.1, 2-(2-chloro-6-fluoro-phenyl)-ethanol was reacted with ethyl iodoacetate in the presence of silver trifluoromethanesulfonate and 2,6-di-tert-butylpyridin to give [2-(2-chloro-6-fluoro-phenyl)-ethoxy]-acetic acid ethyl ester as colorless liquid. $^1$H NMR (CDCl$_3$): 1.28 (t, J=7.1 Hz, 3H), 3.15 (t, J=7.1 Hz, 2H), 3.73 (t, J=7.3 Hz, 2H), 4.11 (s, 2H), 4.22 (q, J=7.1 Hz, 2H), 6.96 (m, 1H), 7.09-7.19 (m, 2H).

109.2

In analogy to the procedure described in example 78.2, [2-(2-chloro-6-fluoro-phenyl)-ethoxy]-acetic acid ethyl ester was treated with trimethylaluminum and ammonium chloride to obtain 2-[2-(2-chloro-6-fluoro-phenyl)-ethoxy]-acetamidine hydrochloride as yellow solid. MS: m/e=231.2 [M+H$^+$].

109.3

The title compound was prepared in analogy to example 85 from 2,6-difluoropyridine-3-carboxylic acid and 2-[2-(2-chloro-6-fluoro-phenyl)-ethoxy]-acetamidine hydrochloride. Off-white solid. MS: m/e=352.2 [M+H$^+$].

Example 110

2-(2-m-Tolyl-ethoxymethyl)-3H-pyrido[2,3-d]pyrimidin-4-one

In analogy to example 91.3, 2-amino-nicotinamide and (2-m-tolyl-ethoxy)-acetic acid methyl ester (prepared from 2-m-tolyl-ethanol [1875-89-4] in analogy to example 91.1-91.2) reacted in the presence of LiHMDS in THF to yield after purification of the crude product with column chromatography (silica gel, EtOAc) and crystallization from EtOAc/heptane 2-(2-m-tolyl-ethoxymethyl)-3H-pyrido[2,3-d]pyrimidin-4-one as white solid. MS (m/e): 296.4 [M+H$^+$].

Example 111

2-[2-(4-Chloro-phenyl)-ethoxymethyl]-7-fluoro-3H-pyrido[2,3-d]pyrimidin-4-one

The title compound was prepared in analogy to example 85 from 2,6-difluoropyridine-3-carboxylic acid and 2-[2-(4-chloro-phenyl)-ethoxy]-acetamidine hydrochloride (example 83.2). Off-white solid. MS: m/e=334.2 [M+H$^+$].

Example 112

3-(4-Chloro-phenyl)-N-(4-oxo-3,4-dihydro-pyrido[2,3-d]pyrimidin-2-ylmethyl)-propionamide In analogy to example 104, from 2-aminomethyl-3H-pyrido[2,3-d]pyrimidin-4-one (example 84.3) and 3-(4-chlorophenyl)propionic acid [2019-34-3] was prepared 3-(4-chloro-phenyl)-N-(4-oxo-3,4-dihydro-pyrido[2,3-d]pyrimidin-2-ylmethyl)-propionamide. The crude product was purified by column chromatography (amino-phase silica gel, CH$_2$Cl$_2$/MeOH (4/1)) and subsequent trituration with TBME to give the title compound as white solid. MS (m/e): 342.9 [M+H$^+$].

Example 113

(6-Fluoro-4-oxo-3,4-dihydro-pyrido[2,3-d]pyrimidin-2-ylmethyl)-carbamic acid benzyl ester 2,5-Difluoronicotinic acid (547 mg, 3.44 mmol), TBTU (1.33 g, 4.14 mmol) and DIPEA (3.40 ml, 19.85 mmol) were added to a solution of carbamimidoylmethyl-carbamic acid benzyl ester [77390-81-9] (725 mg, 3.51 mmol) in DMF (20 ml). The solution was stirred for 5 hours at ambient temperature and 30 hours at 90° C. The brown suspension was poured onto ice cold aqueous buffer solution pH5/dichloromethane 1/1. The layers were separated, the aqueous layer was extracted twice with dichloromethane, the combined extracts were washed with brine and dried over magnesium sulfate. Removal of the solvent under reduced pressure and crystallization (EtOAc/TBME) yielded (6-fluoro-4-oxo-3,4-dihydro-pyrido[2,3-d]pyrimidin-2-ylmethyl)-carbamic acid benzyl ester (250 mg, 0.757 mmol; 22%) as white solid. MS: m/e=327.1 [M−H$^−$].

Example 114

2-[2-(2,5-Difluoro-phenyl)-ethoxymethyl]-7-fluoro-3H-pyrido[2,3-d]pyrimidin-4-one The title compound was prepared in analogy to example 85 from 2,6-difluoropyridine-3-carboxylic acid and 2-[2-(2,5-difluoro-phenyl)-ethoxy]-acetamidine hydrochloride (example 78.2). Off-white solid. MS: m/e=336.3 [M+H$^+$].

Example 115

N-(4-Oxo-3,4-dihydro-pyrido[2,3-d]pyrimidin-2-ylmethyl)-3-m-tolyl-propionamide

In analogy to example 84.4, from 2-aminomethyl-3H-pyrido[2,3-d]pyrimidin-4-one (example 84.3) and 3-(3-methylphenyl)propionic acid [3751-48-2] was prepared N-(4-oxo-3,4-dihydro-pyrido[2,3-d]pyrimidin-2-ylmethyl)-3-m-tolyl-propionamide as a white solid. MS (m/e): 323.5 [M+H$^+$].

Example 116

7-Fluoro-2-[2-(3-trifluoromethoxy-phenyl)-ethoxymethyl]-3H-pyrido[2,3-d]pyrimidin-4-one The title compound was prepared in analogy to example 85 from 2,6-difluoropyridine-3-carboxylic acid and 2-[2-(3-trifluoromethoxy-phenyl)-ethoxy]-acetamidine hydrochloride (example 81.2). Light brown solid. MS: m/e=384.1 [M+H$^+$].

Example 117

3-(3-Methoxy-phenyl)-N-(4-oxo-3,4-dihydro-pyrido[2,3-d]pyrimidin-2-ylmethyl)-propionamide In analogy to example 84.4, from 2-aminomethyl-3H-pyrido[2,3-d]pyrimidin-4-one (example 84.3) and 3-(3-methoxyphenyl)propionic acid [10516-71-9] was prepared 3-(3-methoxy-phenyl)-N-(4-oxo-3,4-dihydro-pyrido[2,3-d]pyrimidin-2-ylmethyl)-propionamide as a white solid. MS (m/e): 339.1 [M+H$^+$].

Example 118

2-[2-(3-Chloro-4-fluoro-phenyl)-ethoxymethyl]-7-fluoro-3H-pyrido[2,3-d]pyrimidin-4-one The title compound was prepared in analogy to example 85 from 2,6-difluoropyridine-3-carboxylic acid and 2-[2-(3-chloro-4-fluoro-phenyl)-ethoxy]-acetamidine hydrochloride (example 82.2). Off-white solid. MS: m/e=352.2 [M+H$^+$].

Example 119

2-[2-(2,5-Difluoro-phenyl)-ethoxymethyl]-6-fluoro-3H-pyrido[2,3-d]pyrimidin-4-one The title compound was prepared in analogy to example 85 from 2,5-difluoropyridine-3-carboxylic acid and 2-[2-(2,5- difluoro-phenyl)-ethoxy]-acetamidine hydrochloride (example 78.2). Light brown solid. MS: m/e=336.3 [M+H⁺].

Example 120

(6-Chloro-4-oxo-3,4-dihydro-pyrido[2,3-d]pyrimidin-2-ylmethyl)-carbamic acid benzyl ester In analogy to example 78.3 and 78.4, from 2,5-dichloronicotinic acid and carbamimidoylmethyl-carbamic acid benzyl ester [77390-81-9] was prepared (6-chloro-4-oxo-3,4-dihydro-pyrido[2,3-d]pyrimidin-2-ylmethyl)-carbamic acid benzyl ester as a white solid. MS (m/e): 345.3 [M+H⁺].

Example 121

(7-Chloro-4-oxo-3,4-dihydro-pyrido[2,3-d]pyrimidin-2-ylmethyl)-carbamic acid benzyl ester In analogy to example 78.3 and 78.4, from 2,6-dichloronicotinic acid and carbamimidoylmethyl-carbamic acid benzyl ester [77390-81-9] was prepared (7-chloro-4-oxo-3,4-dihydro-pyrido[2,3-d]pyrimidin-2-ylmethyl)-carbamic acid benzyl ester as a light yellow solid. MS (m/e): 345.3 [M+H⁺].

Example 122

(7-Fluoro-4-oxo-3,4-dihydro-pyrido[2,3-d]pyrimidin-2-ylmethyl)-carbamic acid benzyl ester In analogy to example 113, from 2,6-difluoronicotinic acid and carbamimidoylmethyl-carbamic acid benzyl ester [77390-81-9] was prepared (7-fluoro-4-oxo-3,4-dihydro-pyrido[2,3-d]pyrimidin-2-ylmethyl)-carbamic acid benzyl ester (reaction time: 26 hours at ambient temperature) as a white solid. MS (m/e): 329.1 [M+H⁺].

Example 123

6-Chloro-2-(2-naphthalen-2-yl-ethoxymethyl)-3H-pyrido[2,3-d]pyrimidin-4-one 123.1
In analogy to the procedure described in example 78.1, 2-naphthalen-2-yl-ethanol was reacted with ethyl iodoacetate in the presence of silver trifluoromethanesulfonate and 2,6-di-tert-butylpyridin to give (2-naphthalen-2-yl-ethoxy)-acetic acid ethyl ester as colorless oil. MS: m/e=259.3 [M+H⁺].

123.2
In analogy to the procedure described in example 78.2, (2-naphthalen-2-yl-ethoxy)-acetic acid ethyl ester was treated with trimethylaluminum and ammonium chloride to obtain 2-(2-naphthalen-2-yl-ethoxy)-acetamidine hydrochloride as off-white solid. MS: m/e=229.3 [M+H⁺].

123.3
In analogy to the procedure described in example 78.3, 2,5-dichloronicotinic acid was reacted with 2-(2-naphthalen-2-yl-ethoxy)-acetamidine hydrochloride in the presence of TBTU and DIPEA to give 2,5-dichloro-N-[1-imino-2-(2-naphthalen-2-yl-ethoxy)-ethyl]-nicotinamide as yellow oil. MS: m/e=402.3 [M+H⁺].

123.4
In analogy to the procedure described in example 78.4, 2,5-dichloro-N-[1-imino-2-(2-naphthalen-2-yl-ethoxy)-ethyl]-nicotinamide was treated with potassium carbonate in DMF for 3 h at 100° C. to obtain 6-chloro-2-(2-naphthalen-2-yl-ethoxymethyl)-3H-pyrido[2,3-d]pyrimidin-4-one as brown crystals. MS: m/e=366.0 [M+H⁺].

Example 124

2-[2-(2,5-Difluoro-phenyl)-ethoxymethyl]-6-ethyl-3H-pyrido[2,3-d]pyrimidin-4-one 124.1
A 1 N aqueous LiOH solution (3.3 ml, 3.3 mmol) was added to a solution of 2-chloro-5-ethyl-nicotinic acid methyl ester (325 mg, 1.6 mmol; T. Y. Zhang, E. F. V. Scriven, WO 9318005 A2) in THF (3.3 ml). The reaction mixture was stirred for 3 h at ambient temperature, poured onto ice water/isopropyl acetate 1/1 and acidified with 1 N aqueous HCl solution. The layers were separated and the aqueous layer was extracted two times with isopropyl acetate. The combined extracts were washed with brine, dried over sodium sulfate and the solvent was removed under reduced pressure to give 2-chloro-5-ethyl-nicotinic acid as white solid (292 mg, 1.57 mmol; 97%) which was used in the next step without further purification. MS: m/e=184.1 [M−H⁻].

124.2
In analogy to the procedure described in example 78.3, 2-chloro-5-ethyl-nicotinic acid was reacted with 2-[2-(2,5-difluoro-phenyl)-ethoxy]-acetamidine hydrochloride (example 78.2) in the presence of TBTU and DIPEA to give 2-chloro-N-{2-[2-(2,5-difluoro-phenyl)-ethoxy]-1-imino-ethyl}-5-ethyl-nicotinamide as yellow oil. MS: m/e=382.3 [M+H⁺].

124.3
In analogy to the procedure described in example 78.4, 2-chloro-N-{2-[2-(2,5-difluoro-phenyl)-ethoxy]-1-imino-ethyl}-5-ethyl-nicotinamide was treated with potassium carbonate in DMF for 5 h at 100° C. to obtain 2-[2-(2,5-difluoro-phenyl)-ethoxymethyl]-6-ethyl-3H-pyrido[2,3-d]pyrimidin-4-one as off-white crystals. MS: m/e=346.1 [M+H⁺].

Example 125

2-[2-(3-Chloro-phenyl)-ethoxymethyl]-6-ethyl-3H-pyrido[2,3-d]pyrimidin-4-one 125.1
In analogy to the procedure described in example 78.3, 2-chloro-5-ethyl-nicotinic acid (example 124.1) was reacted with 2-[2-(3-chloro-phenyl)-ethoxy]-acetamidine hydrochloride (example 79.2) in the presence of TBTU and DIPEA to give 2-chloro-N-{2-[2-(3-chloro-phenyl)-ethoxy]-1-imino-ethyl}-5-ethyl-nicotinamide as yellow oil. MS: m/e=380.2 [M+H⁺].

125.2
In analogy to the procedure described in example 78.4, 2-chloro-N-{2-[2-(3-chloro-phenyl)-ethoxy]-1-imino-ethyl}-5-ethyl-nicotinamide was treated with potassium carbonate in DMF for 5 h at 100° C. to obtain 2-[2-(3-chloro-phenyl)-ethoxymethyl]-6-ethyl-3H-pyrido[2,3-d]pyrimidin-4-one as off-white crystals. MS: m/e=344.3 [M+H⁺].

Example 126

6-Butyl-2-[2-(3-chloro-phenyl)-ethoxymethyl]-3H-pyrido[2,3-d]pyrimidin-4-one 126.1

Hexanal (6.06 ml, 50 mmol) and piperidine (0.16 ml) were added to a solution of mehtylcyano acetate (4.4 ml, 49 mmol) in acetic acid (6.8 ml). The solution was stirred for 14 h at ambient temperature and poured onto ice water/dichloromethane 1/1. The layers were separated and the aqueous layer was extracted two times with dichloromethane. The combined extracts were washed with ice water, dried over sodium sulfate and the solvent was removed under reduced pressure to yield (E)-2-cyano-oct-2-enoic acid methyl ester as yellow oil (9.66 g, 53 mmol; quant.) which was used in the next step without further purification. MS: m/e=199.1 [M+NH$_4$+].

126.2

Phosporous oxychloride (4.76 ml, 51 mmol) was added within 10 minutes to an ice cold solution of (E)-2-cyano-oct-2-enoic acid methyl ester (4.65 g, 26 mmol) in DMF (12 ml) under an argon atmosphere. The reaction mixture was stirred for 14 h at 80° C. and poured onto ice water. After 3 h the mixture was extracted two times with dichloromethane, the combined extracts were washed with ice water and dried over sodium sulfate. Removal of the solvent under reduced pressure left a brown oil which was purified by column chromatography (silica gel, isopropyl acetate/heptane) to give 5-butyl-2-chloro-nicotinic acid methyl ester (1.01 g, 4.4 mmol; 17%) as yellow oil. MS: m/e=227.0 [M+H$^+$].

126.3

In analogy to the procedure described in example 124.1, 5-butyl-2-chloro-nicotinic acid methyl ester was treated with LiOH in THF to give 5-butyl-2-chloro-nicotinic acid as colorless crystals. MS: m/e=212.2 [M−H$^−$].

126.4

In analogy to the procedure described in example 78.3, 5-butyl-2-chloro-nicotinic acid was reacted with 2-[2-(3-chloro-phenyl)-ethoxy]-acetamidine hydrochloride (example 79.2) in the presence of TBTU and DIPEA to give 5-butyl-2-chloro-N-{2-[2-(3-chloro-phenyl)-ethoxy]-1-imino-ethyl}-nicotinamide as yellow oil. MS: m/e=408.3 [M+H$^+$].

126.5

In analogy to the procedure described in example 78.4, 5-butyl-2-chloro-N-{2-[2-(3-chloro-phenyl)-ethoxy]-1-imino-ethyl}-nicotinamide was treated with KOtBu in DMSO to obtain 6-butyl-2-[2-(3-chloro-phenyl)-ethoxymethyl]-3H-pyrido[2,3-d]pyrimidin-4-one as off-white crystals. MS: m/e=370.4 [M−H$^−$].

Example 127

6-Butyl-2-[2-(2,5-difluoro-phenyl)-ethoxymethyl]-3H-pyrido[2,3-d]pyrimidin-4-one 127.1

In analogy to the procedure described in example 78.3, 5-butyl-2-chloro-nicotinic acid (example 126.3) was reacted with 2-[2-(2,5-difluoro-phenyl)-ethoxy]-acetamidine hydrochloride (example 78.2) in the presence of TBTU and DIPEA to give 5-butyl-2-chloro-N-{2-[2-(2,5-difluoro-phenyl)-ethoxy]-1-imino-ethyl}-nicotinamide as orange oil. MS: m/e=410.1 [M+H$^+$].

127.2

In analogy to the procedure described in example 78.4, 5-butyl-2-chloro-N-{2-[2-(2,5-difluoro-phenyl)-ethoxy]-1-imino-ethyl}-nicotinamide was treated with KOtBu in DMSO to obtain 6-butyl-2-[2-(2,5-difluoro-phenyl)-ethoxymethyl]-3H-pyrido[2,3-d]pyrimidin-4-one as off-white crystals. MS: m/e=374.4 [M+H$^+$].

Example 128

2-[2-(3-Chloro-4-fluoro-phenyl)-ethoxymethyl]-6-ethyl-3H-pyrido[2,3-d]pyrimidin-4-one 128.1

In analogy to the procedure described in example 78.3, 2-chloro-5-ethyl-nicotinic acid (example 124.1) was reacted with 2-[2-(3-chloro-4-fluoro-phenyl)-ethoxy]-acetamidine hydrochloride (example 82.2) in the presence of TBTU and DIPEA to give 2-chloro-N-{2-[2-(3-chloro-4-fluoro-phenyl)-ethoxy]-1-imino-ethyl}-5-ethyl-nicotinamide as yellow oil. MS: m/e=398.1 [M+H$^+$].

128.2

In analogy to the procedure described in example 78.4, 2-chloro-N-{2-[2-(3-chloro-4-fluoro-phenyl)-ethoxy]-1-imino-ethyl}-5-ethyl-nicotinamide was treated with KOtBu in DMSO to obtain 2-[2-(3-chloro-4-fluoro-phenyl)-ethoxymethyl]-6-ethyl-3H-pyrido[2,3-d]pyrimidin-4-one as off-white crystals. MS: m/e=362.1 [M+H$^+$].

Example 129

6-Cyclopropyl-2-(4-phenyl-butyl)-3H-pyrido[2,3-d]pyrimidin-4-one

Palladium(II) acetate (1 mg, 4.5 μmol) was added to a degassed suspension of 6-bromo-2-(4-phenyl-butyl)-3H-pyrido[2,3-d]pyrimidin-4-one (20 mg, 55 μmol; example 26), cyclopropyl boronic acid (10 mg, 110 μmol), potassium phosphate (59 mg, 275 μmol) and tricyclohexylphosphine (3 mg, 9 μmol) in toluene (360 μl) and water (24 μl) under an argon atmosphere. The reaction mixture was heated for 14 h to 100° C. and poured onto ice cold isopropyl acetate/brine 1/1. The layers were separated, the aqueous layer was extracted two times with isopropyl acetate, the combined extracts were washed with brine and dried over sodium sulfate. Removal of the solvent under reduced pressure left a yellow solid which was purified by preparative thin layer chromatography (silica gel, isopropyl acetate/heptane) to give 6-cyclopropyl-2-(4-phenyl-butyl)-3H-pyrido[2,3-d]pyrimidin-4-one (1 mg, 3.1 μmol; 6%) as yellow crystals. MS: m/e=320.2 [M+H$^+$].

Example 130

2-(2-Fluoro-phenyl)-ethanesulfonic acid (4-oxo-3,4-dihydro-pyrido[2,3-d]pyrimidin-2-ylmethyl)-amide To an ice cooled suspension of 2-aminomethyl-3H-pyrido[2,3-d]pyrimidin-4-one (example 84.3; 50 mg, 0.58 mmol) in CH$_2$Cl$_2$ (2 ml) were added DIPEA (0.10 ml, 0.58 mmol) and 2-(2-fluoro-phenyl)-ethanesulfonyl chloride (78 mg, 0.35 mmol). The reaction mixture was stirred for 3 hours at 0° C. Unreacted 2-aminomethyl-3H-pyrido[2,3-d]pyrimidin-4- one was filtered off, the filtrate was evaporated to dryness and chromatographed (silica gel, EtOAc) to yield 2-(2-fluorophenyl)-ethanesulfonic acid (4-oxo-3,4-dihydro-pyrido[2,3-d]pyrimidin-2-ylmethyl)-amide (12 mg, 0.034 mmol; 12%) as a white solid. MS (m/e): 363.1 [M+H$^+$].

Example 131

2-(3-Chloro-phenyl)-ethanesulfonic acid (4-oxo-3,4-dihydro-pyrido[2,3-d]pyrimidin-2-ylmethyl)-amide In analogy to example 130, from 2-aminomethyl-3H-pyrido[2,3-d]pyrimidin-4-one (example 84.3) and 2-(3-chloro-phenyl)-ethanesulfonyl chloride was prepared 2-(3-chloro-phenyl)-ethanesulfonic acid (4-oxo-3,4-dihydro-pyrido[2,3-d]pyrimidin-2-ylmethyl)-amide as a light brown solid. MS (m/e): 379.1 [M+H$^+$].

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 (polyvinylpyrrolidone) | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxyde (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| | |
|---|---|
| Capsule contents | |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 (sorbitol) | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidone K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

Unless stated to the contrary, all compounds in the examples were prepared and characterized as described. All ranges recited herein encompass all combinations and subcombinations included within that range limit. All patents and publications cited herein are hereby incorporated by reference in their entirety.

The invention claimed is:

1. A compound of formula (I):

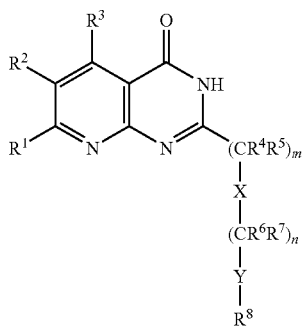

or a pharmaceutically acceptable salt or ester thereof, wherein:
(a) X is selected from the group consisting of:
  (1) a single bond,
  (2) O,
  (3) N($R^9$)C(O),
  (4) N($R^9$)C(O)O,
  (5) OC(O)N$R^9$,
  (6) N($R^9$)C(O)N$R^{10}$,
  (7) N($R^9$)SO$_2$, and
  (8) C(O)N$R^9$ if m is 1, 2 or 3;
(b) Y is selected from the group consisting of:
  (1) a single bond, and
  (2) O if n is 1, 2, 3, 4, 5 or 6;
(c) $R^1$, $R^2$ and $R^3$ are independently from each other selected from the group consisting of:
  (1) hydrogen,
  (2) halogen,
  (3) lower-alkyl,
  (4) fluoro-lower-alkyl,
  (5) lower-alkoxy,
  (6) fluoro-lower-alkoxy, and
  (7) cycloalkyl;
(d) $R^4$, $R^5$, $R^6$ and $R^7$ are independently from each other selected from the group consisting of:
  (1) hydrogen,
  (2) fluoro,
  (3) lower-alkyl, and
  (4) fluoro-lower-alkyl; or alternatively,
  $R^4$ and $R^5$ are bound together to form a ring together with the carbon atom to which they are attached wherein —$R^4$—$R^5$— is —(CH$_2$)$_{2-6}$—, or $R^6$ and $R^7$ are bound together to form a ring together with the carbon atom to which they are attached wherein —$R^6$—$R^7$— is —(CH$_2$)$_{2-6}$—;
(e) $R^8$ is aryl or heteroaryl, wherein said aryl or heteroaryl is optionally substituted with 1 to 3 substituents independently from each other selected from the group consisting of:
  (1) halogen,
  (2) lower-alkyl,
  (3) lower-alkoxy,
  (4) fluoro-lower-alkyl,
  (5) fluoro-lower-alkoxy,
  (6) cycloalkyl,
  (7) fluoro-cycloalkyl,
  (8) cycloalkyl-oxy,
  (9) C(O)OH,
  (10) lower-alkoxy-C(O),
  (11) NH$_2$C(O),
  (12) N(H,lower-alkyl)C(O),
  (13) N(lower-alkyl)$_2$C(O),
  (14) OH,
  (15) lower-alkyl-C(O)O,
  (16) NH$_2$,
  (17) N(H,lower-alkyl),
  (18) N(lower-alkyl)$_2$,
  (19) lower-alkyl-C(O)NH,
  (20) lower-alkyl-C(O)N(lower-alkyl),
  (21) NH$_2$SO$_2$,
  (22) N(H,lower-alkyl)SO$_2$,
  (23) N(lower-alkyl)$_2$SO$_2$,
  (24) lower-alkyl-SO$_2$—NH,
  (25) lower-alkyl-SO$_2$—N(lower-alkyl),
  (26) cyano, and
  (27) phenyl which is optionally substituted with 1 to 3 substituents independently selected from the group consisting of halogen, lower-alkyl, lower-alkoxy and fluoro-lower-alkyl;
(f) $R^9$ and $R^{10}$ independently from each other are selected from the group consisting of:
  (1) hydrogen,
  (2) lower-alkyl, and
  (3) fluoro-lower-alkyl; and
(g) m is 0, 1, 2 or 3; and n is 0, 1, 2, 3, 4, 5 or 6; wherein m+n is $\geq$1.

2. A compound of claim 1, wherein:
(a) X is selected from the group consisting of:
  (1) a single bond,
  (2) O,
  (3) N($R^9$)C(O),
  (4) N($R^9$)C(O)O,
  (5) OC(O)N$R^9$,
  (6) N($R^9$)C(O)N$R^{10}$, and
  (7) C(O)N$R^9$ if m is 1, 2 or 3; and
(b) Y is selected from the group consisting of:
  (1) a single bond, and
  (2) O if n is 1, 3, 4, 5 or 6.

3. A compound of claim 1, wherein X is selected from the group consisting of:
  (1) a single bond,
  (2) O,
  (3) N($R^9$)C(O),
  (4) N($R^9$)C(O)O, and
  (5) N($R^9$)C(O)N$R^{10}$.

4. A compound of claim 1, wherein X is selected from the group consisting of:
  (1) a single bond,
  (2) O,
  (3) N($R^9$)C(O), and
  (4) N($R^9$)C(O)O.

5. A compound of claim 1, wherein X is N($R^9$)SO$_2$.

6. A compound of claim 1, wherein Y is a single bond.

7. A compound of claim 1, wherein Y is O.

8. A compound of claim 1, wherein $R^1$, $R^2$ and $R^3$ independently from each other are selected from the group consisting of hydrogen, halogen and lower-alkyl.

9. A compound of claim 1, wherein $R^1$ is hydrogen, methyl or fluoro.

10. A compound of claim 1, wherein $R^2$ is hydrogen, methyl, ethyl, butyl, fluoro, chloro or bromo.

11. A compound of to claim 1, wherein $R^3$ is hydrogen.

12. A compound of claim 1, wherein $R^4$, $R^5$, $R^6$ and $R^7$ independently from each other are selected from the group consisting of hydrogen and lower-alkyl.

13. A compound of claim 1, wherein $R^4$, $R^5$, $R^6$ and $R^7$ are hydrogen.

14. A compound of claim 1, wherein $R^8$ is aryl or heteroaryl, which aryl or heteroaryl is optionally substituted with 1 to 3 substituents independently selected from the group consisting of:
   (1) halogen,
   (2) lower-alkyl,
   (3) lower-alkoxy,
   (4) fluoro-lower-alkyl,
   (5) fluoro-lower-alkoxy, and
   (6) phenyl, which is optionally substituted with halogen.

15. A compound of claim 1, wherein $R^8$ is phenyl or naphthyl, which phenyl or naphthyl is optionally substituted with 1 to 2 substituents independently selected from the group consisting of halogen and lower-alkoxy.

16. A compound of claim 1, wherein $R^8$ is phenyl, 4-fluoro-phenyl, 3-chloro-phenyl, 2-methoxy-phenyl, 2-chloro-phenyl, 2-fluoro-phenyl, 3,4-dichloro-phenyl, naphthalen-1-yl or naphthalen-2-yl.

17. A compound of claim 1, wherein $R^8$ is 3-chloro-4-fluoro-phenyl, 2,5-difluoro-phenyl or 5-methyl-2-phenyl-oxazol-4-yl.

18. A compound of claim 1, wherein m is 0 or 1.

19. A compound of claim 1, wherein n is 0, 1, 2, 3 or 4.

20. A compound of claim 1, wherein $R^9$ and $R^{10}$ are hydrogen.

21. A compound of claim 1 selected from the group consisting of:
   2-Benzyloxymethyl-3H-pyrido[2,3-d]pyrimidin-4-one,
   2-Phenoxymethyl-3H-pyrido[2,3-d]pyrimidin-4-one,
   2-(4-Chloro-phenoxymethyl)-3H-pyrido[2,3-d]pyrimidin-4-one,
   2-(5-Phenyl-pentyl)-3H-pyrido[2,3-d]pyrimidin-4-one,
   2-(4-Methoxy-phenoxymethyl)-3H-pyrido[2,3-d]pyrimidin-4-one,
   2-(4-Ethyl-phenoxymethyl)-3H-pyrido[2,3-d]pyrimidin-4-one,
   2-(4-Phenyl-butyl)-3H-pyrido[2,3-d]pyrimidin-4-one,
   2-(4-Fluoro-phenoxymethyl)-3H-pyrido[2,3-d]pyrimidin-4-one,
   2-(3-Chloro-phenoxymethyl)-3H-pyrido[2,3-d]pyrimidin-4-one,
   2-Phenethyl-3H-pyrido[2,3-d]pyrimidin-4-one, and
   any pharmaceutically acceptable salt or ester thereof.

22. A compound of claim 1 selected from the group consisting of:
   2-[2-(3-Chloro-phenyl)-ethyl]-3H-pyrido[2,3-d]pyrimidin-4-one,
   2-[2-(3-Methoxy-phenyl)-ethyl]-3H-pyrido[2,3-d]pyrimidin-4-one,
   2-[4-(4-Chloro-phenyl)-butyl]-3H-pyrido[2,3-d]pyrimidin-4-one,
   2-(6-Phenyl-hexyl)-3H-pyrido[2,3-d]pyrimidin-4-one,
   2-[4-(4-Fluoro-phenyl)-butyl]-3H-pyrido[2,3-d]pyrimidin-4-one,
   2-(2-Methoxy-phenoxymethyl)-3H-pyrido[2,3-d]pyrimidin-4-one,
   2-p-Tolyloxymethyl-3H-pyrido[2,3-d]pyrimidin-4-one,
   2-(2-Chloro-phenoxymethyl)-3H-pyrido[2,3-d]pyrimidin-4-one,
   2-(2,3-Dimethyl-phenoxymethyl)-3H-pyrido[2,3-d]pyrimidin-4-one,
   2-(Naphthalen-1-yloxymethyl)-3H-pyrido[2,3-d]pyrimidin-4-one, and
   any pharmaceutically acceptable salt or ester thereof.

23. A compound of claim 1 selected from the group consisting of:
   2-(4-Chloro-2-methyl-phenoxymethyl)-3H-pyrido[2,3-d]pyrimidin-4-one,
   6-Methyl-2-(4-phenyl-butyl)-3H-pyrido[2,3-d]pyrimidin-4-one,
   (4-Oxo-3,4-dihydro-pyrido[2,3-d]pyrimidin-2-ylmethyl)-carbamic acid benzyl ester,
   N-(4-Oxo-3,4-dihydro-pyrido[2,3-d]pyrimidin-2-ylmethyl)-3-phenyl-propionamide,
   N-(4-Oxo-3,4-dihydro-pyrido[2,3-d]pyrimidin-2-ylmethyl)-4-phenyl-butyramide,
   6-Bromo-2-(4-phenyl-butyl)-3H-pyrido[2,3-d]pyrimidin-4-one,
   6-Bromo-2-[4-(4-fluoro-phenyl)-butyl]-3H-pyrido[2,3-d]pyrimidin-4-one,
   2-[3-(4-Methoxy-phenyl)-propoxy]-3H-pyrido[2,3-d]pyrimidin-4-one,
   2-(3-Phenyl-propoxy)-3H-pyrido[2,3-d]pyrimidin-4-one,
   2-(4-Phenyl-butoxy)-3H-pyrido[2,3-d]pyrimidin-4-one, and
   any pharmaceutically acceptable salt or ester thereof.

24. A compound of claim 1 selected from the group consisting of:
   2-[4-(4-Methoxy-phenyl)-butoxy]-3H-pyrido[2,3-d]pyrimidin-4-one,
   2-(3-Pyridin-3-yl-propoxy)-3H-pyrido[2,3-d]pyrimidin-4-one,
   2-(2-Phenoxy-ethoxy)-3H-pyrido[2,3-d]pyrimidin-4-one,
   2-[2-(Naphthalen-2-yloxy)-ethoxy]-3H-pyrido[2,3-d]pyrimidin-4-one,
   2-(3-Phenoxy-propoxy)-3H-pyrido[2,3-d]pyrimidin-4-one,
   2-Phenethyloxymethyl-3H-pyrido[2,3-d]pyrimidin-4-one,
   2-[2-(2-Fluoro-phenyl)-ethoxymethyl]-3H-pyrido[2,3-d]pyrimidin-4-one,
   2-[3-(3,4-Difluoro-phenoxy)-propoxy]-3H-pyrido[2,3-d]pyrimidin-4-one,
   2-[3-(4-Methoxy-phenoxy)-propoxy]-3H-pyrido[2,3-d]pyrimidin-4-one,
   2-[2-(4-Fluoro-phenyl)-ethoxymethyl]-3H-pyrido[2,3-d]pyrimidin-4-one, and
   any pharmaceutically acceptable salt or ester thereof.

25. A compound of claim 1 selected from the group consisting of:
   2-[4-(4-Fluoro-phenyl)-3-methyl-butyl]-3H-pyrido[2,3-d]pyrimidin-4-one,
   2-[5-(4-Chloro-phenyl)-pentyl]-3H-pyrido[2,3-d]pyrimidin-4-one,
   2-[3-(4-Fluoro-phenoxy)-propyl]-3H-pyrido[2,3-d]pyrimidin-4-one,
   2-[2-(4-Chloro-phenyl)-ethoxymethyl]-3H-pyrido[2,3-d]pyrimidin-4-one,
   2-(2-p-Tolyl-ethoxymethyl)-3H-pyrido[2,3-d]pyrimidin-4-one,
   2-[2-(4-Methoxy-phenyl)-ethoxymethyl]-3H-pyrido[2,3-d]pyrimidin-4-one,
   2-(2-Benzyloxy-ethyl)-3H-pyrido[2,3-d]pyrimidin-4-one,
   2-(4'-Fluoro-biphenyl-4-yloxymethyl)-3H-pyrido[2,3-d]pyrimidin-4-one,
   2-(4-m-Tolyl-butyl)-3H-pyrido[2,3-d]pyrimidin-4-one,
   2-(1-Methyl-4-phenyl-butyl)-3H-pyrido[2,3-d]pyrimidin-4-one, and
   any pharmaceutically acceptable salt or ester thereof.

26. A compound of claim 1 selected from the group consisting of:
   2-(Naphthalen-2-yloxymethyl)-3H-pyrido[2,3-d]pyrimidin-4-one, 1-Benzyl-3-(4-oxo-3,4-dihydro-pyrido[2,3-d]pyrimidin-2-ylmethyl)-urea,
2-[2-(4-Fluoro-phenyl)-ethoxymethyl]-6-methyl-3H-pyrido[2,3-d]pyrimidin-4-one,
2-(4-Iodo-phenoxymethyl)-3H-pyrido[2,3-d]pyrimidin-4-one,
2-[3-(4-Fluoro-phenoxy)-propoxy]-3H-pyrido[2,3-d]pyrimidin-4-one,
2-(3-p-Tolyloxy-propoxy)-3H-pyrido[2,3-d]pyrimidin-4-one,
2-[3-(2-Fluoro-phenoxy)-propoxy]-3H-pyrido[2,3-d]pyrimidin-4-one,
2-(3-o-Tolyloxy-propoxy)-3H-pyrido[2,3-d]pyrimidin-4-one,
2-[2-(2-Fluoro-phenyl)-ethoxymethyl]-7-methyl-3H-pyrido[2,3-d]pyrimidin-4-one,
(4-Oxo-3,4-dihydro-pyrido[2,3-d]pyrimidin-2-ylmethyl)-carbamic acid 2-chloro-benzyl ester, and
any pharmaceutically acceptable salt or ester thereof.

27. A compound of claim 1 selected from the group consisting of:
2-[3-(3-Fluoro-phenoxy)-propoxy]-3H-pyrido[2,3-d]pyrimidin-4-one,
2-(3-m-Tolyloxy-propoxy)-3H-pyrido[2,3-d]pyrimidin-4-one,
2-[2-(2-Trifluoromethyl-phenyl)-ethoxymethyl]-3H-pyrido[2,3-d]pyrimidin-4-one,
2-[2-(2-Methoxy-phenyl)-ethoxymethyl]-3H-pyrido[2,3-d]pyrimidin-4-one,
2-(2-o-Tolyl-ethoxymethyl)-3H-pyrido[2,3-d]pyrimidin-4-one,
2-[2-(2-Chloro-phenyl)-ethoxymethyl]-3H-pyrido[2,3-d]pyrimidin-4-one,
2-Phenethyloxy-3H-pyrido[2,3-d]pyrimidin-4-one,
2-(3,4-Dichloro-benzyloxy)-3H-pyrido[2,3-d]pyrimidin-4-one,
2-[2-(4-Fluoro-phenyl)-ethoxy]-3H-pyrido[2,3-d]pyrimidin-4-one,
2-(2,4-Difluoro-benzyloxy)-3H-pyrido[2,3-d]pyrimidin-4-one, and
any pharmaceutically acceptable salt or ester thereof.

28. A compound of claim 1 selected from the group consisting of:
2-[2-(4-Chloro-phenyl)-ethoxy]-3H-pyrido[2,3-d]pyrimidin-4-one,
2-(5-Phenyl-pentyloxy)-3H-pyrido[2,3-d]pyrimidin-4-one,
2-(6-Phenyl-hexyloxy)-3H-pyrido[2,3-d]pyrimidin-4-one,
2-[3-(4-Chloro-phenoxy)-propoxy]-3H-pyrido[2,3-d]pyrimidin-4-one,
2-[3-(2-Chloro-phenoxy)-propoxy]-3H-pyrido[2,3-d]pyrimidin-4-one,
2-[2-(3-Chloro-phenyl)-ethoxymethyl]-3H-pyrido[2,3-d]pyrimidin-4-one,
(6-Methyl-4-oxo-3,4-dihydro-pyrido[2,3-d]pyrimidin-2-ylmethyl)-carbamic acid benzyl ester, and
any pharmaceutically acceptable salt or ester thereof.

29. A compound of claims 1 selected from the group consisting of:
2-[4-(4-Fluoro-phenyl)-butyl]-3H-pyrido[2,3-d]pyrimidin-4-one,
2-(2-Methoxy-phenoxymethyl)-3H-pyrido[2,3-d]pyrimidin-4-one,
2-(Naphthalen-1-yloxymethyl)-3H-pyrido[2,3-d]pyrimidin-4-one,
6-Methyl-2-(4-phenyl-butyl)-3H-pyrido[2,3-d]pyrimidin-4-one,
(4-Oxo-3,4-dihydro-pyrido[2,3-d]pyrimidin-2-ylmethyl)-carbamic acid benzyl ester,
N-(4-Oxo-3,4-dihydro-pyrido[2,3-d]pyrimidin-2-ylmethyl)-3-phenyl-propionamide,
2-[2-(Naphthalen-2-yloxy)-ethoxy]-3H-pyrido[2,3-d]pyrimidin-4-one,
2-(3-Phenoxy-propoxy)-3H-pyrido[2,3-d]pyrimidin-4-one, and
any pharmaceutically acceptable salt or ester thereof.

30. A compound of claim 1 selected from the group consisting of:
2-[2-(2-Fluoro-phenyl)-ethoxymethyl]-3H-pyrido[2,3-d]pyrimidin-4-one,
2-(Naphthalen-2-yloxymethyl)-3H-pyrido[2,3-d]pyrimidin-4-one,
2-[2-(2-Fluoro-phenyl)-ethoxymethyl]-7-methyl-3H-pyrido[2,3-d]pyrimidin-4-one,
2-(3,4-Dichloro-benzyloxy)-3H-pyrido[2,3-d]pyrimidin-4-one,
2-[3-(2-Chloro-phenoxy)-propoxy]-3H-pyrido[2,3-d]pyrimidin-4-one,
2-[2-(3-Chloro-phenyl)-ethoxymethyl]-3H-pyrido[2,3-d]pyrimidin-4-one, and
any pharmaceutically acceptable salt or ester thereof.

31. A compound of claim 1 selected from the group consisting of:
6-Chloro-2-[2-(2,5-difluoro-phenyl)-ethoxymethyl]-3H-pyrido[2,3-d]pyrimidin-4-one,
6-Chloro-2-[2-(3-chloro-phenyl)-ethoxymethyl]-3H-pyrido[2,3-d]pyrimidin-4-one,
6-Chloro-2-[2-(4-fluoro-phenyl)-ethoxymethyl]-3H-pyrido[2,3-d]pyrimidin-4-one,
6-Chloro-2-[2-(3-trifluoromethoxy-phenyl)-ethoxymethyl]-3H-pyrido[2,3-d]pyrimidin-4-one,
6-Chloro-2-[2-(3-chloro-4-fluoro-phenyl)-ethoxymethyl]-3H-pyrido[2,3-d]pyrimidin-4-one,
6-Chloro-2-[2-(4-chloro-phenyl)-ethoxymethyl]-3H-pyrido[2,3-d]pyrimidin-4-one,
3-(3-Fluoro-phenyl)-N-(4-oxo-3,4-dihydro-pyrido[2,3-d]pyrimidin-2-ylmethyl)-propionamide,
2-[2-(3-Chloro-phenyl)-ethoxymethyl]-6-fluoro-3H-pyrido[2,3-d]pyrimidin-4-one,
2-[2-(3-Chloro-phenyl)-ethoxymethyl]-7-fluoro-3H-pyrido[2,3-d]pyrimidin-4-one, and
any pharmaceutically acceptable salt or ester thereof.

32. A compound of claim 1 selected from the group consisting of:
2-(5-Methyl-2-phenyl-oxazol-4-yl)-N-(4-oxo-3,4-dihydro-pyrido[2,3-d]pyrimidin-2-ylmethyl)-acetamide,
2-[1,2,4]Triazol-1-ylmethyl-3H-pyrido[2,3-d]pyrimidin-4-one,
2-(3-Chloro-phenoxy)-N-(4-oxo-3,4-dihydro-pyrido[2,3-d]pyrimidin-2-ylmethyl)-acetamide,
N-(4-Oxo-3,4-dihydro-pyrido[2,3-d]pyrimidin-2-ylmethyl)-2-(pyridin-2-yloxy)-acetamide,
2-[2-(3-Fluoro-phenyl)-ethoxymethyl]-3H-pyrido[2,3-d]pyrimidin-4-one,
2-[2-(3-Methoxy-phenyl)-ethoxymethyl]-3H-pyrido[2,3-d]pyrimidin-4-one,
7-Fluoro-2-[4-(4-fluoro-phenyl)-butyl]-3H-pyrido[2,3-d]pyrimidin-4-one,
7-Fluoro-2-[2-(2-fluoro-phenyl)-ethoxymethyl]-3H-pyrido[2,3-d]pyrimidin-4-one,
N-(6-Fluoro-4-oxo-3,4-dihydro-pyrido[2,3-d]pyrimidin-2-ylmethyl)-3-phenyl-propionamide, and
any pharmaceutically acceptable salt or ester thereof.

33. A compound of claim 1 selected from the group consisting of:
7-Fluoro-2-[2-(3-trifluoromethyl-phenyl)-ethoxymethyl]-3H-pyrido[2,3-d]pyrimidin-4-one,
5-Methyl-2-(5-phenyl-pentyloxy)-3H-pyrido[2,3-d]pyrimidin-4-one, 6-Chloro-2-(3-phenoxy-propoxy)-3H-pyrido[2,3-d]pyrimidin-4-one,
7-Methyl-2-(5-phenyl-pentyloxy)-3H-pyrido[2,3-d]pyrimidin-4-one,
2-[3-(2-Chloro-phenoxy)-propoxy]-5-methyl-3H-pyrido[2,3-d]pyrimidin-4-one,
7-Fluoro-2-[2-(3-fluoro-phenyl)-ethoxymethyl]-3H-pyrido[2,3-d]pyrimidin-4-one,
7-Fluoro-2-[2-(4-fluoro-phenyl)-ethoxymethyl]-3H-pyrido[2,3-d]pyrimidin-4-one,
3-(2-Chloro-phenyl)-N-(4-oxo-3,4-dihydro-pyrido[2,3-d]pyrimidin-2-ylmethyl)-propionamide,
3-(3-Chloro-phenyl)-N-(4-oxo-3,4-dihydro-pyrido[2,3-d]pyrimidin-2-ylmethyl)-propionamide,
and any pharmaceutically acceptable salt or ester thereof.

34. A compound of claim 1 selected from the group consisting of:
2-[2-(2-Chloro-phenyl)-ethoxymethyl]-7-fluoro-3H-pyrido[2,3-d]pyrimidin-4-one,
6-Chloro-2-[2-(2-chloro-phenyl)-ethoxymethyl]-3H-pyrido[2,3-d]pyrimidin-4-one,
6-Fluoro-2-[2-(3-fluoro-phenyl)-ethoxymethyl]-3H-pyrido[2,3-d]pyrimidin-4-one,
6-Chloro-2-[4-(4-fluoro-phenyl)-butyl]-3H-pyrido[2,3-d]pyrimidin-4-one,
2-[2-(2-Chloro-6-fluoro-phenyl)-ethoxymethyl]-7-fluoro-3H-pyrido[2,3-d]pyrimidin-4-one,
2-(2-m-Tolyl-ethoxymethyl)-3H-pyrido[2,3-d]pyrimidin-4-one,
2-[2-(4-Chloro-phenyl)-ethoxymethyl]-7-fluoro-3H-pyrido[2,3-d]pyrimidin-4-one,
3-(4-Chloro-phenyl)-N-(4-oxo-3,4-dihydro-pyrido[2,3-d]pyrimidin-2-ylmethyl)-propionamide,
(6-Fluoro-4-oxo-3,4-dihydro-pyrido[2,3-d]pyrimidin-2-ylmethyl)-carbamic acid benzyl ester, and
any pharmaceutically acceptable salt or ester thereof.

35. A compound of claim 1 selected from the group consisting of:
2-[2-(2,5-Difluoro-phenyl)-ethoxymethyl]-7-fluoro-3H-pyrido[2,3-d]pyrimidin-4-one,
N-(4-Oxo-3,4-dihydro-pyrido[2,3-d]pyrimidin-2-ylmethyl)-3-m-tolyl-propionamide,
7-Fluoro-2-[2-(3-trifluoromethoxy-phenyl)-ethoxymethyl]-3H-pyrido[2,3-d]pyrimidin-4-one,
3-(3-Methoxy-phenyl)-N-(4-oxo-3,4-dihydro-pyrido[2,3-d]pyrimidin-2-ylmethyl)-propionamide,
2-[2-(3-Chloro-4-fluoro-phenyl)-ethoxymethyl]-7-fluoro-3H-pyrido[2,3-d]pyrimidin-4-one,
2-[2-(2,5-Difluoro-phenyl)-ethoxymethyl]-6-fluoro-3H-pyrido[2,3-d]pyrimidin-4-one,
(6-Chloro-4-oxo-3,4-dihydro-pyrido[2,3-d]pyrimidin-2-ylmethyl)-carbamic acid benzyl ester,
(7-Chloro-4-oxo-3,4-dihydro-pyrido[2,3-d]pyrimidin-2-ylmethyl)-carbamic acid benzyl ester,
(7-Fluoro-4-oxo-3,4-dihydro-pyrido[2,3-d]pyrimidin-2-ylmethyl)-carbamic acid benzyl ester, and
any pharmaceutically acceptable salt or ester thereof.

36. A compound of claim 1 selected from the group consisting of:
6-Chloro-2-(2-naphthalen-2-yl-ethoxymethyl)-3H-pyrido[2,3-d]pyrimidin-4-one,
2-[2-(2,5-Difluoro-phenyl)-ethoxymethyl]-6-ethyl-3H-pyrido[2,3-d]pyrimidin-4-one,
2-[2-(3-Chloro-phenyl)-ethoxymethyl]-6-ethyl-3H-pyrido[2,3-d]pyrimidin-4-one,
6-Butyl-2-[2-(3-chloro-phenyl)-ethoxymethyl]-3H-pyrido[2,3-d]pyrimidin-4-one,
6-Butyl-2-[2-(2,5-difluoro-phenyl)-ethoxymethyl]-3H-pyrido[2,3-d]pyrimidin-4-one,
2-[2-(3-Chloro-4-fluoro-phenyl)-ethoxymethyl]-6-ethyl-3H-pyrido[2,3-d]pyrimidin-4-one,
6-Cyclopropyl-2-(4-phenyl-butyl)-3H-pyrido[2,3-d]pyrimidin-4-one,
2-(2-Fluoro-phenyl)-ethanesulfonic acid (4-oxo-3,4-dihydro-pyrido[2,3-d]pyrimidin-2-ylmethyl)-amide,
2-(3-Chloro-phenyl)-ethanesulfonic acid (4-oxo-3,4-dihydro-pyrido[2,3-d]pyrimidin-2-ylmethyl)-amide, and
any pharmaceutically acceptable salt or ester thereof.

37. A compound of claim 1 selected from the group consisting of:
6-Chloro-2-[2-(3-chloro-4-fluoro-phenyl)-ethoxymethyl]-3H-pyrido[2,3-d]pyrimidin-4-one,
2-[2-(3-Chloro-phenyl)-ethoxymethyl]-6-fluoro-3H-pyrido[2,3-d]pyrimidin-4-one,
2-[2-(3-Chloro-phenyl)-ethoxymethyl]-7-fluoro-3H-pyrido[2,3-d]pyrimidin-4-one,
2-(5-Methyl-2-phenyl-oxazol-4-yl)-N-(4-oxo-3,4-dihydro-pyrido[2,3-d]pyrimidin-2-ylmethyl)-acetamide,
6-Chloro-2-(3-phenoxy-propoxy)-3H-pyrido[2,3-d]pyrimidin-4-one,
(6-Fluoro-4-oxo-3,4-dihydro-pyrido[2,3-d]pyrimidin-2-ylmethyl)-carbamic acid benzyl ester,
2-[2-(2,5-Difluoro-phenyl)-ethoxymethyl]-6-fluoro-3H-pyrido[2,3-d]pyrimidin-4-one,
2-[2-(2,5-Difluoro-phenyl)-ethoxymethyl]-6-ethyl-3H-pyrido[2,3-d]pyrimidin-4-one,
6-Butyl-2-[2-(2,5-difluoro-phenyl)-ethoxymethyl]-3H-pyrido[2,3-d]pyrimidin-4-one,
2-(2-Fluoro-phenyl)-ethanesulfonic acid (4-oxo-3,4-dihydro-pyrido[2,3-d]pyrimidin-2-ylmethyl)-amide, and
any pharmaceutically acceptable salt or ester thereof.

38. A process for the manufacture of a compound of claim 1, which process comprises converting a compound of formula (II):

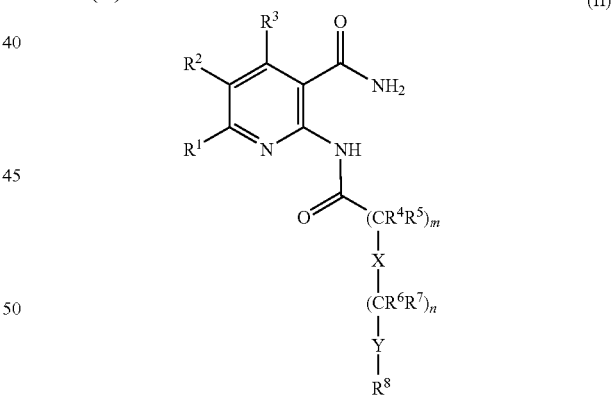

(II)

by an intramolecular condensation reaction to the compound of formula (I), wherein $R^1$, $R^2$, $R^3$, $R^4$, $R^5$, $R^6$, $R^7$, $R^8$, m, n, X and Y are as defined in claim 1.

39. A pharmaceutical composition comprising a therapeutically effective amount of a compound of claim 1 and a pharmaceutically acceptable carrier.

* * * * *

UNITED STATES PATENT AND TRADEMARK OFFICE
CERTIFICATE OF CORRECTION

| | |
|---|---|
| PATENT NO. | : 7,572,801 B2 |
| APPLICATION NO. | : 11/801863 |
| DATED | : August 11, 2009 |
| INVENTOR(S) | : Aurelia Conte et al. |

Page 1 of 1

It is certified that error appears in the above-identified patent and that said Letters Patent is hereby corrected as shown below:

On the Title Page, under Item "(65) Prior Publication Data, US 2007/0275987 A1, Nov. 29, 2007", insert:

Item -- (30) Foreign Applications Priority Data
    May 23, 2006 (EP)................ 06114438.2 --

Signed and Sealed this

Twenty-second Day of September, 2009

David J. Kappos
*Director of the United States Patent and Trademark Office*